(12) United States Patent
Ikawa et al.

(10) Patent No.: US 7,754,857 B2
(45) Date of Patent: Jul. 13, 2010

(54) HUMAN P51 GENES AND GENE PRODUCTS THEREOF

(75) Inventors: Yoji Ikawa, 3-31-8, Unoki, Ota-ku, Tokyo (JP) 146-0091; Shuntaro Ikawa, Miyagi (JP); Masuo Obinata, Miyagi (JP)

(73) Assignees: Otsuka Pharmaceutical Co., Ltd., Tokyo (JP); Yoji Ikawa, Tokyo (JP)

( * ) Notice: Subject to any disclaimer, the term of this patent is extended or adjusted under 35 U.S.C. 154(b) by 10 days.

(21) Appl. No.: 12/169,213

(22) Filed: Jul. 8, 2008

(65) Prior Publication Data

US 2009/0142783 A1 Jun. 4, 2009

Related U.S. Application Data

(62) Division of application No. 11/340,715, filed on Jan. 27, 2006, now Pat. No. 7,553,933, which is a division of application No. 09/670,568, filed on Jan. 18, 2001, now Pat. No. 7,132,276.

(51) Int. Cl.
*C07K 16/00* (2006.01)
*G01N 33/536* (2006.01)

(52) U.S. Cl. .............. 530/387.1; 435/7.1; 436/536; 436/518

(58) Field of Classification Search .............. None
See application file for complete search history.

(56) References Cited

U.S. PATENT DOCUMENTS 6,946,256 B1 * 9/2005 McKeon et al. .............. 435/7.1

FOREIGN PATENT DOCUMENTS

| WO | 98/51350 | 11/1998 |
|---|---|---|
| WO | 99/19357 | 4/1999 |
| WO | 97/28186 | 8/1999 |
| WO | 99/47674 | 9/1999 |
| WO | 99/50287 | 10/1999 |
| WO | 99/61610 | 12/1999 |

OTHER PUBLICATIONS

Yang et al, Molecular Cell, 1998, 2:305-316.
Senoo et al, Biochemical and Biophysical Res. Comm., 1998, 248:603-607/Article RC989013.
Kaghad et al., Cell, 1997, 90:809-819.
Osada et al., Nature Medicine, 1998, 4(7):839-843.
Kato et al., Blood, 1997, 90:1373-1378.
Xu et al., Jpn. J. Cancer Res., 1995, 86:284-291.
Caron de Fromentel et al., Gene, 1992, 112:241-245.
Fu et al., Proc. Natl. Acad. Sci., USA, 1995, 92:10162-10166.
Harlow et al., Molecular and Cellular Biology, 1985, 5(7):1601-1610.
Schmale et al., Oncogene, 1997, 15:1363-1367.
Chan et al., Proc. Natl. Acad. Sci., USA, 1993, 90:11371-11375.
GenEmbl accession No. Y11414 (Sep. 2, 1997).
Augustin et al., Mammalian Genome, Nov. 1, 1998, 9:899-902.

* cited by examiner

*Primary Examiner*—Misook Yu
(74) *Attorney, Agent, or Firm*—Sughrue Mion, PLLC

(57) ABSTRACT

Novel human genes falling within the category of family genes relating to p53 gene which is known as a cell proliferation regulatory gene, and gene products thereof. A human p51 gene characterized by containing a base sequence encoding an amino acid sequence represented by SEQ ID NO:1; a human p51 gene having a base sequence consisting of the 145- to 1488-bases in the sequence represented by SEQ ID NO:2; vectors containing these genes; host cells transformed with these vectors; a process for producing a p51 protein having the amino sequence represented by SEQ ID NO:1; which comprises culturing the above host cells and harvesting the protein from the thus obtained culture; and the p51 protein having the amino acid sequence represented by SEQ ID NO:1.

5 Claims, 15 Drawing Sheets

FIG. 2

```
pS1A      MSQSTQTNEF LSPEVFQHIW DFLEQPICSV QPIDLNFVDE PSEDGATNKI      50
p73β      MAQSTATSP- DGGTTFEHLW SSLE-PDSTY --FDLP-QSS RGNNEVVGGT      45
pS3       MEEPQSDPS- VEPPLSQETF SDL------- --WKL----L PENNVLSPLP      36
Consensus M.QST.T..- ..P..FQH.W SLLE-P.... ...DL.-... P.NN......      50 pS1A      EISMDCIRMQ DSDLSDPMWP QYTNLGLLNS MDQQIQNGSS STSFYNTDHA     100
p73β      DSSMQVFHLE --GMTTSVMA QF---NLLSS TMDQMSSRAA SASFYTPEHA      90
pS3       SQAMDDLMLS ----PDDI-E QW----FTED PGPDEAPRMP EAAF-RVAFA      76
Consensus ..SMD...L. --...D.... Q.---.LL.S ...Q...R.. SASFY...HA     100 pS1A      QNSVTAPSPY AQFSSTFDAL SPSPAIPSNT DYRCPHSFDV SFQQSSTAKS     150
p73β      -ASVPTHSPY AQFSSTFDTM SPAPVIPSNT DYRCPHHFEV IFQQSSTAKS     139
pS3       -PAAPTPAA- PAFAPSW-PL SSS--VPSQK TYQGSYGFRL QFLHSQTAKS     121
Consensus -.SVPTPSPY AQFSSTFD.L SPSP.IPSNT DYRCPH.F.V IFQQSSTAKS     150 pS1A      ATMTYSTELK KLYCQIAKTC PIQIKVMTRP FKQAVIRAMP VYKKAEHNTE     200
p73β      ATMTYSPLLK KLYCQIAKTC PIQIKVSTRP FKQTAIRAMP VYKKAEHNTD     189
pS3       VTKTYSPALN KMFCQLAKTC PVQLWVDSTP PPGTRVRAMA IYKQSQHMTE     171
Consensus ATMTYSPLLK KLYCQIAKTC PIQIKV.TRP FKQT.IRAMP VYKKAEHNTE     200 pS1A      VVKRCPNHEL SREFNDGQIA PPSHLIRVEG NSHAQYVEDP TTKRCSVLVR     250
p73β      VVKRCPNHEL GRDFNDGQSA PASHLIRVEG NNLSQYVDDP VTGRQSVLVR     239
pS3       VVRRCPHHER CSD-SDG-LA PPQHLIRVEG NLRVEYLDDR NTFRHSVVVR     219
Consensus VVKRCPNHEL .RDFNDGQ.A PPSHLIRVEG N...QYVDDP TT.RQSVLVR     250 pS1A      YEPPQVGTEF TTVLYNFMCN SSCMGGMNRR PILTIINTLET RDGQVLGRRC     300
p73β      YEPPQVGTEF TTILYNFMCN SSCMGGMNRR PILIIITLEM RDGQVLGRRS     289
pS3       YEPPEVGSDC TTIHYNYMCN SSCMGGMNRR PILTIITLED SSGNLLGRHS     269
Consensus YEPPQVGTEF TTILYNFMCN SSCMGGMNRR PILIIITLE. RDGQVLGRRS     300 pS1A      FEARICACPG RDRKADEDSI RKQQVSD--S TKNGDGTKRP FRQNTHGI-Q     347
p73β      FEQRICACPG RDRKADEDHY REQQALNESS AKNGAASKRA FKQSPPAVPA     339
pS3       FEVRVCACPG RDRRTEEENL RKKGEPH--H ELPPGSTKRA LPNNTSS---     314
Consensus FE.RICACPG RDRKADED.. RKQQ...--S .KNG..TKRA F.QNT...-.     350 pS1A      M-TSIMKRRS FDELLYPLPV RGRETYEMLL KIHESLELMQ YLPQHTIETY     396
p73β      LGAGVHKRRH QDEDTYYLQV RGRENFEILM KLHESLELME LVPQPLVDSY     389
pS3       --SPQPKKKP LDGEYFTLQI RGRERFEMFR ELNEALELKD AQAGKEPGGS     362
Consensus .-...KKRR. QD.E..YLQV RGR..FEML. KLHESLELM. ..PQ.....Y     400 pS1A      RQQQQQQHQ- HL------ ----LQK-H- -LLSACFRNE LV-EPRRE--     427
p73β      RQQQQLLQRP SHLQPPSYGP VLSPMHKVHG GMNKLPSVNQ LVGQPPPHSS     439
pS3       RAHSS----- HL------ ------K--- -----SKKGQ ---STSRH--     380
Consensus .QQQQ..... .HL------ ----.K-H- -.......NQ LV-.P.RH--     450 pS1A      --TPKQSDV- --FFR---HS KPPN------ ---------- ----RSVYP-     448
p73β      AATPNLGPVG PGHLNNHGHA VPANGEMSSS HSAQSMVSGS HCTPPPPYHA     489
pS3       ---KKL---- --MFK----T EGPD------ ---------- ----SD---     393
Consensus --TPKL..V- --MF.---H. .PPN------ ---------- ----S.Y.-     500 pS1A      ---------                                                  448
p73β      DPSLVRTWGP                                                 499
pS3       ---------                                                  393
Consensus ---------                                                  510
```

FIG. 3

```
p51B       MSQSTQTNEF LSPEVRQH IW DHLDQH ICSV QPIDUNFVDE PSEDGATHKI    50
p73d       MAQSTATSP- DGGTYRHHUW SSLE PDSTY --RDLP-QSS RGNNEVVGGT       45
Consensus  M QST T    .........  LE  .... ....  D .... ..........      50 p51B       EISHQCIRMQ DSDLSDPMWP QYTNLQLLHS MDQQIQNGSS SISPYNTQHA        100
p73d       DSSMQVFHLE --GMTTSVMA QF---HLUSS TMQQMSSRAA SASPYTPRHA         90
Consensus  .SMQ...... .......... Q ... LL S .. . S..  S SPY.. HA        100 p51B       QHSVTAPSPY AQPSSTFQAL SRSPHIPSNT DYPGPHS PV HFQQSSTAKS        150
p73d       -ASVPTHSPY AQPSSTFQTM SRAPH IPSNT DYPGPH RV NFQQSSTAKS        139
Consensus  . SV.. SPY AQPSSTF .. SR P IPSNT DYPGPH  V  FQQSSTAKS        150 p51B       ATWTYSTELK KLYCQIAKTC PIQIKVHTPP RQAVIRAMP VYKKAEHVTE         200
p73d       ATWTYSPULK KLYCQIAKTC PIQIKVSTPP RQTAIRAMP VYKKAEHVTD         189
Consensus  ATWTYS. LK KLYCQIAKTC PIQIKV TPP RQ  IRAMP VYKKAEHVT.         200 p51B       VVKRCPNHEL SRHFNEGQIA PPSHLIRVEG NSHAQYVHDP ITGRQSVLVR        250
p73d       VVKRCPNHEL QRDFNEGQSA PASHLIRVEG NNLSQYVDDP NTGRQSVVVR        239
Consensus  VVKRCPNHEL .R FNEGQ A P SHLIRVEG N..SQY DP ITGRQSV VR         250 p51B       YEPPQVGTEF TINLYNFMCN SSCVGGMNRR PILIINTLET RDGQVLGRRC        300
p73α       YEPPQVGTEF TIDLYNFMCN SSCVGGMNRR PILIIDTLEH RDGQVLGRRS        289
Consensus  YEPPQVGTEF TI LYNFMCN SSCVGGMNRR PILII TL   RDGQVLGRR.        300 p51B       FERICACPG RDRKADEDSI RHQQVSD-IS IKNQDGTKRP RQNTHGI-Q         347
p73α       FERICACPG RDRKADEDHY RQQALNESS AKNQAASKRA IHQSPPAVPA         339
Consensus  F RICACPG RDRKADED.. RQQ.... S KNQ..KR  Q.......          350 p51B       M-TSIKKRRS RDDELUYLHV RGRETYBHUL KIKESLELHQ YUPQHTIETY        396
p73α       LGAGVKKRRH QDEDTYYLQV RGRBNFEILM KIKESLELME LVPQPLVDSY        389
Consensus  .... KKRR. D... Y  V RGR  B .  KESLELM. .PQ.... Y          400 p51B       RQQQQQQHQH LLQKQTSIQS RSSYQNSSRP UMKHN-SHNK LPSVHQLINP        445
p73α       R-----QQQQ LLQRPSHUQ- IRSSYQPVLSP HNKVHGQMNK LPSVHQLVGQ        433
Consensus  R.... Q Q  LLQ....Q  RSSYQ...P NK    MNK LPSV QL...        450 p51B       QQRNALTPTT IPDGHQANIP HHGTHMPAG DHNGLSPTQA LPPPISHPST         495
p73α       PPPHSSAATP NLGPVQPG-- MLNHHGHAVP ANGEHSSSH- --SAQSHVSG         478
Consensus  .......TT. .... Q   . M..H    ........ S. ..... SH S         500 p51B       SHCTPPPPYP TDKSIVQFLA RLGQSSQLQY FTHQGUTTIY QIEHYSHQQL        545
p73α       SHCTPPPPYH AQPSUVSFLT QLGQPHQIRY FTSQGLQSIY HLQNLTIRDL        528
Consensus  SHCTPPPPY. .D.  V FL  LG . .  Y FT QG. IY ........ QL         550 p51B       ASLKIPEQRR HAIWQIUDH RQHHERSSPS HLLRTPSSAS TVSVGSNETR         595
p73α       GALKIPEQYR MTIWQLQQL KQQHQYSTAQ QLLPSSNAAT ISIQQSKELQ         578
Consensus  . LKIPEQ R .TIW Q .. .Q H.S... LL..   . . ISI QS E..         600 p51B       GERVIDAVHF TLRQTISRRP R------DE NDFHFQHDA RRNKQQHIKE         638
p73α       RQRVMBAVHF RVRHTITIPN RGGPGGGRDE RADFQFQLPD CKARMQFIKE         628
Consensus  . RV. AV F . . TIT . R ...... DE . DF F..D ......Q IKE         650 p51B       --EQE--                                                        641
p73α       EFTBAHIH                                                       636
Consensus  .. B B..                                                       658
```

FIG. 12

```
mp51    1 ATGTCGCAGAGCACCCAGACAAGCGAGTTCCTCAGCCCAGAGGTCTTCCAGCATATCTGG    60
p51B    1 ATGTCCCAGAGCACACAGACAAATGAATTCCTCAGTCCAGAGGTTTTCCAGCATATCTGG    60
          *** **** **   ****** *** *************** mp51   61 GATTTTCTGGAACAGCCTATATGCTCAGTACAGCCCATCGAGTTGAACTTTGTGGATGAA   120
p51B   61 GATTTTCTGGAACAGCCTATATGTTCAGTTCAGCCCATTGACTTGAACTTTGTGGATGAA   120
          ********************* * ***  ******************* mp51  121 CCTTCCGAAAATGGTGCAACAAACAAGATTGAGATTAGCATGGATTGTATCCGCATGCAA   180
p51B  121 CCATCAGAAGATGGTGCGACAAACAAGATTGAGATTAGCATGGACTGTATCCGCATGCAG   180
            * *** ********************** ************ mp51  181 GACTCAGACCTCAGTGACCCCATGTGGCCACAGTACACGAACCTGGGGCTCCTGAACAGC   240
p51B  181 GACTCGGACCTGAGTGACCCCATGTGGCCACAGTACACGAACCTGGGGCTCCTGAACAGC   240
          *** * ********************************************** mp51  241 ATGGACCAGCAGATTCAGAACGGCTCCTCGTCCACCAGCCCCTACAACACAGACCACGCA   300
p51B  241 ATGGACCAGCAGATTCAGAACGGCTCCTCGTCCACCAGTCCCTATAACACAGACCACGCG   300
          ************************************ * ************ mp51  301 CAGAATAGCGTGACGGCGCCCTCGCCCTATGCACAGCCCAGCTCCACCTTTGATGCCCTC   360
p51B  301 CAGAACAGCGTCACGGCGCCCTCGCCCTACGCACAGCCCAGCTCCACCTTCGATGCTCTC   360
          *** * ************* *************** * * mp51  361 TCTCCATCCCCTGCCATTCCCTCCAACACAGATTACCCGGGCCCACACAGCTTCGATGTG   420
p51B  361 TCTCCATCACCCGCCATCCCCTCCAACACCGACTACCCAGGCCCGCACAGTTTCGACGTG   420
          ******  *** *******  *** * * * * mp51  421 TCCTTCCAGCAGTCAAGCACTGCCAAGTCAGCCACCTGGACGTATTCCACCGAACTGAAG   480
p51B  421 TCCTTCCAGCAGTCGAGCACCGCCAAGTCGGCCACCTGGACGTATTCCACTGAACTGAAG   480
          ************ * **** **************** ******* mp51  481 AAGCTGTACTGCCAGATTGCGAAGACATGCCCCATCCAGATCAAGGTGATGACCCCACCC   540
p51B  481 AAACTCTACTGCCAAATTGCAAAGACATGCCCCATCCAGATCAAGGTGATGACCCCACCT   540
            ****** * ************************************ mp51  541 CCACAGGGCGCTGTTATCCGTGCCATGCCTGTCTACAAGAAAGCTGAGCATGTCACCGAG   600
p51B  541 CCTCAGGGAGCTGTTATCCGCGCCATGCCTGTCTACAAAAAAGCTGAGCACGTCACGGAG   600
           * ******* ************* ******* * * mp51  601 GTTGTGAAACGATGCCCTAACCATGAGCTGAGCCGTGAGTTCAATGAGGGACAGATTGCC   660
p51B  601 GTGGTGAAGCGGTGCCCCAACCATGAGCTGAGCCGTGAATTCAACGAGGGACAGATTGCC   660
           *  *** **************** * ************* mp51  661 CCTCCCAGTCATCTGATTCGAGTAGAAGGGAACAGCCATGCCCAGTATGTAGAAGATCCT   720
p51B  661 CCTCCTAGTCATTTGATTCGAGTAGAGGGGAACAGCCATGCCCAGTATGTAGAAGATCCC   720
          *** ** ********* ***************************** mp51  721 ATCACGGGAAGGCAGAGCGTGCTGGTCCCTTATGAGCCACCACAGGTTGGCACTGAATTC   780
p51B  721 ATCACAGGAAGACAGAGTGTGCTGGTACCTTATGAGCCACCCCAGGTTGGCACTGAATTC   780
          ***** ***** ***** ******** ************** *****************
```

FIG. 13

```
mp51   781 ACAACAGTCCTGTACAATTTCATGTGTAACAGCAGCTGCGTCGGAGGAATGAACAGACGT  840
p51B   781 ACGACAGTCTTGTACAATTTCATGTGTAACAGCAGTTGTGTTGGAGGGATGAACCGCCGT  840
            ** *******************   * **** * *** mp51   841 CCAATTTTAATCATCGTTACTCTGGAAACCAGAGATGGGCAAGTCCTGGGCCGACGGTGC  900
p51B   841 CCAATTTTAATCATTGTTACTCTGGAAACCAGAGATGGGCAAGTCCTGGGCCGACGCTGC  900
           ************ ************************************* * mp51   901 TTTGAGGCCCGGATCTGTGCTTGCCCAGGAAGAGACCGGAAGGCAGATGAAGACAGCATC  960
p51B   901 TTTGAGGCCCGGATCTGTGCTTGCCCAGGAAGAGACAGGAAGGCGGATGAAGATAGCATC  960
           ********************************** *** **** *** mp51   961 AGAAAGCAGCAAGTATCGGACAGCGCAAAGAACGGCGATGGTACGAAGCGCCCTTTCCGT 1020
p51B   961 AGAAAGCAGCAAGTTTCGGACAGTACAAAGAACGGTGATGGTACGAAGCGCCCGTTTCGT 1020
           ************ *** ******** ************* * *** mp51  1021 CAGAATACACACGGAATCCAGATGACTTCCATCAAGAAACGGAGATCCCCAGATGATGAG 1080
p51B  1021 CAGAACACACATGGTATCCAGATGACATCCATCAAGAAACGAAGATCCCCAGATGATGAA 1080
           *** *  ******** ******************************** mp51  1081 CTGCTGTACCTACCAGTGAGAGGTCGTGAGACGTACGAGATGTTGCTGAAGATCAAAGAG 1140
p51B  1081 CTGTTATACTTACCAGTGAGGGGCCGTGAGACTTATGAAATGCTGTTGAAGATCAAAGAG 1140
           *** * * ******  ******  *  ***************** mp51  1141 TCACTGGAGCTCATGCAGTACCTCCCTCAGCACACGATCGAAACGTACAGGCAGCAGCAG 1200
p51B  1141 TCCCTGGAACTCATGCAGTACCTTCCTCAGCACACAATTGAAACGTACAGGCAACAGCAA 1200
            * ********** *******  *********** *** mp51  1201 CAGCAGCAGCACCAGCACCTACTTCAGAAACAGACCTCGATGCAGTCTCAGTCTTCATAT 1260
p51B  1201 CAGCAGCAGCACCAGCACTTACTTCAGAAACAGACCTCAATACAGTCTCCATCTTCATAT 1260
           **************** ***************  ***** ******* mp51  1261 GGCAACAGTTCCCCACCTCTGAACAAAATGAACAGCATGAACAAGCTGCCTTCCGTGAGC 1320
p51B  1261 GGTAACAGCTCCCCACCTCTGAACAAAATGAACAGCATGAACAAGCTGCCTTCTGTGAGC 1320
            * **************** ******************* **** mp51  1321 CAGCTTATCAACCCACAGCAGCGCAATGCCCTCACTCCCACCACCATGCCTGAGGGCATG 1380
p51B  1321 CAGCTTATCAACCCTCAGCAGCGCAACGCCCTCACTCCTACAACCATTCCTGATGGCATG 1380
           ************ ****** *******  *** *  **** mp51  1381 GGAGCCAACATTCCTATGATGGGCACTCACATGCCAATGGCTGGAGACATGAATGGACTC 1440
p51B  1381 GGAGCCAACATTCCCATGATGGGCACCCACATGCCAATGGCTGGAGACATGAATGGACTC 1440
           ************ ****** ******************************** mp51  1441 AGCCCTACCCAAGCTCTCCCTCCTCCACTCTCCATGCCCTCCACCTCCCACTGCACCCCA 1500
p51B  1441 AGCCCCACCCAGGCACTCCCTCCCCACTCTCCATGCCATCCACCTCCCACTGCACACCC 1500
           ***   **** *********  *************** * mp51  1501 CCACCGCCCTACCCCACAGACTGCAGCATTGTCAGTTTCTTAGCAAGGTTGGGCTGCTCA 1560
p51B  1501 CCACCTCCGTATCCCACAGATTGCAGCATTGTCAGTTTCTTAGCGAGGTTGGGCTGTTCA 1560
           ***** ** ** ******** *********************** *********** ***
```

FIG. 14

```
mp51  1561 TCATGCCTGGACTATTTCACGACCCAGGGGCTGACCACCATCTATCAGATTGAGCATTAC 1620
p51B  1561 TCATGTCTGGACTATTTCACGACCCAGGGGCTGACCACCATCTATCAGATTGAGCATTAC 1620
           *** **************************************************** mp51  1621 TCCATGGATGATTTGGCAAGTCTGAAGATCCCTGAACAGTTCCGACATGCCATCTGGAAG 1680
p51B  1621 TCCATGGATGATCTGGCAAGTCTGAAAATCCCTGAGCAATTTCGACATGCGATCTGGAAG 1680
           ********** ********* ****   *** ******* mp51  1681 GGCATCCTGGACCACAGGCAGCTGCACGACTTCTCCTCACCTCCTCATCTCCTGAGGACC 1740
p51B  1681 GGCATCCTGGACCACCGGCAGCTCCACGAATTCTCCTCCCCTTCTCATCTCCTGCGGACC 1740
           ************* *** * **** * ********* ** mp51  1741 CCAAGTGGTGCCTCTACCGTCAGTGTGGGCTCCAGTGAGACCCGTGGTGAACGTGTGATC 1800
p51B  1741 CCAAGCAGTGCCTCTACAGTCAGTGTGGGCTCCAGTGAGACCCGGGGTGAGCGTGTTATT 1800
           *** ******* ********************** * * mp51  1801 GATGCCGTGCGCTTTACCCTCCGCCAGACCATCTCTTTTCCACCCCGTGACGAGTGGAAT 1860
p51B  1801 GATGCTGTGCGATTCACCCTCCGCCAGACCATCTCTTTCCCACCCCGAGATGAGTGGAAT 1860
           *** *  ********************* ****  ******** mp51  1861 GATTTCAACTTTGACATGGATTCTCGTCGCAACAAGCAGCAGCGTATCAAAGAGGAAGGA 1920
p51B  1861 GACTTCAACTTTGACATGGATGCTCGCCGCAATAAGCAACAGCGCATCAAAGAGGAGGGG 1920
            **************  * * * ****** mp51  1921 GAA 1923
p51B  1921 GAG 1923
           **
```

FIG. 15

```
mp51BnAA  MSQSTQTSEFLSPEVFQHIWDFLEQPICSVQPIELNFVDEPSENGATNKIEISMDCIRMQ  60
p51B  aa  MSQSTQTNEFLSPEVFQHIWDFLEQPICSVQPIDLNFVDEPSEDGATNKIEISMDCIRMQ  60
          ***** ********************.*** ***************** mp51BnAA  DSDLSDPMWPQYTNLGLLNSMDQQIQNGSSSTSPYNTDHAQNSVTAPSPYAQPSSTFDAL  120
p51B  aa  DSDLSDPMWPQYTNLGLLNSMDQQIQNGSSSTSPYNTDHAQNSVTAPSPYAQPSSTFDAL  120
          ************************************************************ mp51BnAA  SPSPAIPSNTDYPGPHSFDVSFQQSSTAKSATWTYSTELKKLYCQIAKTCPIQIKVMTPP  180
p51B  aa  SPSPAIPSNTDYPGPHSFDVSFQQSSTAKSATWTYSTELKKLYCQIAKTCPIQIKVMTPP  180
          ************************************************************ mp51BnAA  PQGAVIRAMPVYKKAEHVTEVVKRCPNHELSREFNEGQIAPPSHLIRVEGNSHAQYVEDP  240
p51B  aa  PQGAVIRAMPVYKKAEHVTEVVKRCPNHELSREFNEGQIAPPSHLIRVEGNSHAQYVEDP  240
          ************************************************************ mp51BnAA  ITGRQSVLVPYEPPQVGTEFTTVLYNFMCNSSCVGGMNRRPILIIVTLETRDGQVLGRRC  300
p51B  aa  ITGRQSVLVPYEPPQVGTEFTTVLYNFMCNSSCVGGMNRRPILIIVTLETRDGQVLGRRC  300
          ************************************************************ mp51BnAA  FEARICACPGRDRKADEDSIRKQQVSDSAKNGDGTKRPFRQNTEGIQMTSIKKRRSPDDE  360
p51B  aa  FEARICACPGRDRKADEDSIRKQQVSDSTKNGDGTKRPFRQNTEGIQMTSIKKRRSPDDE  360
          *************************.****************************** mp51BnAA  LLYLPVRGRETYEMLLKIKESLELMQYLPQHTIETYRQQQQQQHQHLLQKQTSMQSQSSY  420
p51B  aa  LLYLPVRGRETYEMLLKIKESLELMQYLPQHTIETYRQQQQQQHQHLLQKQTSIQSPSSY  420
          ***************************************************. *** mp51BnAA  GNSSPPLNKMNSMNKLPSVSQLINPQQRNALTPTTMPEGMGANIPMMGTHMPMAGDMNGL  480
p51B  aa  GNSSPPLNKMNSMNKLPSVSQLINPQQRNALTPTTIPDGMGANIPMMGTHMPMAGDMNGL  480
          ***********************************.*.********************** mp51BnAA  SPTQALPPPLSMPSTSHCTPPPPYPTDCSIVSFLARLGCSSCLDYFTTQGLTTIYQIEHY  540
p51B  aa  SPTQALPPPLSMPSTSHCTPPPPYPTDCSIVSFLARLGCSSCLDYFTTQGLTTIYQIEHY  540
          ************************************************************ mp51BnAA  SMDDLASLKIPEQFRHAIWKGILDHRQLHDFSSPPHLLRTPSGASTVSVGSSETRGERVI  600
p51B  aa  SMDDLASLKIPEQFRHAIWKGILDHRQLHEFSSPSHLLRTPSSASTVSVGSSETRGERVI  600
          ***************************..**.*************** mp51BnAA  DAVRFTLRQTISFPPRDEWNDFNFDMDSRRNKQQRIKEEGE  641
p51B  aa  DAVRFTLRQTISFPPRDEWNDFNFDMDARRNKQQRIKEEGE  641
          ***************************.************
```

HUMAN P51 GENES AND GENE PRODUCTS THEREOF

CROSS REFERENCE TO RELATED APPLICATIONS

This application is a Divisional of U.S. application Ser. No. 11/340,715, filed Jan. 27, 2006, which is a Divisional of U.S. application Ser. No. 09/670,568, filed Jan. 18, 2001 (U.S. Pat. No. 7,132,276, issued Nov. 7, 2006); which is a 371 of PCT/JP99/01512, filed Mar. 24, 1999; the disclosure of each of which is incorporated hereby in reference.

TECHNICAL FIELD

The present invention relates to novel human genes. More particularly, the invention relates to a novel human gene analogous to human p53 and human p73 genes, which are known as tumor suppressor genes, and the corresponding gene product.

BACKGROUND ART

The p53 protein was discovered as a nuclear protein binding to the large T antigen of the DNA tumor virus SV40 and its gene (p53 gene) has been cloned. At first, the p53 gene was considered to be an oncogene because the transfer of this gene and the ras gene together into cells resulted in transformation of embryonal cells. Later studies, however, revealed that the initially cloned p53 gene was a mutant type and that the wild type rather suppressed the transforming activity of the mutant type. By now, deletions or anomalies in the p53 gene have been detected in many human cancers and a gamate mutation of the p53 gene was also discovered in Li-Fraumeni syndrome which is known to be a hereditary disease with a high risk for malignant conversion. Because of these and other findings, the p53 gene has by now been considered to be an important suppressor oncogene [Baker, S. J., et al., Science, 244, 217-221 (1989): Nigro, J. M., Nature, 342, 705-708 (1989)].

The human p53 protein consists of 393 amino acid residues and can be roughly divided into the N-terminal domain (the 1~101st amino acid region), the core domain (the 102~292nd amino acid region), and the C-terminal domain (the 293~393rd amino acid region). The N-terminal domain contains sequences necessary for transcriptional regulation, such as acidic amino acids and a high-proline region, and is considered to be a transcriptional activator domain. The central core domain contains 3 hydrophobic sites and is a domain associated with nucleotide sequence-specific DNA binding. The C-terminal domain contains many basic amino acids and a sequence necessary for tetramerization and is considered to be responsible for recognition of nonspecific DNA binding and DNA damage and inhibition of transformation.

Many of the p53 gene abnormalities detected in human cancer cells are missense mutations and most of them are concentrated in the core domain corresponding to the 100~300th amino acid sequence from the N terminus, particularly in the region called "hot-spot" which has been conserved among species. The hot-spot region in the core domain is the sequence associated with the binding between p53 protein and DNA and, actually, mutation of this region results in the inhibition of specific binding to DNA.

It became clear from the above that the p53 protein plays the role of a transcriptional control factor which binds specifically to other genes to modulate expression of the genes.

The gene whose transcription is induced by the p53 protein includes, among others, the p21 gene [known as WAF1, CIP1, or SDI1 (EI-Dairy, W. S., et al., Cell, 75, 817 (1993)); MDM2 (Wu. X., et al., Genes Dev., 7, 1126 (1993)); MCK (Weintraub. H., et al., Proc. Natl. Acad. Sci. USA, 88, 4570 (1991): Zambetti. G. P., et al., Genes Dev., 6, 1143 (1992))], GADD45 [Kastan, M. B., et al., Cell, 71, 587 (1992)], Cyclin G [Cyclin G: Okamoto, K., EMBO J., 13, 4816 (1994)], BAX [Miyashita, T., et al., Cell, 80, 293 (1995)], and insulin-like growth factor-binding protein 3 [IGF-BP3: Buckbinder, L., et al., Nature, 377, 646 (1995)].

The protein encoded by the p21 gene is an inhibitor protein for cyclin-dependent kinase (CDK), and it has been found that the wild type p53 protein regulates the cell cycle in an inhibitory way through p21 [Harper, J. W., et al., Cell, 75, 805 (1993): Xiong, Y., et al., Nature, 366, 707 (1993): Gu, Y., et al., Nature, 366, 701 (1993)]. Furthermore, the p21 gene reportedly binds to the proliferating cell nuclear antigen (PCNA) to directly inhibit DNA replication [Waga, S., et al., Nature, 369, 574 (1994)]. In addition, the p21 gene has been found to the same gene as the SDI1 gene which induces senescence of cells to inhibit DNA synthesis [Noda., A., et al., Exp. Cell Res., 211, 90 (1994)].

MDM2 binds to the p53 protein to inactivate the transcriptional regulation activity of the gene protein, leading to the putative conclusion that MDM2 is acting as a negative feedback regulating factor.

IGF-BP3 is a negative regulating factor in IGF signalization. Therefore, the increase of the IGF-BP3 gene by the p53 protein suggests the possible outcome that the p53 protein induces suppression of growth of IGF-dependent cells.

Meanwhile, the wild type p53 protein reportedly induces apoptosis of myelocytic leukemia cells [Yonish-Rouach, E., et al., Nature, 352, 345 (1991)]. Induction of thymocyte apoptosis by irradiation does not take place in p53-defective mice [Lowe, S. W., Nature, 362, 847 (1993): Clarke, A. R., et al., Nature 362, 849 (1993)] and, in the crystalline lens, retina and brain, the p53 protein induces apoptic death of cells deprived of normal retinal blastoma gene (RB gene) activity [Pan, H., and Griep, A. E., Genes Dev., 8, 1285 (1994): Morgenbesser, S. D., et al., Nature 371, 72 (1994): Howes, K. A., Genes Dev., 8, 1300 (1994): Symonds, H., et al., Cell, 78, 703 (1994)]. E. White proposes that the p53 protein is useful for a surveillance of RB gene mutation and that the protein is likely to induce apoptosis of the cells in which a RB gene mutation is involved [White, E., Nature, 371, 21 (1994)].

Furthermore, in the mouse erythroid leukemia cell line in which the temperature-sensitive p53 gene only is expressed, a fall in temperature results in reconversion of the mutant p53 gene to the wild type to induce apoptosis and the mutant p53 gene isolated therefrom imparts the ability to grow in soft agar medium to a p53-defective fibroblast line (impart anchorage independence) [Xu et al., Jpn, J. Cancer Res. 86: 284-291 (1995); Kato et al., Int. J. Oncol. 9: 269-277].

BAX is able to bind to bcl-2, which is an inhibitor of apoptosis, and encourages apoptic cell death [Oltvai, Z. M., et al., Cell, 74, 609 (1993)]. The increase in the BAX gene and decrease in bcl-2 by the p53 protein are involved in the apoptosis of the mouse leukemia cell line M1 [Miyashita, T., et al., Oncogene, 9, 1799 (1994)] and Fas, which is one of the signal transducers for apoptosis, is increased in non-small-cell lung cancer and erythroleukemia [Owen-Schaub, L. B., et al., Mol. Cell. Biol., 15, 3032 (1995)].

The many investigations referred to above have revealed that the p53 protein either activates or represses the transcription of various genes not limited to the p21 gene. Moreover, even the mutant p53 protein defected in the transcriptional regulating function is capable of interacting with other intracellular proteins to transmit signals and discharge a DNA damage repairing function.

Among the functions of the p53 protein which have so far been identified are a transcription regulating function, a signal transducer function through binding to other intracellular proteins, a constituent element of a protein complex related to DNA replication, a DNA binding function, and exonuclease activity, and it is conjectured to be the result of a compound interplay of these functions that causes the arrest of the cell cycle in cells, induction of apoptosis, DNA repair, regulation of DNA replication, and induction of differentiation.

Furthermore, it is not true that the functions of the p53 protein are expressed only in the event of a gene damage but it is reported that when the living tissue is subjected to various stresses such as viral infection, cytokine stimulation, hypoxia, a change in the nucleotide pool, drug-induced metabolic abnormality, etc., the stimuli trigger quantitative or qualitative changes in the p53 protein. The p53 protein subjected to the quantitative or qualitative regulation expresses its functions, such as signal transduction through interactions with other proteins and control of the transcription of other genes, to regulate the replication of DNA in cells of the living tissue subjected to biological stresses, repair the cells by suspending the cell cycle, eliminate cells by way of apoptosis, or promote the differentiation of cells, thereby contributing to the protection of the living tissue against the stresses [Ganman, C. E., et al., Genes Dev., 9, 600-611 (1995): Graeber, T. G., et al., Nature, 379, 88-91 (1996): Linke, S. P., et al., Genes Dev., 10, 934-947 (1996): Xiang, H., et al., J. Neurosci., 16, 6753-6765 (1996)].

In view of the existence of p53 gene mutations in a half of human tumors, clinical application of the p53 gene and its product protein to the diagnosis and therapy of tumors has been a subject of study in recent years. The method of detecting tumor cells invading the lymph node or body fluid by carrying out a PCR using primers specifically recognizing the mutation site of the p53 gene can be an effective diagnostic technique for estimating the scope of tumor invasion or predicting a recurrence of the tumor [Hayashi, H., et al., Lancet, 345, 1257-1259 (1995)].

Furthermore, taking advantage of the apoptosis-inducing activity of the p53 protein, a gene therapy comprising introducing a wild type p53 gene into the tumor cell by means of a virus vector is being practiced in the United States and its effectiveness has been reported [Roth, J. A., et al., Nature Med., 2, 985-991 (1996)]. Recently, in Japan, too, this gene therapy has been started in several locations.

Meanwhile, more than the majority of human tumors are not associated with p53 gene mutation and, from this fact, the possibility of existence of other tumorigenesis-inhibitory proteins analogous to the p53 protein has been pointed out.

The inventors of the present invention previously found that a p53 gene mutation cannot be a useful premonitory indicator of non-Hodgkin's lymphoma (NHL).

Recently, a novel gene, named p73, which has high homology to said p53 gene has been identified [Kaghad, M., et al., Cell, 90, 809-819 (1997)]. According to the information available to the present inventors, the p73 protein shows 29% homology to the human p53 protein in the transcriptional activator domain (the 1st~45th amino acid region). Moreover, this p73 protein has a homology of 63% in the DNA binding domain (the 113rd~290th amino acid region) having 6 complementary conserved sequences called hot spots of mutation; and a homology of 38% in the oligomerization domain (the 319th~363rd amino acid region). With regard to the C-terminal domain, however, no significant homology has been recognized between p73 protein and p53 protein.

It is reported that excessive expression of the p73 protein inhibits the growth of a neuroblastoma cell line and SAOS2 cells (an osteosarcoma cell line) and that a transient expression of the p73 protein promotes the apoptosis of SAOS2 cells and baby hamster's kidney cells [Bruce Clurman and Mark Groudine, Nature, 389, 122-123 (1997): Christine, A., et al., Nature, 389, 191-194 (1997)].

However, the p73 protein is somewhat different from the p53 protein in that the former is expressed only at low levels in normal tissues. Moreover, the p73 protein is different from the p53 protein in that the expression of the former protein in a neuroblastoma cell line is not induced by UV irradiation or a low dose of actinomycin D.

Therefore, it is not true that the p73 protein has the exactly the same functions as those of the p53 protein and, at the present, much depends on further research. There is a report arguing that, based on the observations so far made, this p73 may be categorized as a putative tumor suppressive factor in neuroblastoma.

The present invention has for its object to provide information on a novel gene and gene product related to the morphogenesis of human tumors. More particularly, the object of the present invention is to provide a novel gene analogous to the p53 gene which, as mentioned above, is already known as a tumor suppressor gene and the corresponding gene product.

It is a further object of the present invention to provide primers and probes each comprising a partial DNA of said gene, vectors harboring said gene, transformants as transformed using any of said vectors, and a method of producing said gene product which comprises growing any of said transformants.

BRIEF DESCRIPTION OF THE DRAWINGS

FIG. 2 is a diagram showing the homology relationship of the amino acid sequence encoded by the human p51A gene (SEQ ID NO:1), the amino acid sequence of the p53 protein (SEQ ID NO:3), and the amino acid sequence of the p73β protein (SEQ ID NO:6). The amino acids which are common among the three sequences are indicated in blocks. The consensus sequence is SEQ ID NO:7.

FIG. 3 is a diagram showing the homology relationship of the amino acid sequence encoded by the human p51B gene (SEQ ID NO:4) and the amino acid sequence of the p73α protein (SEQ ID NO:8). The amino acids which are common to both sequences are indicated in blocks. The consensus sequence is SEQ ID NO:9.

Figure 1:
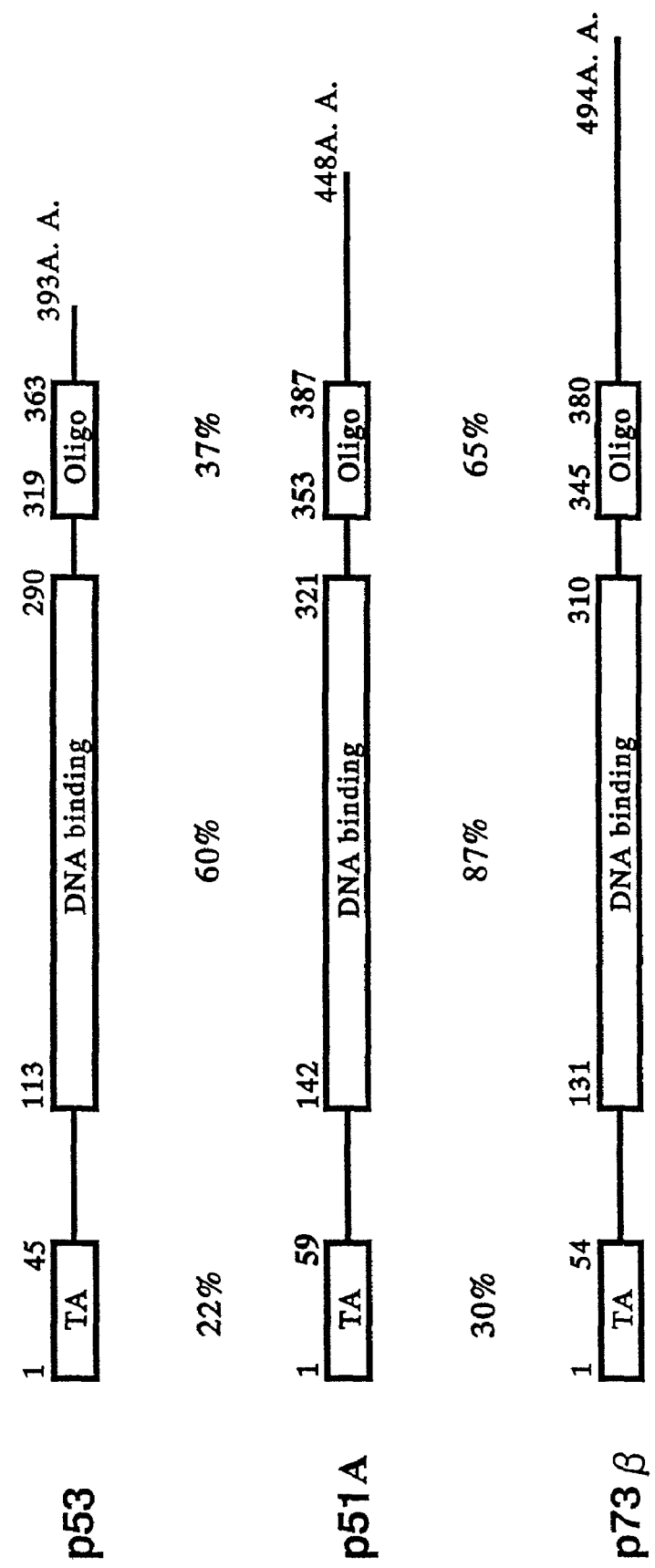
FIG. 1 is a diagram illustrating features of the structural domains of the p51A protein, along with those of the p53 protein and p73β protein. In the diagram, "TA" represents a transcriptional activator domain; "DNA binding" represents a DNA binding domain; and "Oligo" represents an oligomerization domain.

In the diagram, the "1-2-3 cells" represents control cells into which the vector only has been introduced and not containing the p51A gene and the "1C1 cells" or "4B1 cells" represents the p51A-containing 1-2-3 cells as transformed with the expression vector harboring the p51A gene (pRc-CMV/p51A). The "λ/Hind III" represents digestion products as digested with the λ phage DNA restriction enzyme Hind III and are DNA size markers (product of New England Biolabs. Ind.). The "100 bp ladder" represents size markers comprising DNA fragments having sizes corresponding to multiples of 100 bp (product of GIBCO-BRL).

FIGS. 12~14 show a diagram comparing the nucleotide sequence (bottom row) of the coding region of the human p51B gene (SEQ ID NO:5) with the corresponding sequence (upper row) of the mouse homolog (mouse p51B gene; SEQ ID NO:10)). The nucleotides common between the two sequences are indicated by the asterisk mark in the diagram.

FIG. 15 is a diagram comparing the amino acid sequences of the human p51B protein (SEQ ID NO:4) and mouse p51B protein (SEQ ID NO: 11) encoded by the human p51B gene and mouse p51B gene, both shown in FIGS. 12~14, respectively. The amino acids common to both sequences are indicated by the asterisk mark in the diagram.

DISCLOSURE OF INVENTION

Since more than the majority of human tumor tissues have mutants of the p53 gene which is an oncogene suppressor gene as mentioned above, the possibility has been suggested of the existence of other gene products (proteins) than the p53 protein which are discharging the tumorigenesis-inhibiting function.

Therefore, the inventors of the present invention did intensive investigations in search for novel genes and gene products which might be associated with said tumorigenesis-inhibiting function. As a result, they discovered a novel human-derived gene coding for a protein showing activity similar to that of said p53 protein and confirmed that the particular gene or gene product is significantly associated with apoptosis. The present invention has its basis in this new finding.

The present invention, therefore, is directed to the following human p51 genes 1~8 and the related genes.

1. A gene coding for the following protein (a) or (b):
(a) a protein having the amino acid sequence shown under SEQ ID NO:1
(b) a protein having an amino acid sequence derived from the amino acid sequence shown under SEQ ID NO:1 by deletion, substitution or addition of one or a plurality of amino acids and having p51 activity.

2. A gene comprising the following DNA (a) or (b):
(a) a DNA having a nucleotide sequence identified by the nucleotide numbers 145~1488 of the nucleotide sequence shown under SEQ ID NO:2
(b) a DNA capable of hybridizing with the DNA having a nucleotide sequence identified by the nucleotide numbers 145~1488 of the nucleotide sequence shown under SEQ ID NO:2 under stringent conditions and coding for a protein having p51 activity.

3. A gene as defined in paragraph 2 which has the nucleotide sequence shown under SEQ ID NO:2.

4. A cDNA comprising the following DNA (a) or (B):
(a) a DNA having a nucleotide sequence identified by the nucleotide numbers 145~1488 of the nucleotide sequence shown under SEQ ID NO:2
(b) a DNA capable of hybridizing with a DNA having a nucleotide sequence identified by the nucleotide numbers 145~1488 of the nucleotide sequence of SEQ ID NO:2 under stringent conditions and coding for a protein having p51 activity.

5. A DNA characterized in that it is capable of hybridizing with the nucleotide sequence of SEQ ID NO:2 under stringent conditions.

6. A DNA characterized in that it is capable of the hybridizing with a nucleotide sequence identified by the nucleotide numbers 145~1488 of SEQ ID NO:2 under stringent conditions.

7. The DNA defined in paragraph 5 for use as a primer.

8. The DNA defined in paragraph 5 for use as a probe.

The present invention is further directed to the following human p51 proteins 9~14 and the related proteins or peptides.

9. A protein defined under (a) or (b) below:
(a) a protein having the amino acid sequence shown under SEQ ID NO:1
(b) a protein having an amino acid sequence derived from the amino acid sequence of SEQ ID NO:1 by deletion, substitution or addition of one or a plurality of amino acids and having p51 activity.

10. A protein as defined in paragraph 9 at least containing the amino acid sequences identified by the amino acid numbers 1~59, amino acid numbers 142~321, and amino acid numbers 359~397 of the amino acid sequence shown under SEQ ID NO:1.

11. A polypeptide having an amino acid sequence, in SEQ ID NO:1, which has at least one function selected from the group consisting of transcriptional activation function, DNA binding function and oligomerization function.

12. A polypeptide as defined under (a) or (b) below:
(a) a polypeptide having an amino acid sequence identified by the amino acid numbers 1~59 of SEQ ID NO:1
(b) a polypeptide having an amino acid sequence derived from the amino acid sequence defined under (a) by deletion, substitution or addition of one or a plurality of amino acids and having a transcriptional activation function.

13. A polypeptide as defined under (a) or (b) below:
(a) a polypeptide having an amino acid sequence identified by the amino acid numbers 142~321 of SEQ ID NO:1
(b) a polypeptide having an amino acid sequence derived from the amino acid sequence defined under (a) by deletion, substitution or addition of one or a plurality of amino acids and having a DNA binding function.

14. A polypeptide as defined under (a) or (b) below:
(a) a polypeptide having an amino acid sequence identified by the amino acid numbers 359~397 of SEQ ID NO:1
(b) a polypeptide having an amino acid sequence derived from the amino acid sequence defined under (a) by deletion, substitution or addition of one or a plurality of amino acids and having an oligomerization function.

The present invention is further directed to a vector harboring said p51 gene, host cells transformed with said vector, and a method of producing the p51 protein characterized by growing said host cells in a medium and harvesting the protein from the resulting culture.

It should be understood that the designation of p51 is used only for convenience's sake in this specification and is by no means definitive of the gene and gene product (protein) of the present invention.

Furthermore, the term "gene (DNA)" in the context of the present invention means not only a double-stranded DNA but also a single-stranded DNA, inclusive of the component sense chain and antisense chain, and is by no means limitative of its length. Therefore, unless otherwise indicated, the gene (DNA) of the present invention includes the double-stranded DNA inclusive of human genomic DNA, a single-stranded DNA comprising the cDNA (sense chain), a single-stranded DNA having a sequence complementary to said sense chain (antisense chain), and all fragments thereof.

The representation of amino acids, peptides, nucleotide sequences, nucleic acids, etc. by abbreviations in this specification confirms to the recommendations by IUPAC-IUB, the "Guidelines for Preparation of Specifications Etc. which contain Nucleotide Sequences or Amino Acid Sequences" (the Japanese, United States of America and European Trinity Patent Office), and the conventions in the use of symbols in the related field of art.

(1) The p51 Gene and its Equivalent

The present invention relates to novel human genes coding for proteins having actions or functions identical or equivalent to the actions or functions of the p53 protein.

The gene according to the present invention has been acquired by carrying out a PCR using primers newly established after energetic explorations using specific regions selected from the sequences of the hitherto-known p53 gene and p73 gene with judicious endeavors.

More particularly, by carrying out a PCR using the novel primers described in Examples which appear hereinafter, a gene fragment which is not identical but similar to the p53 gene and p73 gene was obtained. By using this DNA fragment as a probe, a cDNA clone coding for a novel protein having high homology to the amino acid sequence of p53 protein was successfully isolated from among cDNA clones randomly selected from a human skeletal muscle cDNA library.

The calculated molecular mass of the amino acid sequence deducted from the cDNA thus obtained was about 50,894 Da and, therefore, the present inventors named this cDNA (DNA) "human p51A gene (or briefly, p51A gene)" and the protein having the amino acid sequence encoded by this gene "p51A protein (or briefly, p51A protein)" for convenience's sake.

Subsequent research revealed that the gene encoded by the p51 cDNA clone has alternative splicing variants. Moreover, an investigation of the pattern of expression and production of the transcripts of the gene in various human tissues revealed that the expression products (proteins) exist as spliced chiefly in a short form and a long form.

Based on the amino acid information deduced from the p51 cDNA splicing variants, the shot-form splicing variant is the gene (p51A gene) coding for the protein having said 448 amino acid sequence (molecular mass ca 50.9 kDa) and the long-form splicing variant is a gene coding for a protein having a 641 amino acid sequence (molecular mass ca 71.9 kDa). In this specification, for convenience's sake, the latter gene is called "human p51B gene (or briefly, p51B gene)" and the protein having the amino acid sequence encoded by said gene "human p51B protein (or briefly, p51B protein)".

Furthermore, in this specification, said p51A gene and p51B gene are collectively referred to as "p51 gene" and the p51A protein and p51B protein are collectively referred to as "p51 protein".

Referring to said splicing variant of the p51 gene, the existence of a plurality of variants inclusive of the gene defective of a part of the TA domain have been confirmed.

An investigation of the expression products of these p51 genes revealed that the p51 gene product (p51 protein) of the present invention shows transcriptional activation activity, cell growth-inhibitory activity and apoptosis-inducing activity which are similar to the activities of the p53 protein. Furthermore, the expression of the p51 gene in human tissues was found to be more tissue-specific than the expression of the p53 gene and, compared with the expression of the p73 gene which is also tissue-specific, was broader in tissue distribution although there was an overlap of expression pattern between them. Moreover, the mutation of the p51 gene was found in the human tumor tissues or tumor cell lines.

The above findings suggested strongly that the human p51 gene of the present invention is a new member of the p53 tumor suppressor gene family.

As a specific example of the p51 gene according to the present invention, there can be mentioned one having the DNA sequence possessed by the clones (p51A, p51B) described in Example 1 which appears hereinafter.

As the gene possessed by the p51A clone, there can be mentioned the gene (1344 nucleotides) coding for the 448-residue protein of SEQ ID NO:1 in the SEQUENCE LISTING which appears hereinafter. Specifically, this is a gene having the nucleotide sequence corresponding to the 145th~1488th nucleotides of SEQ ID NO:2, which corresponds to an open reading frame.

The full-length nucleotide sequence of the p51A cDNA consists of 2816 nucleotides as shown in SEQ ID NO:2. The p51A gene of the present invention includes genes containing this nucleotide sequence shown under SEQ ID NO:2. In the nucleotide sequence shown under SEQ ID NO:2, the initiation codon (ATG) is situated in the 145~147 nucleotide position and the polyadenylation signal (AATAA) is situated in the 2786~2791 position.

The amino acid sequence of the 448-residue p51A protein encoded by the p51A gene is shown under SEQ ID NO:1. As shown, this protein has a transcriptional activation domain corresponding to the amino acid numbers 1~59, a DNA binding domain corresponding to the amino acid numbers 142~321, and an oligomerization domain corresponding to the amino acid numbers 353~397.

The homology of each of said domains of the p51A protein to the corresponding domain of the known proteins p53 or p73 was investigated with FASTA Program using the GCG software (Wisconsin Sequencing Package, Genetics Computer Group) [Person, W. R. and Lipman, D. J., Proc. Natl. Acad. Sci. U.S.A., 85, 1435-1441 (1988)]. The results are shown in Table 1 (cf. FIGS. 1 and 2). For reference, the homologies between p53 protein and p73β protein as determined by the same method are also shown in Table 1.

TABLE 1

| | Full-length sequence | Transcription activation domain | DNA binding domain | Oligomerization domain |
|---|---|---|---|---|
| p51A ↔ p53 | 36% | 22% | 60% | 37% |
| p51A ↔ P73β | 42% | 30% | 87% | 65% |
| p53 ↔ p73 | 28% | 27% | 63% | 83% |

On the other hand, as the gene possessed by the p51B clone, there can be mentioned a gene (1923 nucleotides) coding for the 641-residue protein shown under SEQ ID NO:4 in the SEQUENCE LISTING given hereinafter. Specifically, this is a gene having the nucleotide sequence identified by the nucleotide numbers 145~2067 of SEQ ID NO:5, which corresponds to an open reading frame.

The full-length nucleotide sequence of this p51B cDNA consists of 2270 nucleotides as shown under SEQ ID NO:5. The p51B gene according to the present invention includes genes containing the nucleotide sequence shown under SEQ ID NO:5.

The amino acid sequence of the 641-residue p51B protein encoded by the p51B gene is shown under SEQ ID NO:4. This protein has a transcriptional activation domain corresponding to the amino acid numbers 1~59, a DNA binding domain corresponding to the amino acid numbers 142~321, and an oligomerization domain corresponding to the amino acid numbers 353~397. In addition, there is an additional sequence (SAM domain) in the C-terminal region, although the corresponding amino acid numbers cannot be identified. In this specification, the region of amino acid numbers 353~641 inclusive of this SAM domain is regarded as an oligomerization domain in a broad sense.

As in the case of the p51A protein, the homology of the amino acid sequence of each of said domains of the p51B protein to the sequence of the corresponding domain of the known protein p73α was investigated with FASTA PROGRAM using GCG software. The results are shown in FIG. 3. In FIG. 3, the boxed parts are amino acid sequences common to the p51B protein and p73α protein. It is, therefore, clear that the amino acid sequence of the p51B protein according to the present invention is homologous to the sequence of the p73α protein over a broad range.

Thus, the p51 gene according to the present invention includes a human p51A gene having a nucleotide sequence coding for a protein having the amino acid sequence shown under SEQ ID NO:1 and a human p51B gene having a nucleotide sequence coding for a protein having the amino acid sequence shown under SEQ ID NO:4. However, the p51 gene of the invention is not limited to those genes but includes all homologs of those human p51 genes.

The term "homolog of human p51 gene" means any member of a group of interrelated genes which are analogous to said p51A gene or p51B gene in the nucleotide sequence and/or structural features and gene expression pattern or analogous to each other in the biological functions of their own and gene products (proteins) and, as such, may be regarded as constituting one gene family. In this sense, splicing variants and alleles of the human p51 gene are, of course, subsumed in the concept of said "homolog".

As an example of said homolog, there can be mentioned a gene which codes for a protein having an amino acid sequence resulting from the mutation or modification of one or a plurality of sites of the amino acid sequence shown under SEQ ID NO:1 and having actions or functions similar to those of said p51A protein having the amino acid sequence shown under SEQ ID NO:1. The preferred is a gene coding for an amino acid sequence retaining at least a given degree of homology to the amino acid sequence shown under SEQ ID NO:1.

The degree of homology in amino acid sequence may generally be not less than about 45%, preferably not less than about 50%, in terms of the full-length sequence as determined with FASTA PROGRAM using said GCG software. Preferably, the homology should be not less than a given value in at least one of the transcriptional activation domain, DNA binding domain and oligomerization domain. For example, the homology in the transcriptional activation domain may be about 35% or higher, preferably not less than 45%, the homology in the DNA binding domain may be 88% or higher, preferably not less than about 90%, and the homology in the oligomerization domain may be about 70% or higher, preferably not less than about 80%.

Thus, the gene of the present invention includes any gene having a nucleotide sequence coding for a protein having an amino acid sequence derived from the sequence of SEQ ID NO:1 by deletion, substitution or addition of one~a few or a plurality of amino acids on condition that the above-mentioned qualifications are satisfied.

The extent of "deletion, substitution or addition of amino acids" and the site or sites involved are not particularly restricted inasmuch as the protein so modified is functionally equivalent to the protein (p51A protein or p51B protein) having the amino acid sequence of SEQ ID NO: 1 or 4. Thus, the term "p51 activity" as used in this specification means the activities and functions possessed by the p51 protein, represented by p51A protein or p51B protein, of the present invention, thus including tumor cell growth inhibitory activity, apoptosis-inducing activity and transcriptional regulation function in cells, among others.

The p51 protein of the present invention is considered to have actions similar to those of the p53 protein which is known to be a cell proliferation inhibitory factor. Therefore, the term "p51 activity" as used in this specification referring to the actions and functions of the p51 protein may be restated in the same terms as applied to the known activities and functional features of the p53 protein.

As the actions and functions of the p53 protein, there may be mentioned a transcriptional regulation function, a signal transduction function which is expressed through its binding to other intracellular proteins, the function as a component of the protein complex related to DNA replication, a DNA binding function, exonuclease activity, etc., and as the functions expressed by the composite interplay of said various functions, a cell cycle interrupting function, an apoptosis-inducing function, a DNA repairing function, a DNA replication control function and/or a differentiation-inducing function in cells. It is considered that the p51 protein of the present invention has some or all of these actions and functions.

The modification of an amino acid sequence may be spontaneous, e.g. spontaneous mutation or posttranslational modification, but can be artificially induced on the basis of a native gene.

The present invention encompasses all modified genes coding for proteins having the above-mentioned characteristics of the p51 protein of the invention without regard to the cause or means of mutation or modification.

The means for making such artificial modifications includes genetic engineering techniques such as site-specific (-directed) mutagenesis [Methods in Enzymology, 154: 350, 367-382 (1987); ditto 100: 468 (1983); Nucleic Acids Res., 12: 9441 (1984); Zoku Seikagaku Jikken Koza 1 "Idenshi Kenkyuho II" [Experimental Biochemistry Series 1 "Methods for Gene Research II" (edited by Japanese Biochemical Society), p105 (1986)], etc. and chemical synthetic techniques such as the phosphotriester method and the phosphoamidate method [J. Am. Chem. Soc., 89: 4801 (1967); ditto 91: 3350 (1968); Science, 150: 178 (1968); Tetrahedron Lett., 22: 1859 (1981); ditto 24: 245 (1983)] as well as a suitable combination of such techniques. More specifically, DNA synthesis can be carried out chemically by the phosphoramidite method or the triester method, or on a commercial automatic oligonucleotide synthesizer. The double-stranded chain fragment can be obtained by synthesizing complementary chains and annealing them together under suitable conditions or can be obtained from a chemically synthesized single-stranded chain by adding a complementary chain using a DNA polymerase together with suitable primer sequences.

As specific examples of the gene of the invention, there can be mentioned the gene having a nucleotide sequence corresponding to the nucleotide numbers 145~1488 of the nucleotide sequence shown under SEQ ID NO:2 and the gene having a nucleotide sequence corresponding to the nucleotide numbers 145~2067 of the sequence of SEQ ID NO:5. Each of these nucleotide sequences represents an example of combination of the codons coding for the respective amino acid residues of the amino acid sequence shown under SEQ ID NO:1 or 4. Therefore, the gene of the present invention is not limited to genes having such specific nucleotide sequences but may have nucleotide sequences designed by using a combination of optional codons for each amino acid residue. Selection of codons can be made in the routine manner, for example with reference to the frequency of utilization of each codon by the host to be used [Nucleic Acids Res., 9, 43 (1981)].

Furthermore, as mentioned above, the gene of the present invention includes a nucleotide sequence having a defined degree of homology to the nucleotide sequence corresponding to the nucleotide numbers 145~1488 [hereinafter sometimes referred to briefly as the nucleotide sequence (145-1488)] of the nucleotide sequence shown under SEQ ID NO:2.

As an example of such gene, there can be mentioned a gene having a nucleotide sequence capable of hybridizing with a DNA having said nucleotide sequence (145-1488) under stringent conditions, for example in 0.1% SDS-containing 0.2×SSC at 50° C. or in 0.1% SDS-containing 1×SSC at 60° C.

The gene of the present invention can be easily produced and acquired by the standard genetic engineering techniques [Molecular Cloning 2d Ed, Cold Spring Harbor Lab. Press (1989); Zoku Seikagaku Jikken Koza 1 "Idenshi Kenkyuho I, II, III" [Supplemental Biochemical Experimental Series 1 "Methods for Gene Research I, II, III" (edited by Japanese Biochemical Society), (1986), etc.] based on the sequence information on the specific examples shown in SEQ ID NO:2.

More particularly, the object gene can be acquired by constructing a cDNA library from a suitable source in which the gene of the invention can be expressed and selecting the desired clone from this cDNA library using a suitable probe or antibody specific to the gene of the invention in the per se known manner [Proc. Natl. Acad. Sci., USA., 78: 6613 (1981); Science, 222: 778 (1983), etc.].

In the above procedure, the cDNA source includes but is not limited to various cells or tissues in which the gene of the invention is expressed and cultured cells derived therefrom. Isolation of the whole RNA from such a source, isolation and purification of mRNA, acquisition of cDNA, and cloning thereof can all be carried out in the routine manner. cDNA libraries are also commercially available. In the practice of the present invention, such commercial cDNA libraries, for example those available from Clontech Lab. Inc., can also be employed.

The method of screening for the gene of the invention from a cDNA library is not particularly restricted, either, but the conventional methods can be selectively employed.

To be specific, selection of a cDNA clone by an immunoscreening technique using a specific antibody against the protein produced by the cDNA, the plaque hybridization or colony hybridization technique using a probe having a selective binding affinity for the objective DNA sequence, or a combination thereof can be mentioned by way of example.

As to the probe to be used in the above procedure, it is generally advantageous to use a DNA chemically synthesized according to the nucleotide sequence information on the gene of the present invention but the very gene of the invention which has already been acquired or a fragment thereof can of course be used with advantage as said probe. Furthermore, the sense primer and antisense primer established based on the nucleotide sequence information on the p51 gene of the present invention can be used as the screening probe.

For acquisition of the gene of the invention, DNA/RNA amplification by the PCR method [Science, 230, 1350 (1985)] or a modification thereof can also be used with advantage. Particularly under circumstances where a full-length cDNA can hardly be obtained from a library, the RACE [rapid amplification of cDNA ends] method [Jikken Igaku (Experimental Medicine), 12(6): 35 (1994)], in particular the 5'-RACE method [Frohman, M. A., et al., Proc. Natl. Acad. Sci., USA., 8: 8998 (1988)], can be used with advantage.

The primers for use in such PCR methods can be judiciously established according to the sequence information on the p51 gene of the invention which has been uncovered in accordance with the present invention and can be synthesized by the conventional procedure. Isolation and purification of the amplified DNA or RNA fragment can be carried out by the conventional techniques as mentioned hereinbefore, for example by gel electrophoresis or hybridization.

The nucleotide sequence of the p51 gene of the present invention or any of the various DNA fragments which can be obtained as above can be determined in the routine manner, for example by the dideoxy method [Proc. Natl. Acad. Sci., USA., 74: 5463 (1977)], the Maxam-Gilbert method [Methods in Enzymology, 65: 499 (1980)] or, more expediently, by means of a commercial sequencing kit.

With the p51 gene of the present invention, for example by utilizing a partial or full-length nucleotide sequence of this gene, the expression or non-expression of the p51 gene of the present invention in a human or other individual body or various tissues thereof can be specifically detected.

This detection can be made in the routine manner. For example, determination at the cellular level by RNA amplification by RT-PCR [reverse transcribed-polymerase chain reaction; E. S. Kawasaki, et al., Amplification of RNA In PCR Protocol, A Guide to methods and applications, Academic Press, Inc., San Diego, 21-27 (1991)], Northern blotting analysis [Molecular Cloning, Cold Spring Harbor Lab. (1989)], in situ RT-PCR [Nucl. Acids Res., 21, 3159-3166 (1993)] or in situ hybridization, the NASBA method [nucleic acid sequence-based amplification, Nature, 350, 91-92 (1991)] and other techniques can be mentioned. The preferred is the RT-PCR-SSCP method.

The primers for use in the PCR procedure are not particularly restricted inasmuch as the p51 gene (inclusive of a partial DNA) of the present invention can be specifically amplified, and can be judiciously established on the basis of the sequence information on the p51 gene of the invention. Usually, for example, primers each having a partial sequence of the p51 gene of the invention and a length ranging from about 10 to 35 nucleotides, preferably 15~30 nucleotides, can be employed.

Thus, the gene of the present invention includes DNA fragments which can be used as specific primers and/or specific probes for detection of the human p51 gene of the invention.

Such a DNA fragment can be defined as the DNA characterized by its capability to hybridize with a DNA having said nucleotide sequence (145-1488) under stringent conditions. The stringent conditions mentioned above may be the conventional conditions used for primers and probes and, for that matter, not particularly restricted but the above-mentioned conditions, namely 0.1% SDS-containing 0.2×SSC at 50° C. or 0.1% SDS-containing 1×SSC at 60° C., can for example be mentioned.

With the human p51 gene of the present invention, the protein comprising the corresponding gene product (p51 protein) can be produced easily, on a large scale, and with good reproducibility by utilizing the conventional genetic engineering technology.

(2) The p51 Protein

The present invention, therefore, provides the p51 protein encoded by the above-described gene of the invention.

As specific examples of the protein of the present invention, there can be mentioned the p51A protein having the amino acid sequence shown under SEQ ID NO:1 and the protein designated as the p51B protein which has the amino acid sequence shown in SEQ ID NO:4. It should, however, be understood that the protein of the present invention is not limited to said p51A protein and p51B protein but includes their homologs. The homolog in this context includes the protein having an amino acid sequence derived from each of said amino acid sequences by deletion, substitution or addition of one~a few or a plurality of amino acids and having said p51 activity. More particularly, the gene products of said p51 gene homologs (p51-related genes including splicing variants and alleles) can be mentioned.

The protein of the present invention can be prepared by the conventional recombinant DNA technology [e.g. Science, 224, 1431 (1984); Biochem. Biophys. Res. Comm., 130, 692 (1985); Proc. Natl. Acad. Sci., USA., 80, 5990 (1983), etc.] based on the human p51 gene sequence information provided by the present invention.

(3) The polypeptide containing one or more functional domains of the p51 protein The present invention is further directed to a polypeptide containing a partial region of said p51 protein. The polypeptide preferably has the amino acid sequence corresponding to any of said various functional regions of the p51 protein and, specifically, there can be mentioned a polypeptide having an amino acid sequence corresponding to at least one domain selected from the group consisting of the transcriptional activation domain, DNA binding domain and oligomerization domain of the p51 protein. As mentioned above, the locations of the transcriptional activation domain, DNA binding domain and oligomerization domain of the p51 protein can be identified by the amino acid numbers 1~59, the amino acid numbers 142~321 and the amino acid numbers 359~397, respectively, of the amino acid sequence of the p51A protein which is shown under SEQ ID NO:1. Therefore, the polypeptide of the present invention includes the following.

(i) A polypeptide having the amino acid sequence corresponding to the amino acid numbers 1~59 of SEQ ID NO:1 (hereinafter referred to briefly as amino acid sequence 1 (1-59)) and its equivalent. The equivalent mentioned just above includes any polypeptide having an amino acid sequence derived from said amino acid sequence 1 (1-59) by deletion, substitution or addition of one or a plurality of amino acids and having a transcriptional activation function. The extent of modification or mutation of the amino acid sequence is not particularly restricted inasmuch as the modified polypeptide retains said transcriptional activation function. Preferably, however, the homogeneity of the sequence so modified to the amino acid sequence 1 (1-59) is not less than about 35%, particularly not less than 45%.

(ii) A polypeptide having an amino acid sequence identified by the amino acid numbers 142~321 of SEQ ID NO:1 (hereinafter referred to briefly as amino acid sequence 1 (142-321)) and its equivalent.

The equivalent mentioned above includes any polypeptide having an amino acid sequence derived from the amino acid sequence 1 (142-321) by deletion, substitution or addition of one or a plurality of amino acids and having said DNA binding function. The extent of modification or mutation of the amino acid sequence is not particularly restricted inasmuch as the sequence as modified retains DNA binding activity but the sequence preferably has a homology of not less than about 88%, more preferably not less than 90% with respect to the amino acid sequence 1 (142-321). (iii) A polypeptide having an amino acid sequence identified by the amino acid numbers 353~397 of SEQ ID NO:1 (hereinafter referred to briefly as amino acid sequence 1 (353-397) and its equivalent. This equivalent includes a polypeptide having an amino acid sequence derived from said amino acid sequence 1 (353-397) by deletion, substitution or addition of one or a plurality of amino acids and having an oligomerization function, for example the oligomerization domain in a broad sense (i.e. the amino acid numbers 353~641 of SEQ ID NO:4) of the p51 protein. The extent of modification or mutation of the amino acid sequence is not particularly restricted inasmuch as the sequence so modified retains the oligomerization function but preferably retains a homology of not less than about 70%, more preferably not less than 80%, with respect to the amino acid sequence 1 (353-397). The polypeptide of the present invention may be a polypeptide which contains any of said amino acid sequence 1 (1-59) or an equivalent thereof, said amino acid sequence 1 (142-321) or an equivalent thereof, and said amino acid sequence 1 (353-397) or an equivalent thereof in one region or a polypeptide which contains two or more of said amino acid sequences in an optional combination either as a continuous region or a discontinuous region.

The present invention further includes genes (DNA) having oligonucleotide sequences coding for such polypeptides. More particularly, the nucleotide sequence coding for said amino acid sequence 1 (1~59) is the nucleotide sequence corresponding to the nucleotide numbers 145~321 of SEQ ID NO:2; the nucleotide sequence coding for said amino acid sequence 1 (142-321) is the nucleotide sequence corresponding to the nucleotide numbers 568~1107 of SEQ ID NO:2; and the nucleotide sequence coding for said amino acid sequence 1 (353-397) is the nucleotide sequence corresponding to the nucleotide numbers 1201~1335 of SEQ ID NO:2 (4) Method of producing the p51 protein and the materials for use in its production The present invention further provides a method of producing said p51 protein and the materials to be used for its production, for example, a vector harboring said gene and host cells transformed with said vector. More particularly, the production of said protein is carried out in accordance with the procedure which comprises constructing a recombinant vector (expression vector) in which the gene coding for the desired protein may be expressed, transforming host cells with the resulting construct, culturing the transformant thus obtained, and harvesting the desired protein from the culture obtained.

As said host cells, whichever of eucaryotic cells and procaryotic cells can be employed. The eucaryotic host cells include cells of vertebrae and yeasts, among others. Among the former cells, the monkey cell line COS [Cell, 23: 175 (1981)], Chinese hamster ovarian cells and the dihydrofolate reductase-defective line thereof [Proc. Natl. Acad. Sci., USA., 77: 4216 (1980)] can be mentioned as examples. As to the latter cells, cells of yeasts belonging to the genus *Saccharomyces* can be mentioned as examples but these are not exclusive choices.

As the procaryotic host, various procaryotes which are commonly employed, such as *Escherichia coli* and *Bacillus subtilis*, can be liberally employed. The preferred host cells are those derived from *Escherichia coli*, particularly cells of *E. coli* K12.

The expression vector is not particularly restricted inasmuch as it harbors the gene of the present invention and permits expression of said gene but is generally selected with reference to the kinds of host cells.

When cells of a vertebrate are used as host cells, generally an expression vector having a promoter region upstream of the gene of the invention, RNA splicing site, polyadenylation site and transcription termination sequence can be used and, where necessary, it may further include a replication origin. As an example of such expression vector, pSV2dhfr [Mol. Cell. Biol., 1, 854 (1981)] having the early promoter of SV40 can be mentioned.

When cells of eucaryotic microorganisms such as yeasts are used as hot cells, the expression vector which can be used includes pAM82 [Proc. Natl. Acad. Sci., USA., 80, 1 (1983)] which has the promoter of the acid phosphatase gene, and the vector for use in the present invention can be prepared by inserting the gene of the invention upstream of this promoter. Preferably, a fusion vector obtainable by hybridization with a procaryotic gene can be used and, as specific examples of such vector, pGEX-2TK and pGEX-4T-2 each having a GST domain with a molecular weight of 26000 (derived from *S. japonicum*) can be mentioned.

When procaryotic cells are used as host cells, the expression vector may for example be a vector equipped with a promoter region and SD (Shine-Dalgarno) sequence upstream of the gene so that the gene may be expressed therein and further an initiation codon (e.g. ATG) necessary for the initiation of protein synthesis. Particularly when cells of *Escherichia coli* (e.g. *Escherichia coli* K12) are used as host cells, generally pBR322 as such or modified is often used as the vector. However, these are not exclusive choices but other known bacterial strains and known vectors can also be employed. As the promoter, tryptophan (trp) promoter, lpp promoter, lac promoter, PL/PR promoter, etc. can be employed.

The method of introducing said expression vector into the host cell (transformation method) is not particularly restricted, either, but various standardized methods can be utilized.

Culture of the resultant transformant can also be performed in the routine manner. By such culture, the object protein encoded by the gene of the invention is expressed, produced, and accumulated in the transformant cell or secreted extracellularly or on the cell membrane.

The medium for said culture can be judiciously selected from among the conventional culture media according to the type of host cells adopted, and culture can also be carried out under conditions suited for growth of the host cells.

The recombinant protein thus produced can be optionally isolated and purified by various isolation procedures utilizing its physical, chemical or other properties [Seikagaku (Biochemical) Data Book II, pp. 1175-1259, 1st Ed., 1st Impression, Jun. 23, 1980, Tokyo Kagaku Dojin; Biochemistry, 25(25): 8274 (1986); Eur. J. Biochem., 163: 313 (1987); etc.].

The procedures mentioned above specifically include the standard reconstitution treatment, treatment with a protein precipitating agent (salting out), centrifugation, osmotic shock method, sonic disruption, ultrafiltration, various kinds of chromatography, e.g. molecular sieves chromatography (gel filtration), adsorption chromatography, ion exchange chromatography, affinity chromatography, high performance liquid chromatography (HPLC), etc., dialysis, and their combinations. The particularly preferred procedure is affinity chromatography using a column conjugated with a specific antibody against the protein of the invention.

In the designing of the object gene coding for the protein of the invention, the nucleotide sequence of the human p51A gene as identified by the nucleotide sequence (145-1488) in SEQ ID NO:2 or the nucleotide sequence of the human p51B gene as identified by the nucleotide sequence (145-2067) in SEQ ID NO:5 can be utilized with advantage. If desired, this gene may be used with the codons designating respective amino acid residues judiciously changed.

Furthermore, the partial modification of the amino acid sequence encoded by the human p51A gene or human p51B gene by the substitution, deletion or addition of some of the amino acid residues or a given partial sequence can be achieved by the various techniques mentioned hereinbefore, for example by site-specific mutagenesis.

The protein of the present invention can be synthesized by the standard technology for chemical synthesis in accordance with the amino acid sequence shown under SEQ ID NO:1 or the amino acid sequence shown under SEQ ID NO:4. This technology includes the liquid-phase and solid-phase methods for peptide synthesis.

More particularly, the synthetic technology includes the so-called stepwise elongation method in which one amino acid after another is sequentially coupled together in accordance with the amino acid sequence information and the fragment condensation method in which fragments each consisting of several amino acids are synthesized in advance and then coupled together. The polypeptide of the present invention can be synthesized by whichever of the above alternative methods.

The condensation method for use in the above peptide synthesis may also be the conventional one, which includes but is not limited to the azide method, mixed acid anhydride method, DCC method, activated ester method, redox method, DPPA (diphenylphosphoryl azide) method, DCC+additive (1-hydroxybenzotriazole, N-hydroxysuccinamide, N-hydroxy-5-norbornene-2,3-dicarboximide or the like) method, and Woodward's method.

The solvent for use in these methods can also be judiciously selected from among the common solvents which are well known to those skilled in the art of peptide condensation. As examples, N,N-dimethylformamide (DMF), dimethyl sulfoxide (DMSO), hexaphosphoramide, dioxane, tetrahydrofuran (THF), ethyl acetate, etc. and mixed solvents thereof.

The carboxyl groups of amino acids or peptides which are not to be involved in the reaction for said peptide synthesis can be protected generally by esterification, for example in the form of a lower alkyl ester, e.g. methyl ester, ethyl ester, tert-butyl ester or the like, or an aralkyl ester, e.g. benzyl ester, p-methoxybenzyl ester, p-nitrobenzyl ester or the like.

The amino acid having a functional group in its side chain, for example the hydroxyl group of the tyrosine residue, may be protected with an acetyl, benzyl, benzyloxycarbonyl, tert-butyl or other group, although this protection is not indispensable. Furthermore, the guanidino group of an arginine residue, for instance, can be protected with a suitable protective group such as nitro, tosyl, p-methoxy-benzenesulfonyl, methylene-2-sulfonyl, benzyloxycarbonyl, isobornyloxycarbonyl, adamantyloxycarbonyl or the like.

The deprotection reactions of such protected amino acids, peptides and end product protein of the present invention for removal of the protective groups can also be carried out by the conventional method, for example the catalytic reduction method or the method using liquid ammonia/sodium, hydrogen fluoride, hydrogen bromide, hydrogen chloride, trifluoroacetic acid, acetic acid, formic acid, methanesulfonic acid or the like.

The protein thus produced can be purified by the procedure which is conventionally utilized in the field of peptide chemistry, such as said various methods, such as ion exchange chromatography, partition chromatography, gel permeation chromatography, countercurrent distribution, etc.

The protein of the present invention can be used with advantage as an immunogen in the preparation of a specific antibody to the p51 protein, and by using such an immunogen, the desired antiserum (polyclonal antibody) and monoclonal antibody can be acquired.

The antibody production technology as such is well understood by those skilled in the art and, in the practice of the present invention, too, the conventional methods can be utilized [e.g. Zoku Seikagaku Jikken Koza (Supplemental Biochemical Experimental Series), Methods for Immunobiochemical Research, ed. by Japanese Biochemical Society (1986)]. The antibody thus obtained can be used with advantage, for example in the purification of the p51 protein and the immunological assay or characterization of the protein.

Furthermore, the protein of the present invention finds application in the pharmaceutical field, in the manufacture of pharmaceutical products containing it as an active component.

(5) Pharmaceutical Compositions Containing the p51 Protein

The present invention, therefore, is further directed to said pharmaceutical products containing the protein of the invention.

The protein mentioned above includes its pharmaceutically acceptable salt. Such salt includes nontoxic alkali metal, alkaline earth metal and ammonium salts, such as sodium, potassium, lithium, calcium, magnesium, barium and ammonium salts. Furthermore, said salt includes nontoxic acid addition salts obtainable by reacting the peptide of the invention with a suitable organic or inorganic acid. The representative nontoxic acid addition salts are the hydrochloride, hydrobromide, sulfate, bisulfate, acetate, oxalate, valerate, oleate, laurate, borate, benzoate, lactate, phosphate, p-toluenesulfonate (tosylate), citrate, maleate, fumarate, succinate, tartrate, sulfonate, glycolate, ascorbate, benzenesulfonate and naphthalate, among others.

The present invention further comprises a pharmaceutical composition or dosage form which contains a pharmacologically effective amount of the protein of the invention as an active ingredient together with a suitable nontoxic pharmaceutical carrier or diluent.

The pharmaceutical carrier which can be utilized in said pharmaceutical composition (or dosage form) includes the diluents and excipients which are commonly used according to the mode of use of the pharmaceutical preparation, such as filler, volume builder, binder, humectant, disintegrator, surfactant, lubricant, etc., and these are selectively employed according to the unit dosage form of the pharmaceutical preparation.

The particularly preferred pharmaceutical preparation of the present invention is produced by using various formulating substances which can be incorporated in the conventional protein preparation, such as the stabilizer, bactericide, buffer, isotonizing agent, chelating agent, pH control agent, surfactant, etc., in suitable proportions.

The stabilizer mentioned above includes but is not limited to human serum albumin, ordinary L-amino acids, saccharides and cellulose derivatives and these can be used independently or in combination with a surfactant or the like. Particularly in the combination use, the stability of the active ingredient can be further improved in certain cases.

The L-amino acids mentioned above are not particularly restricted but may be glycine, cysteine, glutamic acid and so on.

The saccharides mentioned above include monosaccharides such as glucose, mannose, galactose, fructose, etc., sugar alcohols such as mannitol, inositol, xylytol, etc., disaccharides such as sucrose, maltose, lactose, etc., polysaccharides such as dextran, hydroxypropylstarch, chondroitin sulfate, hyaluronic acid, etc., and their derivatives.

The surfactant is not particularly restricted, either. Thus, ionic surfactants and nonionic surfactants, such as surfactants in the polyoxyethylene glycol sorbitan alkyl ester, polyoxyethylene alkyl ether, sorbitan monoacyl ester and fatty acid glyceride series can be mentioned.

The cellulose derivatives are not particularly restricted, either, but methylcellulose, ethylcellulose, hydroxyethylcellulose, hydroxypropylcellulose, hydroxypropylmethylcellulose, carboxymethylcellulose sodium, etc. can be mentioned.

The suitable level of addition of the saccharide per 1 µg of the active ingredient is not less than about 0.0001 mg, preferably about 0.01~10 mg. The level of addition of the surfactant per 1 µg of the active ingredient may suitably be not less than about 0.00001 mg, preferably about 0.0001~0.01 mg. The level of addition of human serum albumin per 1 µg of the active ingredient may suitably be not less than about 0.0001 mg, preferably somewhere within the range of about 0.001~0.1 mg. The level of addition of said amino acid per µg of the active ingredient is suitably about 0.001~10 mg. The level of addition of the cellulose derivative per µg of active ingredient is suitably not less than about 0.00001 mg, preferably about 0.001~0.1 mg.

The amount of the active ingredient in the pharmaceutical dosage form can be liberally selected from a broad range but can be judiciously selected from the range of generally about 0.00001~70 weight %, preferably about 0.0001~5 weight %.

The pharmaceutical dosage form of the present invention may be supplemented with various additives, such as a buffer, an isotonizing agent, a chelating agent, etc. The buffer mentioned above includes boric acid, phosphoric acid, acetic acid, citric acid, ε-aminocaproic acid, glutamic acid, etc. and/or the corresponding salts (alkali metal or alkaline earth metal salts, e.g. sodium salt, potassium salt, calcium salt, magnesium salt, etc.). The isotonizing agent includes but is not limited to sodium chloride, potassium chloride, sugars and glycerin. The chelating agent includes sodium edetate and citric acid, among others.

The pharmaceutical composition of the present invention can be used not only as it is in the form of a solution but also provided in the form of a lyophilized product which can be preserved and extemporaneously reconstituted with water or a buffer solution inclusive of physiological saline to a suitable concentration.

The unit dosage form for the pharmaceutical composition of the present invention can be selected from various alternatives according to the therapeutic purpose, and includes solid dosage forms, such as tablets, pills, powders, fine powders, granules, capsules, etc. and liquid dosage forms, such as solutions, suspensions, emulsions, syrups and elixirs. These dosage forms can be further classified as the oral, parenteral, transnasal, vaginal, rectal (suppository) and sublingual dosage forms, ointments and other products, and each product can be manufactured in accordance with the established formulation and molding/processing procedure.

Taking the manufacture of tablets as an example, the pharmaceutical carrier which can be used includes various excipients such as lactose, sucrose, sodium chloride, glucose, urea, starch, calcium carbonate, kaolin, crystalline cellulose, silicic acid, potassium phosphate, etc.; binders such as water, ethanol, propanol, simple syrup, glucose solution, starch solution, gelatin solution, carboxymethylcellulose, hydroxypropylcellulose, methylcellulose, polyvinylpyrrolidone, etc. disintegrators such as carboxymethylcellulose sodium, carboxymethylcellulose calcium, low-substitution-degree hydroxypropylcellulose, dry starch, sodium alginate, agar powder, laminaran powder, sodium hydrogencarbonate, calcium carbonate, etc.; surfactants such as polyoxyethylene sorbitan fatty acid esters, sodium lauryl sulfate, stearyl monoglyceride, etc.; disintegration inhibitors such as sucrose, stearin, cacao butter, hydrogenated oil, etc.; absorption promoters such as quaternary ammonium bases, sodium lauryl sulfate, etc.; humectants such as glycerin, starch, etc.; adsorbents such as starch, lactose, kaolin, bentonite, colloidal silica, etc.; and lubricants such as purified talc, stearate salts, boric acid powder, polyethylene glycol and so on.

Furthermore, tablets may optionally be coated with a usual coating material to provide sugar-coated tablets, gelatin-coated tablets, enteric-coated tablets, film-coated tablets, etc. or even processed into multilayer tablets such as double-layer tablets.

Pills can be manufactured by using various pharmaceutical carriers inclusive of excipients such as glucose, lactose, starch, cacao butter, hydrogenated vegetable oil, kaolin, talc, etc.; binders such as gum Arabic, tragacanth powder, gelatin, ethanol, etc.; and disintegrators such as laminaran, agar and so on.

Capsules can be prepared by blending the active ingredient of the present invention with said various pharmaceutical carriers and filling capsule shells, such as hard gelatin capsule shells or soft capsule shells, with the resulting composition.

Liquid dosage forms for oral administration include pharmaceutically acceptable solutions, emulsions, syrups, elixirs, etc. as prepared by using the conventional inert diluent, such as water, and may further contain auxiliary agents such as wetting agents, emulsifiers and suspending agents. These dosage forms can be manufactured by the conventional procedure.

Liquid dosage forms for parenteral or nonoral administration, such as sterile aqueous or nonaqueous solutions, emulsions and suspensions, can be manufactured using a diluent such as water, ethyl alcohol, propylene glycol, polyethylene glycol, ethoxylated isostearyl alcohol, polyoxylated isostearyl alcohol, polyoxyethylene sorbitan fatty acid ester, a vegetable oil, e.g. olive oil, and may be formulated with an injectable organic ester, such as ethyl oleate. Furthermore, such preparations may be supplemented with the conventional solubilizer, buffer, wetting agent, emulsifier, suspending agent, preservative, dispersant and other additives.

Sterilization may be carried out by filtration through a bacterial filter, formulation of a bactericide, irradiation, heating or the like. Furthermore, said preparations can be processed into sterile solid dosage forms which can be extemporaneously dissolved in sterile water or a suitable sterilizable medium.

In the manufacture of rectal suppositories or a dosage form for vaginal administration, there can be employed a pharmaceutical ointment base such as polyethylene glycol, cacao butter, a higher alcohol, a higher alcohol ester, gelatin, semi-synthetic glyceride or the like.

In the manufacture of ointments inclusive of pastes, creams and gels, there can be employed such diluents as white petrolatum, paraffin, glycerin, cellulose derivatives, propylene glycol, polyethylene glycol, silicone oil, bentonite and vegetable oils such as olive oil.

Compositions for transnasal or sublingual administration can be prepared with the well-known standard excipient in the conventional manner.

Where necessary, coloring agents, preservatives, flavoring agents, corrigents, sweeteners, and other medicinal substances can be incorporated in the pharmaceutical products of the present invention.

The method of administering said pharmaceutical product is not particularly restricted but should be judiciously selected according to the dosage form, patient factors such as age and sex, severity of illness and other factors. For example, said tablets, pills, solutions, suspensions, emulsions, granules and capsules are administered orally. The parenteral product is used alone or mixed with a conventional infusion, such as a glucose or amino acid infusion, and administered intravenously or, where necessary, administered alone intramuscularly, intradermally, subcutaneously or intraperitoneally. The suppositories are administered rectally; the vaginal preparation is administered into the vagina. The transnasal preparation is administered into the nostrils; sublingual tablets are administered buccally; and ointments are topically administered transdermally.

The amount of the protein of the invention in the pharmaceutical product and the dosage thereof are not particularly restricted but can be judiciously selected from a broad range according to the expected therapeutic effect, administration method, treatment course or duration, patient factors such as age and sex, and other factors. Generally, the dosage is usually about 0.01 μg~10 mg/kg body weight/day, preferably about 0.1 μg~1 mg/kg b.d./day, and this amount can be administered once or in a few divided doses daily.

(6) Gene Therapy

The present invention further provides a method of gene therapy utilizing the human p51 gene of the invention. This therapeutic method may be regarded as a method for imparting the wild type p51 gene functions to the cells harboring a mutant p51 gene. By imparting the normal functions inherently possessed by the wild type p51 gene or gene product to cells, neoplastic growth of the recipient/target cells can be inhibited. The wild type p51 gene mentioned above can be transferred into the objective cells by means of a vector or plasmid capable of maintaining the gene extrachromosomally. In this case, the particular gene is expressed from outside of the chromosome.

In introducing the wild type p51 gene into cells harboring such a mutant p51 gene to have a normal p51 protein expressed in the recipient cells, the p51 gene need not have a full-length sequence but may be said modified gene insofar as the latter has substantially homologous desired functions with respect to the unmodified gene. As an alternative, a gene having a partial sequence retaining certain such functions can be employed. As an example of the gene mentioned just above, there can be mentioned a gene coding for a portion of p51 protein which is necessary for nontumorous growth of cells (cell growth inhibition).

The wild type p51 gene or a fragment thereof is preferably introduced into mutant cells in such as manner that a recombination will take place with the endogenous mutant p51 gene. For such a recombination, occurrence of a double recombination correcting for the p51 gene mutation is said to be required.

The vectors which can be used in the transfer of the object gene for both such recombination and extrachromosomal maintenance of the gene are already known in the art and any of the known vectors can be used in the practice of the present invention. For example, a virus vector or plasmid vector which harbors a copy of p51 gene linked to an expression control element and is capable of insuring expression of the gene product within the target cells can be mentioned. As such a vector, the expression vectors mentioned above can be generally used but preferably vectors constructed using such source vectors as the vectors disclosed in U.S. Pat. No. 5,252,479 and PCT WO 93/07282 (pWP-7A, pwP-19, pWU-1, pWP-8A, pWP-21 and/or pRSVL, among others) or pRC/CMV (Invitrogen). The more preferred are the various virus vectors described hereinafter.

As the promoter for the vector to be used in gene therapy, the promoters intrinsic to the target affected tissues in various diseases can be utilized with advantage.

Specific examples may be cited below. For the liver, for instance, albumin, α-fetoprotein, α1-antitrypsin, transferrin, transthyretin, etc. can be mentioned by way of example. For the colon, carboxyl anhydrase I, carcinoembrogen antigen, etc. can be mentioned. For the uterus and placenta, estrogen, aromatase cytochrome P450, cholesterol side-chain cleaving P450, 17α-hydroxylase P450, etc. can be mentioned.

For the prostate, prostatic antigen, gp91-fox gene, prostate-specific kallikrein, etc. can be mentioned. For the mamma, erb-B2, erb-B3, β-casein, β-lactoglobin, whey protein, etc. can be mentioned. For the lung, the activator protein C uroglobulin, among others, can be mentioned. For the skin, K-14-keratin, human keratin 1 or 6, leucrin, etc. can be mentioned.

For the brain, neuroglia fiber acid protein, mature astrocyte-specific protein, myelin, tyrosine hydroxylase pancreatic villin, glucagon, Langerhans islet amyloid polypeptide, etc. can be mentioned. For the thyroid, thyroglobin, calcitonin, etc. can be mentioned. For the bone, α1 collagen, osteocalcin, bone sialoglycoprotein, etc. can be mentioned. For the kidney, renin, liver/bone/kidney alkaline phosphatase, erythropoietin, etc. can be mentioned. For the pancrease, amylase, PAP1, etc. can be mentioned.

The gene (the whole or a fragment) to be used for the construction of a gene transfer vector can be easily produced and acquired by the standard genetic engineering technology based on the nucleotide sequence information about the p51 gene of the invention as mentioned hereinbefore.

The introduction of such a gene transfer vector into cells can be carried out by various alternative techniques known to those skilled in the art, such as electroporation, calcium phosphate coprecipitation, viral transduction and so on. The cells transformed with the wild type p51 gene can be used as they are in the isolated form as the agent for tumor suppression or inhibition of cancer metastasis or as a model system for therapeutics research.

In gene therapy, said gene transfer vector can be introduced into the tumor cells of a patient by topical administration to the tumor site or by systemic administration to the patient by injection. By systemic administration, the gene can be caused to arrive at any tumor cells metastable to other sites. If the transformed cells cannot be permanently taken up in the chromosomes of the target tumor cells, the above administration may be repeated periodically.

The method of gene therapy according to the present invention includes both the in vivo method which comprises administering a material for said gene transfer (gene transfer vector) directly into the body and the ex vivo method which comprises withdrawing the target cells from the patient's body, introducing the gene extracorporeally, and returning the cells into the body.

A further possible alternative is a gene therapy using a ribozyme which comprises introducing the human p51 gene directly into cells and cleaving the RNA chain with the ribozyme which is an active molecule.

The gene transfer vector harboring the human p51 gene of the invention or a fragment thereof and a gene-therapeutic agent comprising cells transformed with the human p51 gene by means of said vector as an active ingredient are directed especially to the therapy of cancers but the gene therapy (treatment) mentioned above can be applied also to the therapy of hereditary diseases and viral diseases such as AIDS, as well as for the purpose of gene labeling.

The target cells to which the gene is transferred can be judiciously selected according to the object of gene therapy (treatment). For example, as the target cells, not only cancer cells and tumor tissues but also lymphocytes, fibroblasts, hepatocytes, hematopoietic stem cells and other cells can be mentioned.

The method of introducing the gene into cells in the gene therapy includes a viral transfer method and a non-viral transfer method.

As the viral transfer method, the method using a retrovirus vector, for instance, can be used in view of the fact that the human p51 gene is a foreign gene which is expressed in normal cells. As other virus vectors, adenovirus vector, HIV (human immunodeficiency virus) vector, adeno-associated virus (AAV) vector, herpes virus vector, herpes simplex virus (HSV) vector and Epstein-Barr virus (EBV) vector, etc. can be mentioned.

The non-viral gene transfer method includes the calcium phosphate coprecipitation method; the membrane-fusion liposome method which comprises fusing DNA-containing liposomes with an inactivated Sendai virus as exposed to UV radiation for gene destruction to construct membrane-fusion liposomes and introducing the DNA into cells by direct fusion with the cell membrane [Kato, K., et al., J. Biol. Chem., 266, 22071-22074 (1991)]; the method which comprises coating the plasmid DNA with gold and introducing the DNA physically into cells by high-voltage discharge [Yang, N. S. et al., Proc. Natl. Acad. Sci., 87, 9568-9572 (1990)]; the naked DNA method in which the plasmid DNA is directly injected into an organ or tumor in vivo [Wolff, J. A., et al., Science, 247, 1465-1467 (1990)]; the cationic liposome method in which the gene entrapped in multilamellar positively-charged liposomes are introduced into cells [Yagi, K., Advance in Medicine, vol. 175, No. 9, 635-637 (1995)]; and the ligand-DNA complex method in which a ligand which binds a receptor expressed on the target cells is coupled to the DNA so that the gene may be introduced exclusively into the selected cells and not into other cells and the resulting complex is administered [Frindeis, et al., Trends Biotechnol., 11, 202 (1993); Miller, et al., FASEB J., 9, 190 (1995)] among others.

The ligand-DNA complex method mentioned above includes the method which comprises using the asialoglycoprotein receptor expressed in liver cells as the target and an asialoglycoprotein as the ligand [Wu, et al., J. Biol. Chem., 266, 14338 (1991); Ferkol, et al., FASEB J., 7, 1081-1091 (1993)] and the method which comprises using the transferrin receptor expressed at a high level in tumor cells as the target and transferrin as the ligand [Wagner et al., Proc. Natl. Acad. Sci., USA., 87, 3410 (1990)], among others.

Furthermore, the gene transfer method which can be used may be a suitable combination of said biological and physical gene transfer methods. As such a combination method, there can be mentioned the method in which a plasmid DNA having a given size is used in combination with a polylysine-conjugated antibody specific to adenovirus hexon protein. According to this method, the complex formed is bound to the adenovirus vector and the resulting trimolecular complex can be used to infect cells and thereby transfer the gene of the present invention. In accordance with this method, effective binding, endogenization and endosome degradation can take place before the DNA coupled to the adenovirus vector is damaged. Moreover, said liposome/DNA complex may mediate the gene transfer in vivo.

The method of constructing a virus vector for transfer of the gene of the invention and the method of introducing the gene into the target cells or target tissue are now described.

The retrovirus vector system comprises the virus vector and helper cells (packaging cells). The helper cells mentioned above are cells in which genes such as retrovirus structural protein gag (the structural protein in the virus particle), pol (reverse transcriptase) and env (shell protein) have been expressed but have not formed virus particles. On the other hand, the virus vector has a packaging signal and LTR (long terminal repeats) but are devoid of structural genes necessary for virus replication, such as gag, pol and env. The packaging signal is a sequence serving as the tag in the assembling of a virus particle and the selective genes (neo, hyg) and the desired gene (p51 gene or a fragment thereof) incorporated in the cloning site are inserted in place of the virus gene. Here, in order to acquire a high titer of virus particles, it is important to make the insert as short as possible, broaden the packaging signal by including a part of the gag gene and use care not to leave the ATG of the gag gene.

By introducing the vector DNA harboring the object p51 gene into the helper cells, the vector genome RNA is packaged with the virus structural protein of the helper cells to form and secrete virus particles. After the virus particle as the recombinant virus has infected the target cell, the DNA reverse-transcribed from the virus genome RNA is integrated into the cell nucleus and the gene inserted into the vector is expressed.

As the method of improving the efficiency of transfer of the object gene, the method using a fragment containing the cell adhesion domain of fibronectin, the heparin-binding site and conjugation segment can be employed [Hanenberg, H., et al., Exp. hemat., 23, 747 (1995)].

As an example of the vector for use in the above retrovirus vector system, the retrovirus derived from mouse leukemia virus [McLachlin, J. R., et al., Proc. Natl. Acad. Res. Molec. Biol., 38, 91-135 (1990)] can be mentioned.

The method comprising using the adenovirus vector is now described in detail.

Construction of said adenovirus vector can be carried out in accordance with the methods of Berkner [Berkner, K. L., Curr. Topics Microbiol. Immunol., 158, 39-66 (1992)], Setoguchi, Y. et al. [Setoguchi, Y., et al., Blood, 84, 2946-2953 (1994)], Kanegae, H. et al. [Experimental Medicine(?), 12, 28-34 (1994)], and Ketner et al. [Ketner, G., et al., Proc. Natl. Acad. Sci., USA., 91, 6186-6190 (1994)].

For example, for the construction of a nonproliferative adenovirus vector, the early gene E1 and/or E3 gene regions of adenovirus are first removed. Then, a plasmid vector harboring the object foreign gene expression unit (consisting of the gene to be transferred, which is the p51 gene in the present invention, a promoter for transcription of the gene, and poly-A which imparts stability to the transcript) and a portion of the adenovirus genome DNA and a plasmid harboring the adenovirus genome are used to concurrently transfect cells, e.g. 293-cells. By causing a homologous recombination to take place between the two and thereby substitute the gene expression unit for E1, the nonproliferative adenovirus vector harboring the p51 gene according to the present invention can be constructed. It is also possible to integrate the adenovirus genome DNA into the cosmid vector to construct a 3'-end adenovirus vector with the terminal protein added. Furthermore, the YAC vector can also be utilized in the construction of a recombinant adenovirus vector.

The production of an adeno-associated virus (AAV) vector is now briefly described. AAV was discovered as a small-sized virus contaminating a culture system of adenovirus. Of this virus, the parvovirus genus which does not require a helper virus for replication but proliferates autonomously in the host cell and the dependvirus which requires a helper virus have been confirmed. This AAV is one of the common viruses which has a broad host range and infects a variety of cells. Its genome is a linear single-stranded DNA consisting of 4680 nucleotides and the 145 nucleotides at either terminus has a characteristic sequence called ITR (inverted terminal repeat). This ITR region is a replication initiation point and plays the role of a primer. Furthermore, this ITR is indispensable to the packaging to the virus particle and the integration into the chromosomal DNA of the host cell. In addition, with regard to the virus protein, the left-half of the genome codes for a nonstructural protein, that is the regulatory protein Rep which controls replication and transcription.

Construction of a recombinant AAV can be carried out by utilizing the property of AAV to be integrated with chromosomal DNA, whereby a vector for transfer of the desired gene can be constructed. More particularly, in accordance with this method, a plasmid (AAV vector plasmid) harboring the object gene to be transferred (human p51 gene) inserted between the remnant ITRs at both the 5'- and 3'-ends of the wild type AAV is first constructed. On the other hand, the virus protein necessary for virus replication and construction of the virus particle is supplied from an independent helper plasmid. It is insured that there will be no nucleotide sequence common to both plasmids so that a recombinant wild-type virus will not emerge. Then, both plasmids are introduced by transfection into, for example, 293-cells, which are further infected with adenovirus (which may be nonproliferative type when 293- cells are used) as the helper virus, whereby the objective recombinant AAV of the nonproliferative type is produced. Since this recombinant AAV exists in the nucleus, it is recovered by freeze-thaw and the contaminant adenovirus is inactivated by heating at 56° C. Where necessary, the recombinant AAV is isolated and concentrated by ultracentrifugation with cesium chloride. In this manner, the objective recombinant AAV for transfer of the object gene can be acquired.

Construction of the HIV vector can be carried out typically in accordance with the method of Shimada et al. [Shimada, T., et al., J. Clin. Invest., 88, 1043-1047 (1991)].

Since the HIV virus specifically infects helper T cells with CD4 as the receptor, a tissue-specific gene transfer HIV vector adapted for specific introduction of a gene into human CD4-positive cells can be constructed. This HIV vector is optimal for the gene therapy of AIDS.

Construction of a recombinant HIV vector can be carried out typically as follows. First, the packaging plasmid CGPE is constructed in such a manner that the structural genes gag, pol and env and the control genes (tat, rev, etc.) necessary for expression thereof may be expressed with the cytomegalovirus (CMV) promoter and the human globin gene poly A signal (poly A). Then, the vector plasmid HXN can be constructed so as to permit efficient proliferation in COS cells by inserting the bacterial neomycin-resistant gene (neoR) having a promoter for thymidine kinase (TK) as a marker gene between the two LTRs of HIV and further inserting a SV40 replication mechanism into the basal plasmid vector. As the above packaging plasmid CGPE and vector plasmid HXN are concurrently introduced by transfection into COS cells, the objective neoR gene-integrated recombinant virus is produced and released into the culture medium in a large quantity.

Production of the EBV vector can be carried out typically in accordance with the method of Shimidzu et al [Shimidzu, N., Cell Engineering(?), 14(3), 280-287 (1995)].

The production of an EBV vector for transfer of the gene of the present invention is now briefly described. EB virus (Epstein-Barr virus: EBV) is a virus belonging to the herpes family and was isolated from cultured cells derived from Burkitt lymphoma by Epstein and coworkers in 1964 [Kieff, E. and Liebowitz, D.: Virology, 2nd ed. Raven Press, New York, 1990, pp. 1889-1920]. The EBV has cell-transforming activity and, therefore, in order that it may be utilized as a gene transfer vector, the virus defective of this transforming activity must be prepared. This can be done as follows.

Thus, in the first place, an EBV genome close to the target DNA with which the desired foreign gene is to be integrated is cloned. With this clone, a foreign gene DNA fragment and a drug-resistant gene are integrated to prepare a vector for production of a recombinant virus. Then, the vector for construction of a recombinant virus is excised with suitable restriction enzymes and introduced by transfection into EBV-positive Akata cells. The recombinant virus produced by the homologous recombination can be recovered, together with the wild type Akata EBV, through virus production stimulation by anti-surface immunoglobulin treatment. This is used to infect EBV-negative Akata cells and a resistant strain is selected in the presence of the drug to obtain the desired Akata cells infected exclusively by the recombinant virus and free from the wild type EBV. Then, by inducing virus activity in the recombinant virus-infected Akata cells, the objective recombinant virus vector can be produced in a large quantity.

Production of a non-virus vector for the introduction of the desired gene into target cells without use of a recombinant virus vector can be carried out by the gene transfer technique using a membrane fusion liposome preparation. This is a technique such that by imparting fusion activity to a membrane liposome (a vesicle having a lipid bilayer structure), the contents of the liposome are directly introduced into the cell.

Introduction of the gene by means of such membrane fusion liposomes can be carried out typically in accordance with the method of Nakanishi et al. [Nakanishi, M., et al., Exp. Cell Res., 159, 399-499 (1985); Nakanishi, M., et al., Gene introduction into animal tissues. In Trends and Future Perspectives in Peptide and Protein Drug Delivery (ed. by Lee, V. H. et al.)., Harwood Academic Publishers Gmbh. Amsterdam, 1995, pp. 337-349].

This method of gene transfer by means of said membrane fusion liposomes is briefly described below. Thus, liposomes in which Sendai virus with its gene inactivated by UV irradiation, the object gene and a high molecular substance, such as protein, have been entrapped is fused at 37° C. This membrane fusion liposome has a structure called "pseudovirus" which consists of a liposome-derived inner cavity and an outer spike structure similar to that of the virus envelope. After purification by sucrose density gradient centrifugation, the membrane fusion liposomes are caused to get adsorbed on the target cultured cells or tissue cells at 4° C. Then, as the temperature is increased to 37° C., the contents of the liposomes are introduced into the cell, whereby the desired gene can be transferred to the target cells. The lipid for said liposome in this case is a synthetic phospholipid composed of 50% (by mole) each of cholesterol and lecithin and having a negative charge and is preferably formed as a unilamellar liposome with a diameter of 300 nm.

As an alternative method of introducing the gene into the target cell by means of liposomes, the gene transfer method using cationic liposomes can be mentioned. This method can be practiced in accordance with the method of Yagi et al. [Yagi, K., et al., B. B. R. C., 196, 1042-1048 (1993)]. Thus, with attention paid to the fact that plasmids and cells are both negatively charged, a positive charge is imparted to both the external and internal surfaces of the liposome membrane so that the uptake of the plasmid is increased by static electricity to enhance the interaction with the cells. The liposome used in this case is preferably a multilamellar large vesicle (MLV) having a positive charge, although it is possible to use a large unilamellar vesicle (LUV) or a small unilamellar vesicle (SUV) to construct a complex with the plasmid for introduction of the desired gene.

The method of preparing a plasmid-containing cationic MLV is briefly described below.

In the first place, a chloroform solution containing the lipid TMAG (N-($\alpha$-trimethylammonioacetyl)-didodecyl-D-glutamate chloride), DLPC (dilauroyl phosphatidylcholine) and DOPE (dioleoyl phosphatidylethanolamine) in a molar ratio of 1:2:2 is prepared (lipid concentration: 1 mM). Then, a total of 1 μmol of lipid is placed in a centrifuge tube and the chloroform is distilled off under pressure using a rotary evaporator to prepare a lipid thin film. The residual chloroform is completely removed under reduced pressure and the film is dried. Then, 0.5 ml of Mg and Ca-containing Dulbecco's phosphate-buffered saline containing 20 μg of the gene transfer plasmid is added and, after nitrogen purging, the mixture is stirred with a vortex mixer for 2 minutes to give a suspension of the gene-harboring plasmid-containing cationic MLV.

The following is an example of use of the plasmid-containing cationic MLV as a gene therapy agent. For example, the expression plasmid integrated with the cDNA of the object gene is entrapped in an amount of 0.6 μg as DNA per 30 nmole of liposome lipid in the above cationic MLV and the liposomes are suspended in 2 μl of phosphate-buffered saline.

This suspension is administered to the target cells extracted from the patient or the target patient tissue every other day.

In this connection, in the guidelines established by the Ministry of Health and Welfare of Japan, the gene therapy is defined as "to administer a gene or a gene-integrated cell into the human body for the therapy of a disease". However, the gene therapy in the context of the present invention encompasses not only the therapy falling under the above definition but also the therapy of various diseases inclusive of cancer which comprises introducing a gene characterized as a tumor suppressor gene, such as the human p51 gene, into said target cells and the practice which comprises introducing a marker gene or cells integrated with such a marker gene into the human body.

In the gene therapy according to the present invention, the method of introducing the object gene into the target cells or tissues includes the following two representative methods.

The first method comprises isolating the target cells from the patient to be treated, growing the cells extracorporeally, for example in the presence of interleukin-2 (IL-2) or the like, introducing the p51 gene ligated to the retrovirus vector into the cells, and retransplanting the resulting cells (ex vivo method). This method is suited for the therapy of ADA deficiency syndrome, hereditary diseases and cancers associated with defective genes, AIDS, and other diseases.

The second method is a direct gene transfer method which comprises injecting the object gene (human p51 gene) directly into the patient's body or target site, such as a tumor tissue (direct method).

More particularly, the above first method of gene therapy can be carried out typically as follows. Thus, the mononuclear cells isolated from the patient are separated from monocytes with a blood separator, the harvested cells are cultured in the presence of IL-2 in a suitable medium such as AIM-V medium for about 72 hours, and the vector harboring the gene to be introduced (human p51 gene) is added. For enhanced gene transfer efficiency, the system may be centrifuged at 2500 rpm in the presence of protamine at 32° C. for 1 hour and incubated under 10% carbon dioxide gas at 37° C. for 24 hours. After the above procedure is repeated a few times, the cells are further cultured in the presence of IL-2 in AIM-V or other medium for 48 hours. The cells are washed with saline, viable cells are counted, and the gene transfer efficiency is evaluated by carrying out said in situ PCR or, when the object function is enzymatic activity, assaying the activity to confirm the gene transfer effect.

In addition, a safety check comprising culture of the bacteria and fungi contaminating the cultured cells and testing for mycoplasma infection and for endotoxin is carried out to confirm safety. Then, the cultured cells integrated with a predicted effective dose of the gene (human p51 gene) are returned to the patient by intravenous drip injection. This procedure is repeated at an interval of a few weeks or a few months for gene therapy.

The dosage of the virus vector can be judiciously selected according to the kind of target cell. Usually, in terms of virus titer, a dose within the range of $1 \times 10^3$ cfu~$1 \times 10^8$ cfu is used per $1 \times 10^8$ target cells.

An alternative version of the above first method, which can be employed, comprises co-culturing virus-producing cells containing a retrovirus vector harboring the desired gene (human p51 gene) with, for example, the patient's cells to introduce the gene (human p51 gene) into the target cells.

In carrying out the second method of gene therapy (direct method), a preliminary experiment, particularly an ex vivo experiment, is preferably performed to confirm whether the object gene (human p51 gene) may be actually transferred or not by a PCR of the vector gene cDNA or an in situ PCR assay or confirm the desired effect of therapy resulting from the transfer of the object gene (human p51 gene), for example an elevation in specific activity or an enhancement or suppression of growth of target cells. Furthermore, when a virus vector is used, it is, of course, important, in conducting a gene therapy, to confirm the safety of introduction of the gene by carrying out the PCR to search for proliferative retrovirus, determining the reverse transcriptase activity, or monitoring the membrane protein (env) gene by a PCR technique.

When the method of gene therapy according to the present invention is applied to cancers or malignant tumors in particular, a typical protocol for cancer therapy may comprise isolating cancer cells from the patient, treating the cells with an enzyme or the like to establish a cultured cell line, introducing the desired gene into the target cancer cells by means of retrovirus or the like, carrying out a screening with G418 cells, determining the amount of expression of IL-12 or the like (in vivo), subjecting the cells to radiation treatment, and inoculating the cells into the patient's tumor or paratumor.

The herpes simplex virus-thymidine kinase (HSV-TK) gene reportedly causes cell death due to division aging, particularly by converting the nucleotide analog gancyclovir (GCV) to a toxic intermediate, and there is known a gene therapy using this gene in tumors [U.S. Pat. No. 5,631,236; J P Kohyo H9-504784]. This method is a method of gene therapy which utilizes the phenomenon that when cells capable of producing a retrovirus vector harboring said HSV-TK gene, known as a suicide gene, are injected and, one week later, the antiviral agent GCV is administered, the GCV in the gene-transformed cells is activated by phosphorylation to induce death of these cells and death of the surrounding non-gene-transferred cells due to cell contact through the gap junction. The gene transfer vector of the invention or cells containing this vector can be used in the above gene therapy as well.

An alternative method of gene therapy comprises preparing immunoliposomes containing the gene (human p51 gene) coupled to the antibody capable of coupling to the target cell surface to introduce the entrapped cDNA into the target cells selectively and with good efficiency. Feasible as well is a gene therapy which comprises administering said cytokine gene-harboring virus vector and said suicide gene-harboring adenovirus at one and the same time. These methods invariably fall within the expertise of those skilled in the art.

(7) Pharmaceutical Composition for Gene Therapy

The present invention further provides a pharmaceutical composition or agent (gene-therapeutic agent) comprising a pharamcologically effective amount of cells to which either the gene transfer vector or the object gene (e.g. human p51 gene or the like) of the invention has been transferred as an active ingredient together with a suitable nontoxic pharmaceutical carrier or diluent.

The pharmaceutical carrier which can be formulated in the pharmaceutical composition (preparation) of the present invention includes the conventional diluents and excipients, such as filler, volume builder, binder, humectant, disintegrator, surfactant, lubricant, etc., which are commonly employed according to the method of use of the preparation and these carriers can be selectively used with reference to the desired unit dosage form.

The unit dosage form for the pharmaceutical composition of the present invention includes the same dosage forms as those mentioned for the p51 protein and can be judiciously selected according to the therapeutic objective.

For example, a pharmaceutical preparation containing the gene transfer vector of the invention can be provided in the form of said vector entrapped in liposomes or in the form of cultured cells infected with a virus containing a retrovirus vector harboring the object gene.

These can be prepared as solutions in phosphate-buffered saline (pH 7.4), Ringer's injection or an intracellular fluid composition injection, for instance, or in such a form that it may be administered together with a substance capable of enhancing the efficiency of gene transfer, such as protamine.

The method of administering the above pharmaceutical preparation is not particularly restricted but is selected according to the dosage form, the patient's age, sex and other factors, the severity of illness, and other conditions.

The amount of the active ingredient to be incorporated in said pharmaceutical composition or preparation are not particularly restricted but can be liberally selected from a broad range according to the desired therapeutic effect, administration method, duration of treatment, the patient background inclusive of age and sex, and other conditions.

Generally speaking, the daily dose of the gene-harboring retrovirus vector as a pharmaceutical preparation per kilogram body weight may for example be about $1 \times 10^3$ pfu to $1 \times 10^{15}$ pfu in terms of retrovirus titer.

In the case of cells to which the object gene has been introduced, the dosage may be judiciously selected from the range of about $1 \times 10^4$ cells/body to about $1 \times 10^{15}$ cells/body.

The pharmaceutical product can be administered once a day or in a few divided doses a day, and may be administered intermittently, for example one to several weeks apart. Moreover, it can be advantageously administered in combination with a substance capable of enhancing the efficiency of gene transfer, such as protamine, or a pharmaceutical preparation containing said substance.

When the gene therapy of the present invention is applied to the treatment of a cancer, the various methods of gene therapy mentioned above may be used in a suitable combination (combination gene therapy) and/or in combination with the conventional cancer chemotherapy, radiation therapy, immunotherapy and/or other therapy. Furthermore, the gene therapy according to the present invention can be carried out with reference to the NIH Guidelines, inclusive of the safety aspect thereof [cf. Recombinant DNA Advisory Committee, Human Gene Therapy, 4, 365-389 (1993)].

(8) Application to Tumor Diagnosis

In accordance with the present invention, the presence of a mutant p51 gene which promotes tumorigenesis in human cells can be detected by the procedure which comprises preparing a blood, serum or other biological sample, optionally extracting the nucleic acid, and analyzing it for the presence or absence of a sensitive mutant p51 gene. Furthermore, in accordance with the present invention, the existence of a neoplastic change in cells or tissues, a marker of progression to a prodromal state of malignancy or a prognostic marker can be detected by the procedure which comprises preparing a disorder-containing biological sample and analyzing it for the presence or absence of a neoplastic mutant p51 gene. By the above procedure, the presence of a neoplasm in cells or tissues, a marker of progression to a prodromal state of malignancy or a prognostic marker can be detected, thus allowing to establish a diagnosis, for example the diagnosis of a cancer, evaluate the effect of a cancer therapy, or predict the prognosis of the cases.

According to this detection method, based on the mutant p51 gene information obtained from a tumor-bearing patient sample, for example on the information about the mutation site of the p51 gene and the mutant sequence information, the relevant mutant DNA fragment is prepared and designed so that it may be used in the screening for the mutant gene and/or the amplification thereof. More particularly, the probe for use in plaque hybridization, colony hybridization, Southern blotting, Northern blotting, etc. or the probe for PCR amplification of the mutant DNA fragment can be constructed. For such purposes, a primer having the same sequence as the mutation is first prepared and reacted, as a screening probe, with a biological sample (nucleic acid sample), whereby the presence of a gene having a mutated p51 gene sequence can be confirmed. To facilitate detection of the target sequence, said nucleic acid sample may be prepared by utilizing various techniques such as lysis, restriction enzyme digestion, electrophoresis or dot blotting.

Referring to the screening method mentioned above, the use of a PCR method is particularly preferred from the standpoint of sensitivity, and this method is not particularly restricted inasmuch as the mutant p51 fragments are used as primers. Thus, any of the hitherto-known techniques [Science, 230, 1350-1354 (1985)] and versions of PCR which have been newly developed or will be used in future [Sakaki, Y et al. (ed): Experimental Medicine(?), Supplemental Issue, 8(9) (1990), Yodo-sha; Protein, Nucleic Acid and Enzyme, Special Supplemental Issue, 35(17) (1990), Kyoritsu Shuppan] can be employed.

The DNA fragments for use as primers are chemically synthesized oligoDNAs, and these oligoDNAs can be synthesized by using an automated DNA synthesizing hardware, such as the DNA synthesizer Pharmacia LKB Gene Assembler Plus (Pharmacia). The length of the primer so synthesized (sense primer or antisense primer) is preferably the equivalent of about 10~30 nucleotides. The probe for use in said screening is usually labeled but may be an unlabeled one, and the detection may be made either directly or indirectly by specific binding with a labeled ligand. The suitable label and the method of labeling the probe or the ligand are known to those skilled in the art, and the radioactive label, biotin, fluorescent group, chemiluminescent group, enzyme, antibody, etc. which can be incorporated by the known techniques such as nick translation, random priming or kinase treatment are also included in the relevant technology.

The PCR method for use in said detection includes RT-PCR, for instance, and various modifications of PCR which are used in the art can be applied likewise.

It is also possible to detect the wild type p51 gene and/or mutant p51 gene and quantitate the DNAs of these genes. This technology includes but is not limited to the competitive assay such as MSSA [Kinoshita, M. et al., CCA, 228, 83-90 (1994)] and PCR-SSCP which is known to be a mutation detecting technique utilizing the change in mobility associated with a change in the higher-order structure of a single-stranded DNA [Orita, M. et al., Genomics, 5, 874-879 (1989)].

The above analytical methods mentioned by way of example can be carried out as follows. For example, one or a plurality of primers containing the mutation of p51 (e.g. the mutated sequence based on site mutation information obtained from a cancer patient or the like) are first prepared and hybridized with the DNA obtained from a biological sample. Then, the mobility and peak area measured by SSCP analysis of the standard wild type p51 DNA fragment are compared with the mobility and peak area in the test sample as the product of amplification using said primers to thereby detect the mutation in a specific region of p51 and simultaneously quantitate the product of mutation.

The test sample containing the mutant p51 gene to be measured is not particularly restricted inasmuch as it contains said mutant gene, thus including various biological materials such as blood, serum, urine and excised tissues. The mutant p51 gene can be extracted from such test samples, purified and prepared in the routine manner. Therefore, by comparing the mobility of said standard DNA fragment of the invention, as determined in advance, with the mobility of the amplification product in the test sample as obtained in the PCR amplification of the p51 DNA of the test sample using a mutant p51 primer pair, the mutation in a specific region of p51 DNA can be detected expediently and accurately.

Furthermore, when standards established in known steps of quantity are used, the quantitation of the mutant p51 in the test sample can be made at the same time by comparing the peak areas of the standards with the peak area of the amplification product of p51 DNA in the test sample in the PCR amplification step using the mutant primer set mentioned above. The primer set, standards, PCR-SSCP analysis and detection means can be liberally modified by those skilled in the art and the present invention encompasses such modifications, of course, inasmuch as the sequences of the wild type p51 gene and mutant p51 genes are employed.

The above assay technology according to the present invention is now described more specifically. To begin with, the DNA is extracted from the serum of a cancer patient by the routine procedure such as alkali or acid treatment. Then, a primer set comprising a minus chain partial sequence of a defined length consisting in a part of the nucleotide sequence (145-1488) shown under SEQ ID NO:1 and a plus chain partial sequence of a defined length consisting in a part of the fluorescent-labeled nucleotide sequence (145-1488) as well as a heat-resistant DNA polymerase are caused to act on the DNA solution obtained above to amplify the labeled DNA fragment.

On the other hand, one or a plurality of DNA fragments containing a mutant sequence chemically synthesized according to the p51 site mutation information obtained from, for example, a cancer patient are respectively integrated in plasmid vectors and *E. coli* is transformed. After mass culture and purification, the purified recombinant plasmids are used to prepare e.g. $10^3$ copy, $10^4$ copy, $10^5$ copy, $10^6$ copy, $10^7$ copy and $10^8$ copy standards. Said primer set comprising a minus chain partial sequence consisting in a defined partial sequence of said nucleotide sequence (145-1488) and a plus chain partial sequence consisting in a defined partial sequence of the fluorescent-labeled nucleotide sequence (145-1488) as well as a heat-resistant DNA polymerase to amply the labeled DNA fragment. The solution of DNA amplified above is heated at about 95° C. for about 5 minutes, then immediately cooled on ice, and a SSCP analysis is performed using an automatic sequencer, such as ALF Automatic Sequencer (Pharmacia), whereby the fluorescent peak can be detected. Phoresis in this SSCP analysis is performed preferably at about 30° C.±1° C.

The peak (mobility) of the DNA obtained from the patient's serum is compared with the peaks (mobilities) of the standards and the peak in agreement with a standard is ascertained from the migration time. In this manner, the type (kind) of mutation of the patient p51 can be ascertained. Moreover, by calculating the peak areas of standards and constructing a standard curve, the p51DNA can be quantitated from the calculated peak area of the patient's DNA.

(9) Method of Detecting Mutation of the p51 Gene and Various Assay Methods

The present invention, therefore, provides an expedient test protocol for the concurrent detection and quantitation of mutation in a given region of p51 DNA in the test sample through the above measurement.

The assay method of this invention can be carried out conveniently by utilizing a reagent kit for detecting the wild type p51 gene and mutant p51 gene in a sample.

Therefore, the present invention further provides a reagent kit for detection of wild type p51 and mutant p51 characterized by its comprising said wild type p51 DNA fragment and mutant p51 DNA fragment.

This reagent kit, inasmuch as it contains a DNA fragment capable of hybridizing with a part or the whole of the nucleotide sequence (145-1488) shown under SEQ ID NO:2 or its complementary oligonucleotide sequence or a DNA fragment capable of hybridizing with a part or the whole of a mutant sequence of the nucleotide sequence (145-1488) or a nucleotide sequence complementary to said sequence, may contain other components such as a labeling agent, reagents essential to PCR (e.g. TaqDNA polymerase, deoxynucleotide triphosphate, primers, etc.). In lieu of the nucleotide sequence (145-1488) shown under SEQ ID NO:2, the nucleotide sequence (145-2067) shown under SEQ ID NO:5 can be used.

As the labeling agent, a radio isotope or a chemical modifier such as a fluorescent substance can be employed, although the DNA fragment itself may have been conjugated with the labeling agent in advance. Moreover, this reagent kit may further comprise a suitable reaction diluent, standard antibody, buffer, washing solution, reaction stopper, etc. for convenience in carrying out an assay.

The present invention further provides a method of diagnosis using said assay technique and a diagnostic agent and a diagnostic kit for use in said method of diagnosis.

Further, by direct or indirect sequencing of the mutant p51 sequence obtained from the test sample by the above procedure, it is possible to discover novel p51-related genes having high homology to the wild type p51.

The present invention, therefore, further provides a method of screening for human p51-related genes in test samples through the above-described assay and sequencing of mutant p51 DNA in such test samples.

Furthermore, the wild type p51 and/or mutant p51 can be identified by synthesizing the protein encoded by the human p51A gene of SEQ ID NO:1 or the protein corresponding to the amino acid sequence derived from the sequence of SEQ ID NO:1 by deletion, substitution or addition of one or a plurality of amino acids or a partial sequence thereof, or synthesizing the antibody against any of such proteins. Furthermore, in lieu of the protein encoded by said human p51A gene, the protein encoded by the human p51B gene shown under SEQ ID NO:4 can be used.

Therefore, the present invention provides a method for assay of antibodies against wild type p51 and/or mutant p51 and for assay of the antigen. By this assay method, the degree of neoplastic disturbance or the malignancy of a malignant tumor can be estimated based on the change in the wild type p51 protein. The change mentioned above can be determined by p51 sequence analysis by said routine technology but more preferably the change in the p51 protein or the presence or absence of the p51 protein is detected using an antibody (a polyclonal antibody or a monoclonal antibody). A specific example of the assay method of the invention is as follows. With the p51 antibody, the p51 protein can be immunoprecipitated from a solution containing a human biological material isolated from a human being, such as blood or serum, and the antibody can be reacted with the p51 protein on a polyacrylamide gel Western blot or immunoblot. Moreover, with the p51 antibody, the p51 protein in a paraffin section or frozen tissue section can be detected by an immunohistochemical technique. The technology for antibody production and purification is well known in the art and the known techniques can be selectively employed.

The preferred specific modes of practicing the method of detecting the wild type p51 or a mutant thereof include enzyme-linked immunosorbent assay (ELISA) inclusive of the sandwich technique using a monoclonal antibody and/or a monoclonal antibody, radioimmunoassay (RIA), immunoradiomatrix assay(?) (IRMA) and immunoenzymematrix assay(?) (IEMA).

Furthermore, in accordance with the present invention, it is also possible to provide a cell membrane fraction having p51-binding activity for the p51 protein or the p51 receptor present on the cell surface. To acquire said p51 receptor, the labeled p51 protein is conjugated in a biological sample containing the cell membrane fraction, the resulting p51 conjugate is isolated by extraction and purified, and the amino acid sequence of the isolate is determined. The acquisition and sequencing of this p51 receptor protein fall within the expertise of one skilled in the art.

(10) Application to Drug Screening

The present invention can be applied to the screening for compounds (p51 receptor reaction products: the compound may be a low molecular compound, a high molecular compound, a protein, a protein fragment, an antigen, an antibody or the like) by using the p51 receptor polypeptide or a binding fragment thereof for the screening of various drugs. Preferably, the p51 receptor protein is utilized. The p51 receptor polypeptide or its fragment for use in such a screening test may be immobilized on a solid support or used in the form of a suspension in a fluid carried to the cell surface. To mention an example of drug screening, host eucaryotic or procaryotic cells transformed stably with a recombinant polypeptide and expressing the polypeptide or its fragment can be utilized, preferably in a competitive binding assay. Moreover, such cells in the free or immobilized state can be used in a standard binding assay. More preferably, the formation of a complex between the p51 receptor polypeptide or its fragment and a test substance is quantitated to detect the degree of inhibition of said formation of a complex between the p51 receptor polypeptide or fragment and the p51 polypeptide or fragment by the test substance is detected, whereby the screening for a compound can be accomplished.

Thus, the present invention provides a method of drug screening characterized by contacting such a substance with the p51 receptor polypeptide or a fragment thereof by a per se known technique and, then, detecting the presence of a complex between said substance and said p51 receptor polypeptide or fragment or the presence of a complex between said p51 receptor polypeptide or fragment and a ligand. Further, the p51 receptor activity is measured to see whether said substance may antagonize the p51 receptor to exhibit the p51 activities defined hereinbefore, for example the activity to modify the cell cycle or modulate the induction of apoptosis. Specifically, in carrying out such a competitive binding assay, the p51 receptor polypeptide or its fragment is labeled. The free p51 receptor polypeptide or fragment is separated from the protein-protein complex. Then the amount of the free label (non-complex-forming) can be a measure of the binding between the factor to be assayed and the p51 receptor or inhibition of the p51 receptor-p51 polypeptide binding. The small peptide (pseudopeptide) of the p51 polypeptide is thus analyzed, and the one having p51 receptor inhibitory activity is determined.

Another drug screening method of the present invention is a method of screening for compounds having an adequate binding affinity for the p51 receptor polypeptide. Briefly, a large number of different peptide test compounds are synthesized on solid supports such as plastic pins or other surfaces. Then, the peptide test compounds are reacted with the p51 receptor polypeptide, followed by washing. Then, the reacted and bound p51 receptor polypeptide is detected by a per se known technique [PCT: WO84-03564]. The purified p51 receptor can be directly coated on a plate for use in said drug screening. However, the p51 receptor polypeptide can be immobilized on a solid phase by antibody supplementation using a non-neutralizing antibody against the polypeptide. Furthermore, the present invention is directed to a competitive drug screening assay in which a neutralizing antibody specifically binding the p51 receptor polypeptide and a test compound are caused to compete with each other for the binding to the p51 receptor polypeptide or fragment. By this competitive assay using the antibody, the presence of peptides having one or more epitopes or antigenic determinant sites of the p51 receptor polypeptide can also be detected.

Referring, further, to drug screening, a still another method comprises the use of a host eucaryotic cell line or cells containing a nonfunctional p51 gene. Thus, after the host cell line or cells are allowed to grow in the presence of a drug compound for a predetermined time, the proliferation rate of the host cells is measured to see whether the compound may modulate apoptosis or the cell cycle. As a means for measuring the proliferation rate, it is possible to measure the biological activity of the p51 receptor.

Moreover, in accordance with the present invention, for the purpose of developing the more active or stable p51 polypeptide derivatives or drugs which will potentiate or interfere with the function of the p51 polypeptide in vivo, various interactive biologically active polypeptides or structural analogs, e.g. p51 agonists, p51 antagonists, p51 inhibitors, etc., can be constructed. Such structural analogs can be characterized by, for example, analyzing the three-dimensional structures of complexes between p51 and other proteins by X-ray crystallography, computer modeling or a combination of such techniques. Furthermore, the information on structural analogs can also be generated by protein modeling based on the structures of homologous proteins.

The method of obtaining the still more active or stable p51 polypeptide derivatives may for example involve an alanine scan analysis. In this method, Ala is substituted for each amino acid residue and the effect of substitution on peptide activity is determined. Each amino acid residue in a peptide is thus analyzed and the region or regions of importance to the activity or stability of the peptide are determined. By using this method, the more active or stable p51 derivatives can be designed.

It is also possible to isolate the target-specific antibody selected by a functional assay and analyze its crystal structure. As a rule, a pharmacore providing the basis for further drug design can be obtained by this approach. It is possible to identify or isolate a peptide from a chemically or biologically constructed peptide bank by causing formation of an anti-ideotype antibody against a functional pharmacoactive antibody. Therefore, the selected peptide is also expected to serve as a pharmacore.

In this manner, drugs having improved p51 activity or stability or drugs acting as inhibitors, agonists or antagonists of p51 activity can be designed and developed.

In accordance with the cloned p51 sequence, a sufficient amount of p51 polypeptide can be procured and submitted to X-ray crystallographic and other analytical research. Furthermore, the p51 protein having the amino acid sequence of SEQ ID NO:1 as provided by the present invention enables establishment of a computer modeling program which may take the place of X-ray crystallography or supplement the latter technique.

Furthermore, by constructing a human p51 gene-bearing knockout mouse (mutant mouse) in accordance with the present invention, it is possible to detect which sites of the human p51 gene sequence will influence said various p51 activities in vivo, that is to say what functions the p51 gene product and mutant p51 gene products will have in vivo.

This is a technology to intentionally modify the genetic information of organisms by utilizing homologous recombinations of genes, and the method using mouse embryonic stem cells (ES cells) can be mentioned as an example [Capeccchi, M. R. Science, 244, 1288-1292 (1989)].

The method of constructing such mutant mice as above is well known to those skilled in the art, and by applying the human wild-type p51 gene or mutant p51 gene of the present invention to the above technology as modified (Noda, T. (ed.), Experimental Medicine, Supplemental Issue, 14(20) (1996), Yōdo-sha), mutant mice can be easily established. Therefore, by utilizing the above technology, drugs having improved p51 activity or stability or drugs acting as inhibitors, agonists or antagonists of p51 activity can be designed and developed.

The present invention comprises the following.
1. A method of inhibiting tumorigenesis which comprises transferring the p51 gene to tumor cells.
2. A method of inhibiting tumorigenesis which comprises transferring the p51 protein to tumor cells.
3. A pharmaceutical composition comprising the p51 gene or an equivalent thereof and a pharmaceutically acceptable carrier.
4. A pharmaceutical composition comprising the p51 protein or an equivalent thereof and a pharmaceutical acceptable carrier.
5. A drug for gene therapy which comprises the p51 gene or an equivalent thereof as an active ingredient.
6. A cancer diagnostic reagent comprising the p51 gene or an equivalent thereof.
7. A cancer diagnostic reagent comprising the p51 protein or an equivalent thereof.
8. A method of screening for p51- or p53-related genes which comprises using the p51 gene or an equivalent thereof.
9. A method of screening for inhibitors of cell tumorigenesis which comprises using the p51 gene or an equivalent thereof.
10. A method of screening for p51 gene inducers and/or inhibitors which comprises using the p51 gene or an equivalent thereof.
11. Use of a p51 gene inducer and/or inhibitor selected by the above screening in the therapy of diseases arising from p51 gene expression abnormality.

BEST MODE FOR CARRYING OUT THE INVENTION

The following examples and experimental examples are further illustrative of the present invention. It should, however, be understood that the scope of the invention is by no means restricted by these examples and experimental examples.

EXAMPLE 1

Isolation of the Human p51 Gene (1) Cloning and DNA Sequencing of the Human p51 Gene
(a) The present inventors carried out a PCR amplification using the following p73-F1 sense primer and p73-R1 antisense primer and then a second amplification by a nested PCR using the following p73-F2 sense primer and p73-R2 antisense primer.

```
p73-F1:
                                           SEQ ID NO:12)
5'-TA(CGT)GCA(CGT)AAA(G)ACA(CGT)TGC(T)CC-3' p73-R1:
                                          (SEQ ID NO:13)
3'-TGC(T)GCA(CGT)TGC(T)CCA(CGT)GGA(CGT)A(C)G-5' p73-F2:
                                          (SEQ ID NO:14)
5'-TA(CGT)ATA(CT)A(C)GA(CGT)GTA(CGT)GAA(G)GG-3' p73-R2:
                                          (SEQ ID NO:15)
3'-ATGAAC(T)A(C)GA(CGT)A(C)GA(CGT)CCA(CGT)AT-5'
```

More specifically, from the human skeletal muscle polyA+ RNA (Clontech), the cDNA was synthesized using a random primer and an oligo dT primer. Then, a cDNA library consisting of about $10^7$ plaques as constructed using λ ZipLox (Gibco BRL) as the vector was amplified and the DNA was extracted. Using 0.2 μg of the cDNA as the template and said p73-F1 and p73-R1 as primers, an amplification reaction was carried out in 25 cycles of 94° C., 30 sec., 45° C., 30 sec. and 72° C., 30 sec in accordance with the Tag Polymerase (Gibco-BRL) manual. Then, using 1/100 of the amplification product as the template and said p73-F2 and p73-R2 as primers, a further amplification was carried out under the same conditions.

Since a band of 172 bp as deduced from the structure of the p53 gene was obtained, a restriction enzyme cleavage map of the band was prepared. As a result, the presence of a gene other than the p53 gene was detected. This band was subcloned in pGEM7 (Promega) and using ABI377 Automatic Sequencer (ABI), the nucleotide sequence was determined in the routine manner. As a result, it was found to be a DNA fragment derived from a novel gene which resembles the p53 gene but has a different novel nucleotide sequence.

Separately, a similar analysis was carried out using cDNA libraries derived from other organs (e.g. brain). As a result, a DNA fragment derived from a further different novel gene resembling the p53 gene was detected but it was found to be a fragment derived from the p73 gene.

This subcloned DNA fragment was excised and using the BcaBest labeling kit (Takara), a labeled probe was constructed. The plaque hybridization assay of an unamplified library of $2.4 \times 10^6$ plaques as constructed using the oligo dt primer alone in otherwise the same manner as in the construction of said cDNA library gave 8 positive clones. Since λ ZipLox can be easily converted to a plasmid using the Cre-LoxP system, sequencing of the plasmid obtained by conversion was carried out in the routine manner using LICOR's automatic sequencer and ABI377 automatic sequencer (ABI).

Then, between the nucleotide sequence of the gene obtained and the nucleotide sequences of the p53 and p73 genes, a homology search was made with FASTA Program using GCG software (Wisconsin Sequencing Package, Genetics Computer Group) [Person, W. R. and Lipman, D. J., Proc. Natl. Acad. Sci. U.S.A., 85, 1435-1441 (1988)].

As the result of said homology search, two of the clones selected by the above method and sequenced were found to have high homology with respect to the p53 gene and p73 gene. The molecular masses calculated from the deduced amino acids encoded by the gene sequence of these 2 clones were 50,894 Da and about 71,900 Da, respectively. The present inventors named these clones p51A and p51B, respectively.

The full-length nucleotide sequence of the gene (p51A gene) possessed by the p51A clone obtained as above is shown under SEQ ID NO:2 and the full-length nucleotide sequence of the gene (p51B gene) possessed by the p51B clone is shown under SEQ ID NO:5.

As shown under SEQ ID NO:2, the p51A clone was found to have a gene having a nucleotide sequence (1344 nucleotides) coding for the amino acid sequence (448 amino acids) of SEQ ID NO:1 and having an open reading frame in the 145th~1488th position. Moreover, the deduced amino acid sequence encoded by the nucleotide sequence of the gene possessed by this clone had a transcriptional activation domain in the 1st~59th position, the DNA binding domain in the 142nd~321st position, and the oligomerization domain in the 359th~397th position.

On the other hand, as shown under SEQ ID NO:5, the p51B clone was found to have a gene having a nucleotide sequence (1923 nucleotides) coding for the amino acid sequence (641 amino acids) of SEQ ID NO:4 and having an open reading frame in the 145th~2067th position. Moreover, the deduced amino acid sequence encoded by the nucleotide sequence of the gene possessed by this clone had a transcriptional activation domain in the 1st~59th position, a DNA binding domain in the 142nd~321st position, and an oligomerization position in the 353rd~397th position. Furthermore, this sequence was found to have an additional sequence (SAM domain) in the C-terminal region and the 353rd~641st region inclusive of this additional sequence could be regarded as an oligomerization domain in a broad sense of the term.

The amino acid sequence encoded by the p51A gene of the invention was compared with the amino acid sequences of the p53 protein and p73β protein for homology comparison among the three sequences (FIG. 2). In the diagram, the amino acids common to the 3 sequences are boxed.

FIG. 1 is a schematic diagram showing features of the structural domains of the p51A protein along with those of the p53 protein and p73β protein. In the diagram, "TA" represents a transcriptional activation domain, "DNA binding" represents a DNA-binding domain, and "Oligo" represents an oligomerization domain. The structural features of the p51 protein and p73β protein were deduced from the structural features of the p53 protein.

As a result, the homology of the deduced amino acid sequences of the p51A protein, p53 protein and p73β protein in each of full-length sequence, transcriptional activation domain, DNA-binding domain, and oligomerization domain was respectively as follows: between p51A protein and p53 protein, 36%, 22%, 60% and 37%, respectively; between p51A protein and p73 protein, 42%, 30%, 87% and 65%, respectively; and between p53 protein and p73 protein, 28%, 27%, 63% and 83%, respectively (Table 1).

Moreover, although the 448 residue-structure of the p51A protein was shorter than the 636 residue-structure of the p73α protein, the total structure of the p51A protein resembled the p73 protein with the C-terminal region split off.

These results indicated that although the putative amino acid sequence of the p51A protein resembles the deduced sequences of both the p53 protein and p73β protein, its homology to the amino acid sequence of the p73β protein is higher than its homology to the p53 protein and that the homology between p51A protein and p73β protein is higher than the homology between p53 protein and p73β protein in the regions other than the oligomerization domain. Furthermore, between p51A protein and p73β protein, a homology was found in the region where no homology was found between p53 protein and p73β protein or between p53 protein and p51A protein. These results suggest that, on the amino acid sequence level, the p51A protein can be said to be closer to the p73β protein than to the p53 protein.

Similarly, the amino acid sequence encoded by the p51B gene of the invention was compared with the amino acid sequence of the p73α protein for homology comparison (FIG. 3). In the diagram, the amino acids common to the two sequences are boxed.

Figure 4:
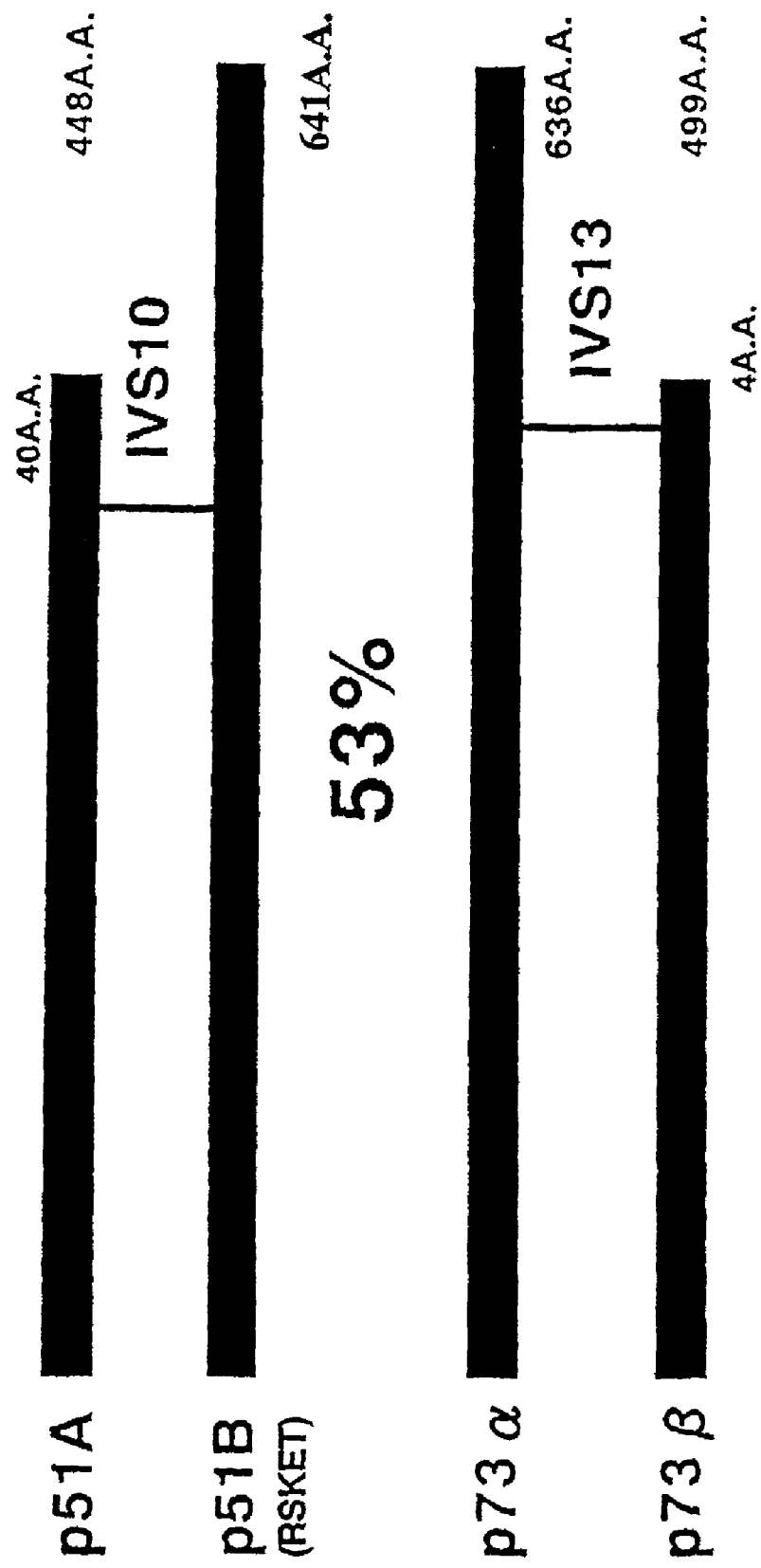
FIG. 4 is a schematic diagram comparing the structure of the alternative splicing variant (p51A, p51B) of the p51 protein with the structure of the alternative splicing variant (p73α, p73β) of the p73 protein.

FIG. 4 is a schematic diagram showing features of the structural domains of splicing variants encoded by the p51 (A and B) genes along with those of the p73 proteins (α and β). Whereas the divergence point between p51A protein and p51B protein begins at intron 10 and the divergence point between p73α protein and p73β protein begins at intron 13.

EXAMPLE 2

Confirmation of p51mRNA Expression in Normal Human Tissue (1) Northern Blot Analysis Expression of p51mRNA in normal human tissue was assessed by Northern blotting using, as the probe, a human cDNA clone labeled by the random oligonucleotide priming method.

Northern blot analysis was carried out using Human Multiple Tissue Northern Blot (Clontech, Palo Alto, Calif., U.S.A.) in accordance with the product manual.

Thus, the EcoRI fragment (600 bp: corresponding to the 5' end of cDNA) of a PCR amplification product of the DNA clone obtained in Example 1 was labeled with [$^{32}$p]-dCTP (Random Primed DNA Labeling Kit, Boehringer Mannheim) for use as a probe.

Blotting was made using ExpressHyb Hybridization Solution (Clontech) under the conditions directed in the user manual, and detection was made using BAS2000 (FUJI).

Figure 5:
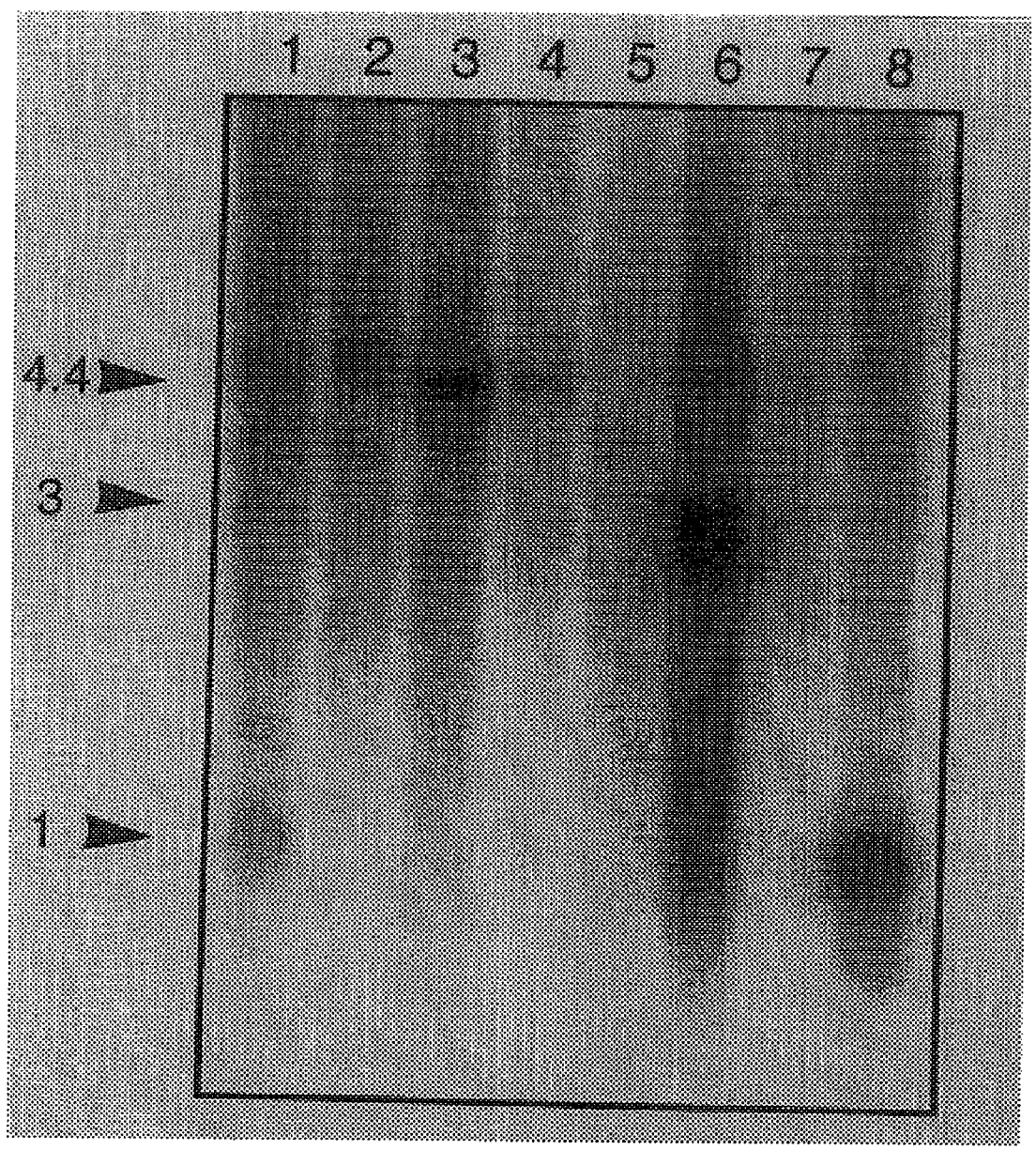
FIG. 5 is a photograph, in lieu of a drawing, which shows the pattern of expression of p51mRNA in various human tissues as a Northern blotting (using a Clonetech's filter) electrophoretogram. The lanes represent the results for 1: heart, 2: brain, 3: placenta, 4: lung, 5: liver, 6: skeletal muscle, 7: spleen, 8: pancreas, respectively.
Figure 6:
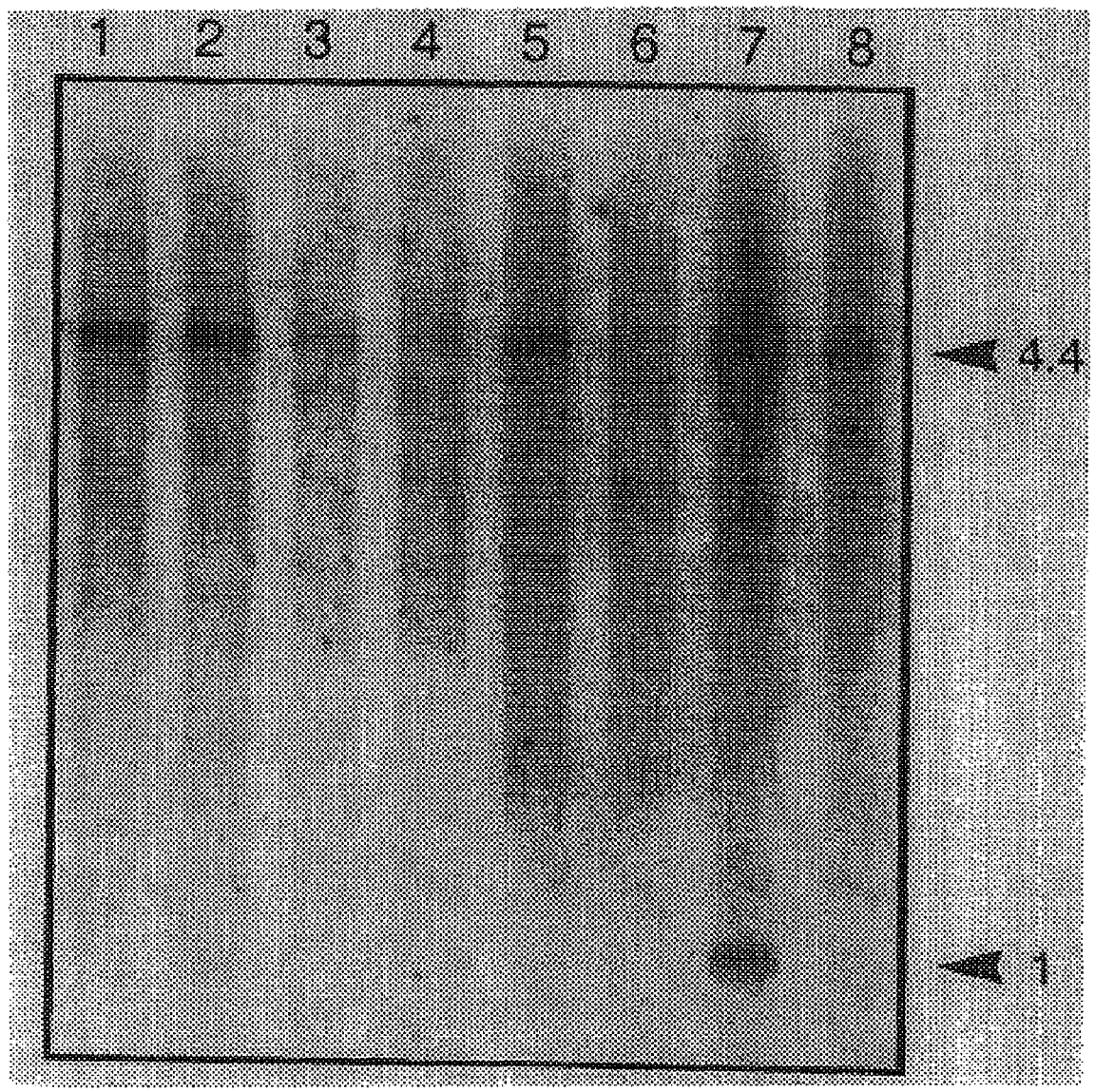
FIG. 6 is a photograph, in lieu of a drawing, which shows the pattern of expression of p51mRNA in various human tissues as a Northern blotting (using a filter prepared by using the RNA purchased from Clontech) electrophoretogram. The lanes represent the results for 1: mammary gland, 2: prostate, 3: salivary gland, 4: stomach, 5: thymus, 6: thyroid, 7: trachea, and 8: uterus, respectively.

The results are shown in FIG. 5 and FIG. 6.

FIG. 5 shows the result of Northern hybridization carried out with the filter purchased from Clontech, and FIG. 6 shows the result of Northern hybridization carried out with a filter constructed by the present inventors using the RNA purchased from Clontech. FIG. 5 shows the electrophoretogram with 2 μg poly A−RNA added for each lane, and FIG. 6 is the electrophoretogram with 0.5 μg poly A+RNA added for each lane.

The lanes in FIG. 5 represent the result for 1: heart, 2: brain, 3: placenta, 4: lung, 5: liver, 6: skeletal muscle, 7: spleen, and 8: pancreas. The lanes in FIG. 6 represent the result for 1: mammary gland, 2: prostate, 3: salivary gland, 4: stomach, 5: thymus, 6: thyroid, 7: trachea, and 8: uterus.

It was found that the distribution of expression of the mRNA (4.4 kb) of the gene named "human p51 gene" according to the present invention was rather confined in contrast to the ubiquitous expression of p53 mRNA, with the expression level being highest in skeletal muscle, seconded by placenta, and decreased progressively in placenta, trachea, mammary gland, prostate, salivary gland, thymus, uterus, stomach, lung, brain and heart in the order mentioned. In other tissues (e.g. adrenal gland, small intestine, spinal cord, spleen), no expression of p51mRNA could be detected.

The expression pattern of the p73 gene is also tissue-restricted. However, it was found that while the expression of p51 gene overlapped the expression of the p73 gene (expression in the same tissue), the distribution of expression was broader than the distribution of expression of the p73 gene.

The above difference in expression tissue distribution among the human p51 gene, p53 gene and p73 gene suggested that notwithstanding the resemblance in biological activity among these genes, they are dissimilar in function depending on tissues in vivo.

Further research also revealed that, in various human tissues, the p51mRNA, as in the case of p73 protein, exists in selectively spliced forms (alternative splicing variants), namely a short form encoding the p51A protein and a long form encoding the p51B protein. The latter long form encoding p51B was found to have homology to the factor named ket which had been accidentally discovered in a search for the glutamate receptor of the tongue. The 3 kb mRNA, which is a main transcript in skeletal muscle, was the most abundant mRNA observed in all the tissues investigated. The short-form cDNA clone was suspected to be derived from this transcript. Interestingly, in contrast to the mRNA observed in normal tissues, this short-form (p51A) of p51mRNA was found to have been expressed in many tumor cell lines.

FIG. 4 is a schematic diagram comparing the structures of the respective alternative splicing variants of the p51 protein and p73 protein. This p51BmRNA encoded a protein having a molecular mass (calculated) similar to that of p73α.

Functional differences between p51A and p51B remain unknown.

EXAMPLE 3

Chromosome Mapping of the p51 Gene

Using a radiation hybrid panel (GeneBridge 4 Radiation Hybrid Panel; Research Genetics), the p51 gene was mapped on the human chromosome. As a result, the p51 gene was localized in the 3q28-ter region between the markers AFBM327YD9 and WI-1189 (5.66cR from the former marker).

EXAMPLE 4

Mutation of p51 in Various Human Cancer Cell Lines and Human Tumors

The most intriguing question about the p51 gene is the question of whether the features of the p53 tumor suppressor gene are shared by the p51 gene as well as the relationship of a mutation of the present gene with the morphogenesis of a human tumor.

Therefore, using various tumor cell lines, a search was made for the presence or absence of mutation of the p51 gene. For this search, the method for functional analysis of separated alleles in yeasts (FASAY), which was previously used by the present inventors in the identification and characterization of p53 mutation, was used [Ishioka et al., Nat. Genet. 5, 124-129 (1933)].

A complementary full-length DNA fragment coding for the human p51A gene was amplified by the same PCR method as used in the determination described hereinbefore to acquire the nucleotide sequence of the amplification product covering the full-length sequence encoding the p51A gene and this nucleotide sequence was determined by direct sequencing to detect the presence or absence of a mutation.

Tumor cells were respectively cultured in Dulbecco's Modified Essential Media supplemented with 10% fetal calf serum in a 5% $CO_2$ environment. Since all the p51AcDNA clones could amplify the p53cDNA in the previous analysis, the quality of cDNAs of cell lines was guaranteed.

Of 102 cell lines, 67 lines analyzed were capable of amplifying the p51A DNA fragment. The nucleotide sequence was determined by direct sequencing for 35 of the above cell lines.

Mutations were found in two cell lines, namely Ho-1-u-1 (JCRB0828), which is a head-and-neck cancer cell line, and SKG-IIIa (JCRB0611), which is a cervical cancer cell line.

The mutation was $Ser^{145} \rightarrow Leu$ in the former and $Gln^{165} \rightarrow Leu$ in the latter. With regard to the p53 protein, it was likely that the normal function of the p53 protein had been defected by mutation in the former and by human papilloma virus infection in the latter. Moreover, in the mRNAs derived from tumor cells, various splicing variants were noted.

Referring to human primary cancers, the nucleotide sequences of the DNA amplification products obtained by SSCP and RT-PCR techniques were determined by direct sequencing in search for p51A gene mutation. In a total population of 66 human tumor cases, namely 8 neuroblastoma cases, 8 colon cancer cases, 8 breast cancer cases, 8 lung cancer cases, 8 brain tumor cases, 8 esophageal cancer cases, 8 hepatocellular cancer cases, 6 pancreatic cancer cases, and 4 renal cancer cases, a mutation of $Ala^{148} \rightarrow Pro$ was detected in one lung cancer case.

The analysis of the above 3 cases was invariably an analysis of cDNA and it was clear that the expression originated from a single chromosomal locus.

EXPERIMENTAL EXAMPLE 1

Suppression of Colony Formation by p51 Transformation

The p53 protein has an ability to block cells in the G1 phase or induce apoptosis.

To investigate the colony formation inhibitory activity of the p51 protein of the invention, the SAOS2 osteosarcoma cell line (accession number: ATCC HTB85) was co-transfected with a puromycin-resistant expression plasmid (pBA-BEpuro: Morgenstern J. Nuc. Acids Ru, 18, 3587, 1990) as well as a p51A expression construct, an HA-labeled p51A expression construct (HA-labeled ATGTATCCATATGAT-GTTCCAGATTATGCT (SEQ ID NO:16), which codes for the amino acid sequence MYPYDVPDYA (SEQ ID NO:17)), a p53 expression construct, and a vector and the colony-forming ability was evaluated.

The above expression vectors were constructed by cloning the coding region fragment of p51A DNA (2816 nucleotides; in SEQ ID NO:2, oligonucleotide numbers 1~2816), the fragment prepared by adding the HA tag to the p51A cDNA, and the coding region fragment of p53cDNA (1698 nucleotides; nucleotide numbers 62~1760), respectively. Then, the osteosarcoma cell line SAOS2 was cultured in Dulbeccos's Modified Essential Medium supplemented with 10% fetal calf serum in a 5% $CO_2$ environment. A 6 cm dish was seeded with the above SAOS2 cells ($1\times10^6$ cells/dish) and, after 24 hours, the cells were transfected with a wild-type p51 expression vector containing the p51A cDNA chain (pRcCMV/p51A). Similar transformations were carried out using the HA-tagged p51A cDNA, the wild-type p53 gene and, as control, the pRcCMV expression vector alone.

Using Mammalian Transfection Kit (Stratagene), 1 μg of pBABEpuro was introduced into the cells. The resulting cells were fixed and stained with Crystal Violet. The stained colonies were photographed. Each transfection was carried out twice for analyzing colony formation.

Figure 7:
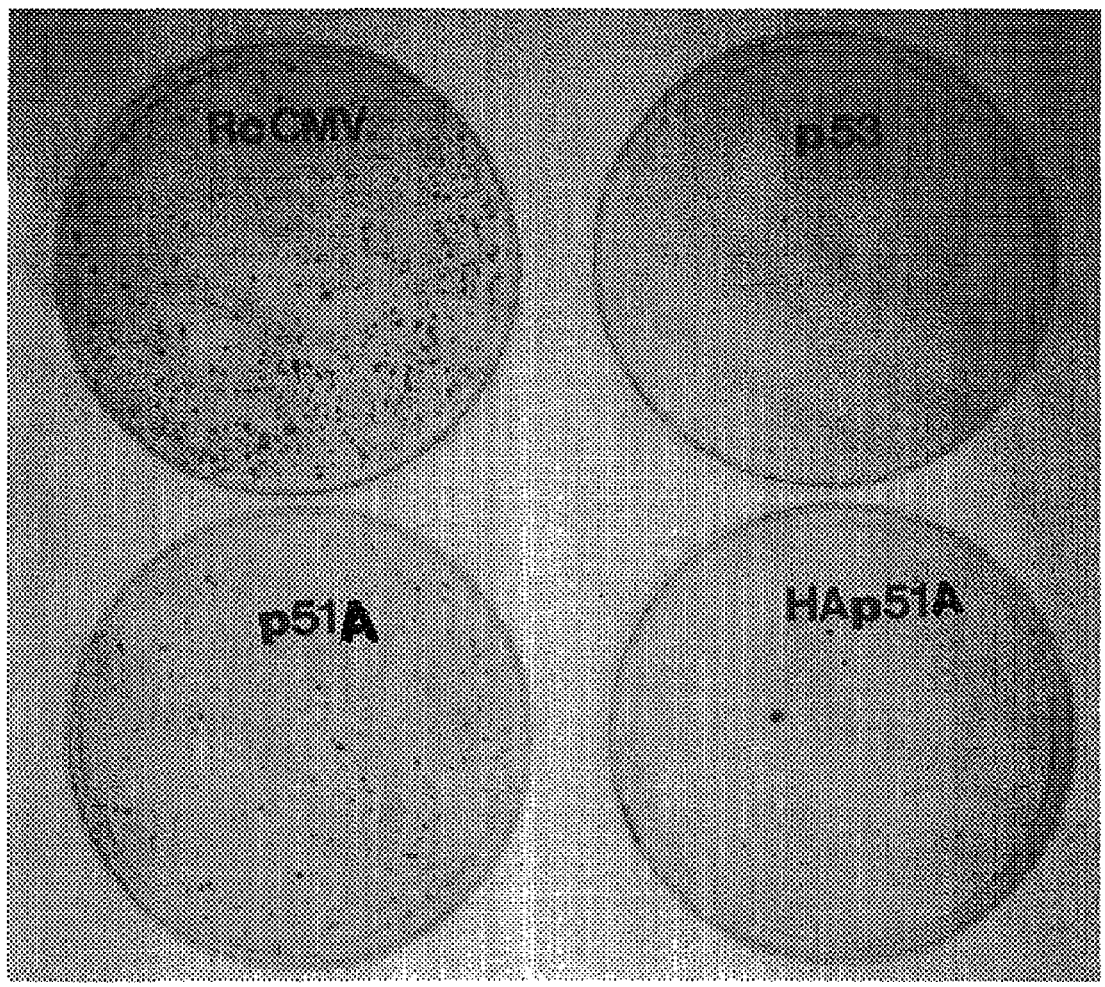
FIG. 7 is a photograph, in lieu of a drawing, which shows the anti-colony forming activity of the p51A gene. More specifically, it is a photograph, in lieu of a drawing, which shows in comparison the colony forming activities of the cells transformed with the p51A expression plasmid (p51A), p53 expression plasmid (p53), HA-tagged p51A expression plasmid (HAp51A), and vector (RcCMV) alone, respectively.

As a result, significant decreases in the number of colonies were observed in the culture dishes of p53 gene-transfected cells and p51 gene-transfected cells. In contrast, in the culture dish of cells treated with the vector alone, growth of a large number of colonies was observed. The p51 gene was thus found to have an ability to suppress colony formation but this ability was slightly poor as compared with the ability of the p53 gene. On the other hand, the HA-tagged p51 gene showed a colony formation-suppressing ability comparable to that of the p53 gene (FIG. 7).

EXPERIMENTAL EXAMPLE 2

Test of the Transcriptional Activation Function of the p51 Protein

Since the activity of the p53 protein to arrest cell growth in G1 phase or induce apoptosis was dependent on the transcriptional activation function of the p53 protein, a test was carried out to see whether the p51 protein would exhibit such activity.

Downstream of the Waf1 promoter, which is known to be controlled by p53 transcriptional activation function, and RGC (ribosomal gene cluster) sequence, a luciferase reporter plasmid as well as a p51A gene expression construct was introduced by the method described in Example 5. Specifically, SAOS2 cells were co-transfected with said luciferase reporter plasmid and the p51A expression vector, p53 expression vector or control vector and the luciferase activity of the lysate obtained from the resulting transformant was assayed. The luciferase activity was calculated with a dual luciferase reporter assay system (ProMega) taking the transfection efficiency into consideration.

Figure 8:
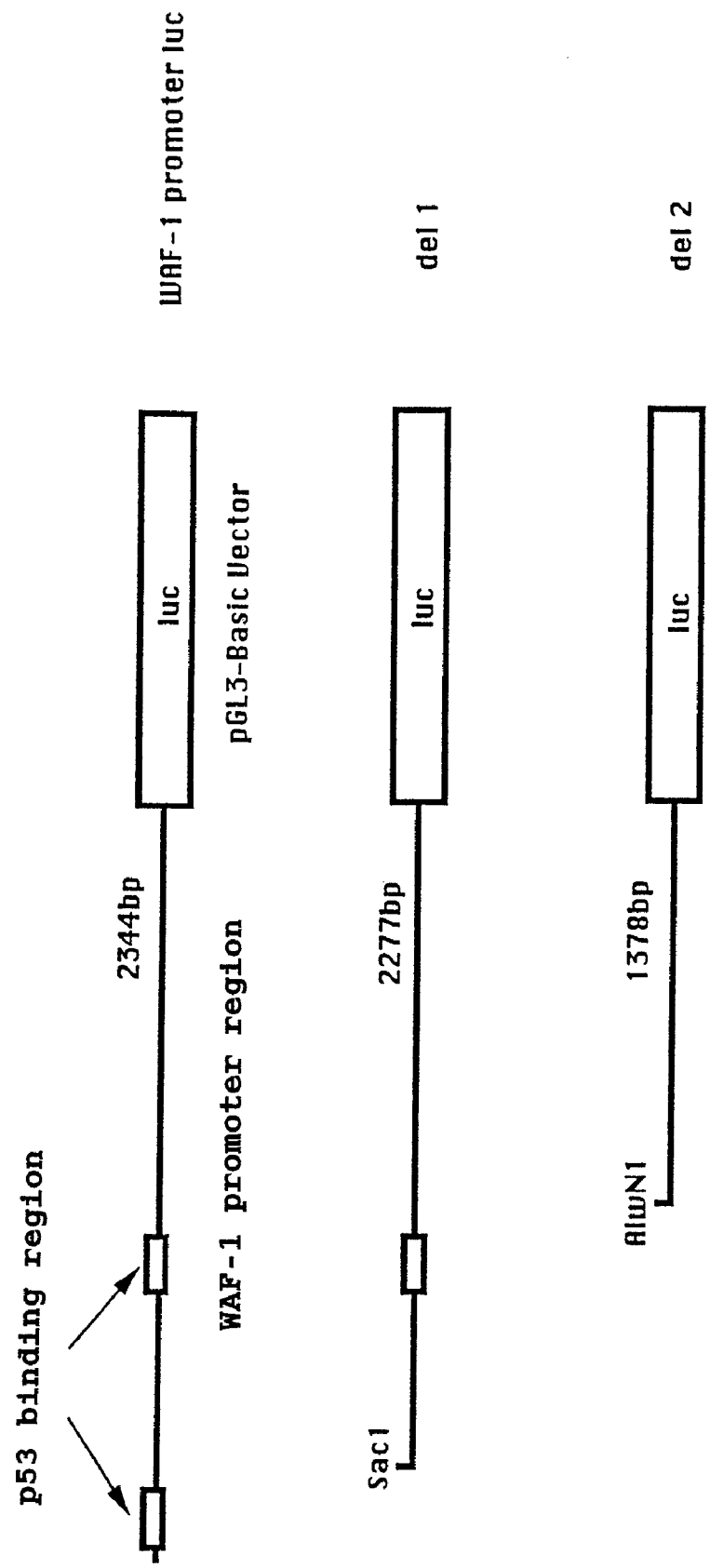
FIG. 8 is a schematic diagram showing the reporter constructs used in Experimental Example 2. In the diagram, "WAF-1 promoter luc" represents a wild type p21WAF1 promoter construct with two p53 regulating elements retained; "del 1" represents a similar construct in which one upstream element has been deleted; and "del 2" represents a construct in which both elements have been deleted.

FIG. 8 is a schematic diagram showing the reporter construct used in the experiment. Shown in the diagram are 3 luciferase gene constructs each linked downstream of various p21WAF1 promoters. In the diagram, "WAF-1 promoter luc" represents a wild-type p21WAF1 promoter construct retaining the two p53 control elements; "del 1" represents the construct deprived of the upstream one of said elements; and "del 2" represents the construct deprived of both of said elements.

Figure 9:
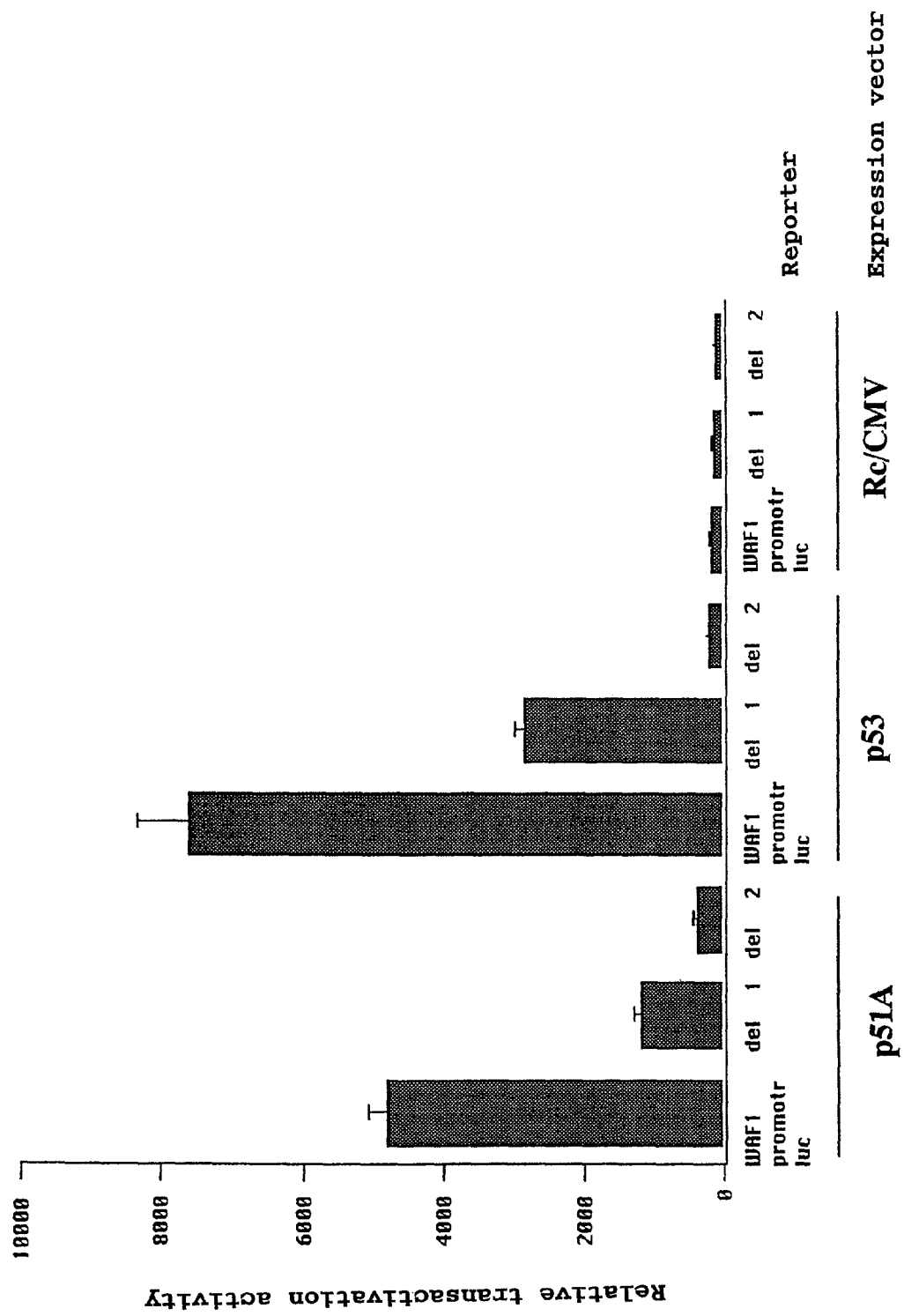
FIG. 9 is a diagram showing the transactivation activity found in the transfer of the p51A expression plasmid (p51A), p53 expression plasmid (p53) or control vector (Rc/CMV) harboring the various reporter constructs shown in FIG. 8 into SAOS2 cells [cf Experimental Example 2].
Figure 10:
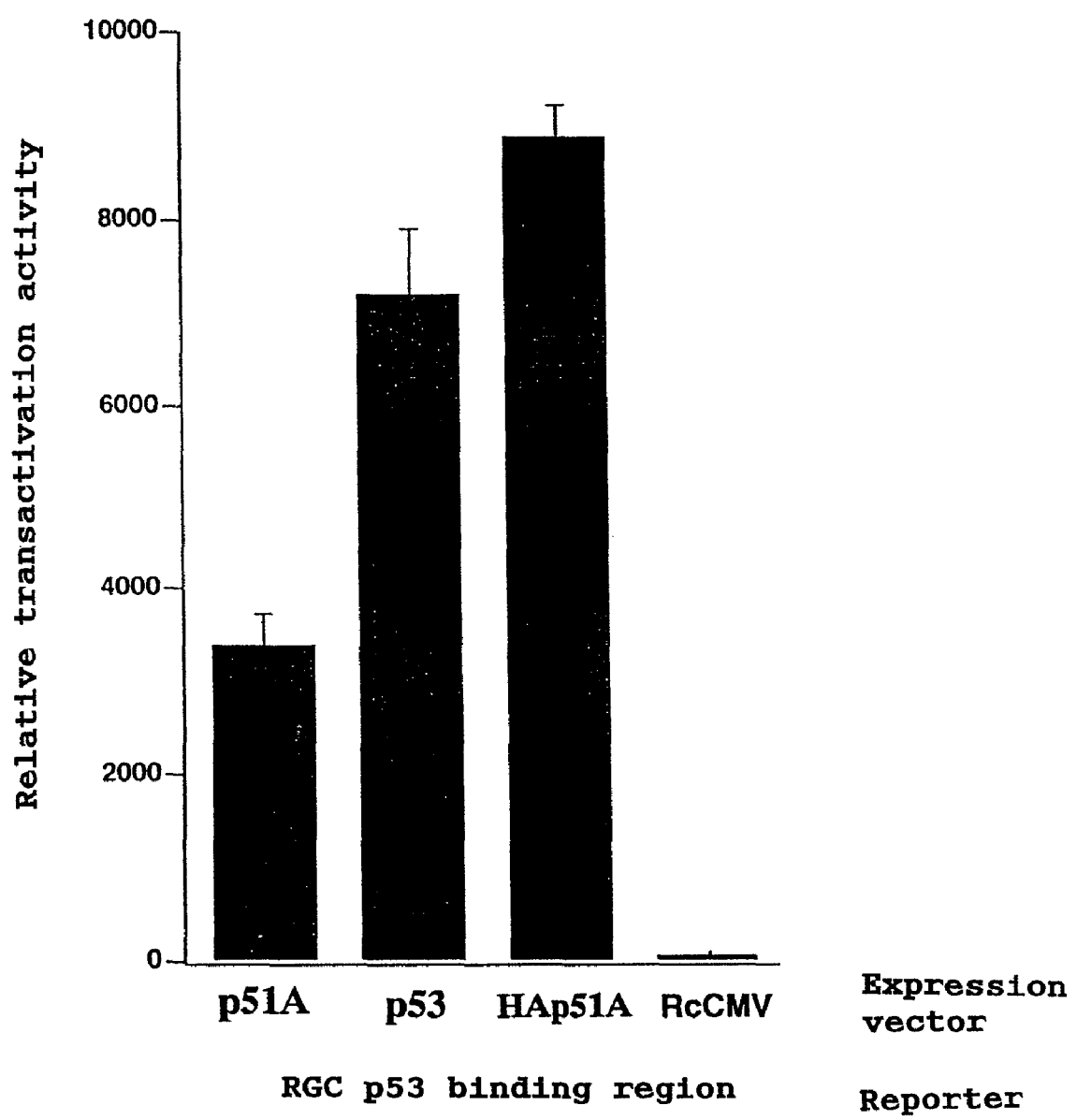
FIG. 10 is a diagram showing the transactivation activity found in the transfer of the p51A expression plasmid (p51A), HA-labeled p51A expression plasmid (HAp51A), p53 expression plasmid (p53) or control vector (Rc/CMV) harboring the PGC reporter construct, whose p53 response has been experimentally demonstrated, into SAOS2 cells [cf Experimental Example 2].

The results are shown in FIG. 9 and FIG. 10. Relative activity on the ordinate represents the luciferase activity calculated by using the dual luciferase reporter assay system taking the transfection efficiency into consideration.

FIG. 9 shows the transactivation activity found when the p51 expression plasmid (p51A), the p53 expression plasmid (p53) or the vector (Rc/CMV) only, which has been linked to each of the various reporter constructs shown in FIG. 8, was introduced into SAOS2 cells. The results showed that like the p53 protein, the p51 protein has activity to induce the number-dependent expression of the p53 reactive sequence.

FIG. 10 shows the results of a similar experiment using the p51A expression plasmid (p51A), the HA-tagged p51A expression plasmid (Hap51A), p53 expression plasmid (p53) or the vector (RcCMV), which has been linked to the PGC reporter construct which has been experimentally demonstrated to have p53 reactivity. As in the experiment shown in FIG. 9, the above results indicated that both p51A and HAp51A, like p53, have activity to induce the number-dependent expression of the p53 reactive sequence. The weak activity found when the p51A expression plasmid was used may be attributed to the fact that since this plasmid was built into the expression vector with the leader sequence retained, the amount of expression was small.

When the leader sequence was removed in a later experiment, the p51A protein showed a stronger expression-inducing action than the p53 protein and, in said colony formation-inhibition assay, too, this protein was found to have strong activity.

It is apparent from the above results that the p51 protein had the ability to induce transcription through its transcriptional regulation domain. The finding that the transcriptional activity was lost on induced mutation of this element suggests that the p51 protein also utilizes the same recognition sequence as does the p53 protein.

Then, it was inquired whether the same transcription relation holds true in vivo, too. A p51A gene expression construct having an HA-tagged epitope was introduced into SAOS2 cells over a short time. The finding of the uptake of the p51A gene by cells indicated that p51A is localized in the nucleus and all the cells were found to elevate the level of p21Waf1. This indicates that the p51 protein is also capable of inducing p21Waf1 which is known to be controlled by the p53 protein.

EXPERIMENTAL EXAMPLE 3 p51 Gene Mutation in Tumors in situ

The mutation of the p51 gene was investigated in the in situ cancer cells of 66 patients (neuroblastoma, 8 cases; colon cancer, 8 cases; breast cancer, 8 cases; lung cancer, 8 cases; brain tumor, 8 cases; esophagus cancer, 8 cases, hepatocytoma, 8 cases; pancreatic cancer, 6 cases, and renal cancer, 4 cases) by the reverse transcription PCR single-stranded structure polymorphism (RT-PCR-SSCP) method and DNA sequencing method.

(1) Preparation of RNA

Fresh tumor samples were surgically isolated, immediately frozen and stored at −80° C. until used. The RNA was extracted by the method described in the report of Nakagawa et al. [Nakagawa, A., et al., N. Engl. J. Med., 328, 847-854 (1993)].

(2) RT-PCR-SSCP and DNA Sequencing

The total RNA, 5 μg, was transcribed on cDNA using Superscript II reverse transcriptase (Gibco-BRL) and random primers. The 20th cDNA of this reaction product was used for PCR amplification. PCR-SSCP was performed in accordance with the method of Mashiyama et al. [Mashiyama S. et al., Oncogene, 6, 1313-1318 (1991)]. Specifically, the PCR product was amplified using 3 primers for p51A cDNA.

The nucleotide sequences of primers used for PCR are as follows.

```
p51-F1:  5'-AAAGAAAGTTATTACCGATG-3'   (SEQ ID NO:18)
p51-R1:  5'-CGCGTGGTCTGTGTTATAGG-3'   (SEQ ID NO:19)
p51-F2:  5'-CATGGACCAGCAGATTCAGA-3'   (SEQ ID NO:20)
p51-R2:  5'-CATCACCTTGATCTGGATG-3'    (SEQ ID NO:21)
p51-F3:  5'-CCACCTGGACGTATTCCACT-3'   (SEQ ID NO:22)
p51-R3:  5'-TGGCTCATAAGGTACCAG-3'     (SEQ ID NO:23)
```

```
                          -continued
p51-F4:  5'-CATGAGCTGAGCCGTGAAT-3'    (SEQ ID NO:24)

p51-R4:  5'-TATCTTCATCCGCCTTCCTG-3'   (SEQ ID NO:25)

p51-F5:  5'-ATGAACCGCCGTCCAATT-3'     (SEQ ID NO:26)

p51-R5:  5'-GTGCTGAGGAAGGTACTGCA-3'   (SEQ ID NO:27)

p51-F6:  5'-TGAAGATCAAAGAGTCCCTG-3'   (SEQ ID NO:28)

p51-R6:  5'-CTAGTGGCTTTGTGCCTTTG-3'   (SEQ ID NO:29)
```

Then, the 32PdCTP was diluted 1:10 with loading buffer. After 5 minutes of further denaturing at 98° C., the separation was carried out on 5% glycerol/5% polyacrylamide gel at 200 volts at room temperature for 12~14 hours. After the electrophoresis, the gel was dried and exposed against X-ray film overnight so that the migration bands would be definitely visible. To confirm the presence or absence of mutation, the PCR product was subcloned into the pGEM-T Easy Vector (Promega), followed by sequencing with ABI377 DNA sequencer.

As a result, in the lung cancer tissue belonging to the type of highly differentiated squamous cell cancer, an amino acid substitution point mutation (Ala$^{148}$→Pro) was found in the deduced DNA binding region of the p51A protein. This tumor showed paratracheal lyphnode metastasis and pleural invasion. Since all of randomly selected 5 clones had the same mutation, the p51 gene possessed by this tumor cell was suggested to be a single allele or have been expressed mono-allelically.

EXPERIMENTAL EXAMPLE 4

Induction of Apoptosis by p51cDNA Introduction

It was explored whether, like the p53 protein, the p51 protein would induce cell apoptosis.

The apoptosis induction test with the p51 protein was carried out by the method of the present inventors, namely the method which, as mentioned above, comprises the use of a transgenic mouse erythroleukemia cell line (1-2-3 cell line) which presents with typical features of apoptosis when cultured at 32° C. [Kato, M. V., et al., Int. J. Oncol., 9, 269 (1996)].

This mouse erythroleukemia cell line (1-2-3 cell line) was established from the erythroleukemia derived from Friend spleen focus forming virus gp55 gene-transgenic mice [Xu et al., Jpn. J. Cancer Res. 86, 284-291 (1995); Kato et al., Int. J. Oncol. 9, 269-277] and is a cell strain which expresses only a temperature-sensitive (ts) mutant p53 protein (Ala1353Val: point mutation). This ts-mutant p53 protein is localized in the cytoplasm at 37° C., which is a usual culture temperature, and, therefore, does not exhibit the control function of the p53 molecule which is intrinsically discharged in the nucleus but at 32° C. it migrates into the nucleus so that the p53 activity is induced [Levine, A. J. et al., Nature 351, 453-456 (1991)]. It has been already reported that, in this cell line, slow apoptosis is induced at 32° C.

The 1-2-3 cells were cultured in RPMI 1640 medium supplemented with 10% fetal calf serum in a 5% $CO_2$ environment. Then, using pRc/CMV as the expression vector, the p51A gene was introduced into the above cells. The cells were then cultured in a selective medium, and using neomycin resistance (Neo$^r$) as the test, G418-resistant cells were selected. An apoptosis induction study was then carried out in the p51A-expressing cells.

Thus, two strains of p51A-transfected 1-2-3 cells (hereinafter referred to as "1C1 cells" and "4B1 cells") as transfected with the p51A gene-harboring expression vector (pRcCMV/p51A) and, as control, 1-2-3 cells transformed with the vector alone and not containing the p51A gene were respectively seeded on 10 cm (dia.) plates at a concentration of 1×10$^5$/ml and cultured at 2 alternative temperatures of 37° C. and 32° C. for 24 hours. The cells were then harvested and treated with proteinase K and Rnase A to prepare DNA samples. The DNA samples were subjected to agarose electrophoresis. The ethidium bromide-stained images are shown in FIG. 11.

Figure 11:
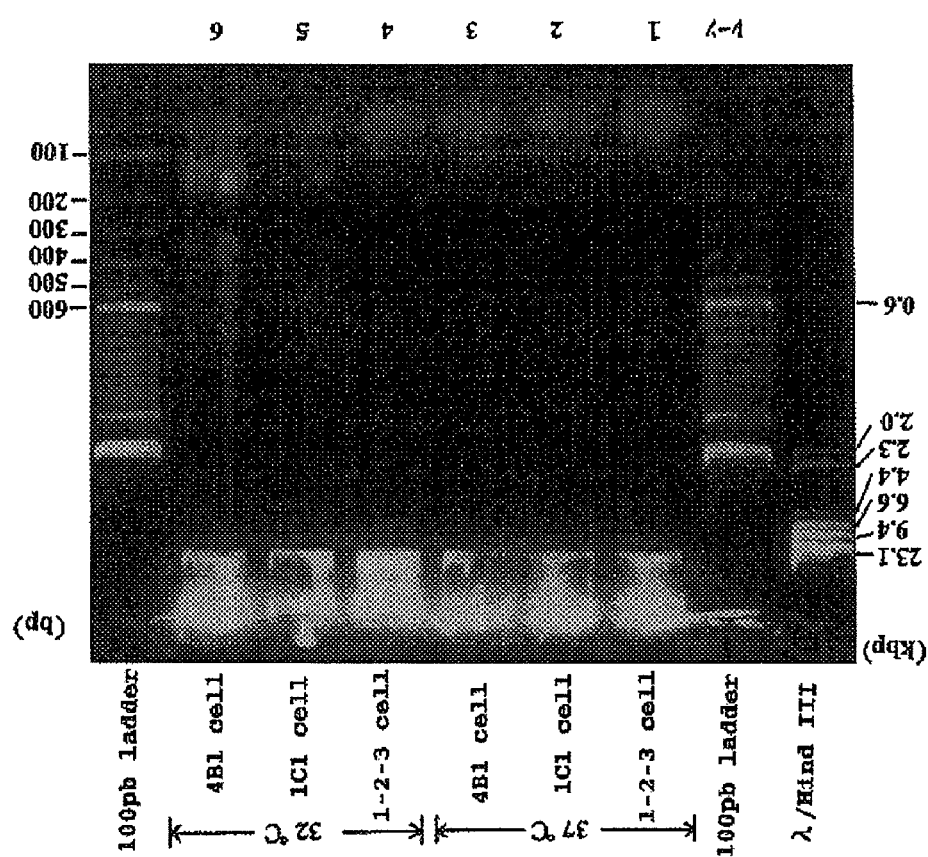
FIG. 11 is a photograph (an ethidium bromide-stained agarose gel electrophoretogram), in lieu of a drawing, which shows the results of DNA fragmentation assays performed with 1C1 and 4B1 cells containing the human p51A gene and 1-2-3 cells not containing the p51A gene as grown at different temperatures of 32° C. and 37° C.

As can be seen in FIG. 11 that, in culture at 37° C., whereas no DNA fragment was detected in 1-2-3 cells (lane 1), DNA fragmentation to 180 bp oligomers could be detected in the p51A gene-transfected 1C1 and 4B1 cells (lanes 2 and 3).

In culture at 32° C., DNA fragmentation was detected in 1-2-3 cells (lane 4) and the DNA fragmentation was promoted in 1C1 cells and 4B1 cells (lanes 5 and 6). These results were consonant with the results of morphological observation of apoptosis and the results of the growth inhibition test of p51-introduced cells (32° C., 37° C.).

The presence or absence of apoptotic morphological changes in cells was studied by fixing the respective cells on glass slides and, after Gimsa staining, observing the cell morphology and the degree of staining microscopically. The viable count of cells was found by Trypan Blue staining and counting.

As a result, the cells grown at 32° C. had surface projections and presented with a shrunken, strained or constricted form. Moreover, in Gimsa-stained cell specimens, chromatin condensation was observed either around the nuclear envelope or in intracellular masses. In contrast, in the cells cultured at 37° C., no such morphological change was observed.

Within 24 hours of culture at 32° C., cells undergoing apoptotic death and cells continuing the cell cycle and growth were mixedly present, and after 24 hours the viable cell count of p51-expressing cells was 10$^5$/ml and the cell count of 1-2-3 cells was 1.7×10$^5$/ml.

The foregoing indicated that the p51 gene-containing cells treated at the temperature of 32° C. experienced a sudden apoptosis in the presence of p53. It was thus confirmed that the p51 protein, like the p53 protein, induces apoptosis in a significant measure.

EXPERIMENTAL EXAMPLE 5

A specific antibody against the C-terminal region (570th~641st positions of the amino acid sequence) of the human p51B protein was prepared and human cells were immunostained.

Thus, the coding region (the 1851st~206th positions of the nucleotide sequence) of the human p51B DNA was ligated to the GST fusion protein expression vector pGEX-1λT (Pharmacia) and a fusion protein was synthesized in *Escherichia coli*. Using this fusion protein and BALB/C mice, an antiserum (polyclonal antibody) was prepared in the routine manner and absorbed with the GST protein to provide a specific antibody against the C-terminal region of the p51B protein.

The above antibody was subjected to a primary reaction with a human skin tissue frozen specimen and then to a secondary reaction with a fluorescent-labeled goat anti-mouse IgG antibody.

As a result, this antibody specifically stained the cell nucleus from the spinal cell layer to the basement layer of the human skin. This specificity was found because said fusion protein treatment abolished this reaction while the pretreatment with GST protein failed to abolish the reaction.

INDUSTRIAL APPLICABILITY

The genes of the present invention can be characterized as related genes of the p53 gene which is known as a tumor suppressor gene. With these genes, the expression levels and functions in cells can be analyzed and it is expected that by analyzing their expression products, morbidities in various diseases associated with these genes (for example, malignant tumors) can be elucidated and diagnostic and therapeutic modalities can be established.

Furthermore, the genes of the present invention are expressed in the gland tissues (prostate, mammary gland), muscle tissues, and thymus and other immune systems in contrast to p73 which is expressed in the nervous system and are likely to be involved in abnormalities of these tissues. Therefore, it is expected that these genes will contribute to the development of inhibitors or suppressants of such abnormalities.

In accordance with the present invention, there is provided a novel human p51 gene which is of value as a cell proliferation suppressive gene. The novel gene of the present invention resembles the gene coding for the p53 protein or p73 protein. Therefore, the gene of the invention can be utilized in studies on the relationships of the analyzed functions of these related genes to various diseases and used in studies for application to gene diagnosis and the medicinal use of these genes in various diseases. Moreover, by using the gene of the invention, the expression pattern of the gene in various human tissues can be explored and its functions in the human body can be analyzed.

In addition, with this gene, the human p51 protein encoded by the gene can be produced in large quantities by the genetic engineering technology. Thus, the gene and gene fragments provided by the present invention can be integrated with expression vectors to construct recombinant human p51 proteins and study p51 protein activity and the functions, e.g. binding activity, of the p51 protein.

Furthermore, the p51 protein is useful for the pathological elucidation, diagnosis and therapy of diseases associated with the p51 gene or its product (e.g. diseases related to the transcription activity of cells and various diseases related to apoptosis, particularly cancers).

The p51 protein has physiological actions or functions similar to those of the p53 protein. Therefore, when various biological stresses such as virus infection, cytokine stimulation, hypoxia, a change in the nucleotide pool, drug-induced metabolic derangements, etc. act upon the living tissues, the protein of the invention exhibits such functions as signal transductions through interactions with other proteins and transcriptional control over the other genes to thereby modulate replication of the cell DNA in the tissues subjected to said biological stresses, interrupt their cell cycle to repair the cells, eliminate cells through apoptosis, or promote the differentiation of cells to thereby control to the defense of living tissues against said stresses.

In accordance with the present invention, there are provided a gene transfer vector containing the human p51 gene or an allele thereof which is useful for gene therapy, cells into which said p51 gene or allele has been introduced, a genetherapeutic agent containing said vector or cells as an active ingredient, and a method of gene therapy exploiting them.

Furthermore, in accordance with the present invention, there is provided a pharmaceutical product containing the p51 protein as an active ingredient which has activity to suppress growth of various cancer cells and finds application in the treatment of various neoplastic diseases and associated symptoms through said activity.

The functional regions of the human p51 gene and the corresponding mouse gene are completely identical except for the 3 amino acids in the TA domain, thus reflecting a high degree of conservation and suggesting the importance of the present gene [The nucleotide sequences of the two genes are correlatedly shown in FIG. 12~14 and FIG. 15].

The invention claimed is:

1. An isolated antibody specifically binding to a protein comprising the amino acid sequence of SEQ ID NO:1, or a protein comprising an amino acid identified by amino acids 1-59, amino acids 142-321, and amino acids 359-397 of the amino acid sequence of SEQ ID NO:1.

2. An isolated antibody or a fragment thereof according to claim 1, wherein the antibody is a monoclonal antibody or a polyclonal antibody.

3. A method for assaying a p51 protein in a sample, wherein the p51 protein is detected by using the antibody of claim 1 or 2.

4. A method according to claim 3, wherein the method is an immuno assay.

5. A method according to claim 4, wherein the immuno assay is a sandwich technique, an enzyme-linked immunosorbent assay (ELISA), a radioimmunoassay (RIA), an immunoradiometric assay (IRMA), or an immunoenzymematrix-assay (IEMA).

* * * * *

SEQUENCE LISTING

```
<160> NUMBER OF SEQ ID NOS: 29

<210> SEQ ID NO 1
<211> LENGTH: 448
<212> TYPE: PRT
<213> ORGANISM: Homo sapiens
<220> FEATURE:
<221> NAME/KEY: DOMAIN
<222> LOCATION: (1)..(59)
<223> OTHER INFORMATION: transactivation domain
<220> FEATURE:
<221> NAME/KEY: DNA_BIND
<222> LOCATION: (142)..(321)
<223> OTHER INFORMATION: DNA binding domain
<220> FEATURE:
<221> NAME/KEY: DOMAIN
<222> LOCATION: (353)..(397)
<223> OTHER INFORMATION: oligomerization domain

<400> SEQUENCE: 1

Met Ser Gln Ser Thr Gln Thr Asn Glu Phe Leu Ser Pro Glu Val Phe
1               5                   10                  15

Gln His Ile Trp Asp Phe Leu Glu Gln Pro Ile Cys Ser Val Gln Pro
            20                  25                  30
```

-continued

```
Ile Asp Leu Asn Phe Val Asp Glu Pro Ser Glu Asp Gly Ala Thr Asn
        35                  40                  45
Lys Ile Glu Ile Ser Met Asp Cys Ile Arg Met Gln Asp Ser Asp Leu
 50                  55                  60
Ser Asp Pro Met Trp Pro Gln Tyr Thr Asn Leu Gly Leu Leu Asn Ser
 65                  70                  75                  80
Met Asp Gln Gln Ile Gln Asn Gly Ser Ser Thr Ser Pro Tyr Asn
                     85                  90                  95
Thr Asp His Ala Gln Asn Ser Val Thr Ala Pro Ser Pro Tyr Ala Gln
                100                 105                 110
Pro Ser Ser Thr Phe Asp Ala Leu Ser Pro Ser Pro Ala Ile Pro Ser
                115                 120                 125
Asn Thr Asp Tyr Pro Gly Pro His Ser Phe Asp Val Ser Phe Gln Gln
            130                 135                 140
Ser Ser Thr Ala Lys Ser Ala Thr Trp Thr Tyr Ser Thr Glu Leu Lys
145                 150                 155                 160
Lys Leu Tyr Cys Gln Ile Ala Lys Thr Cys Pro Ile Gln Ile Lys Val
                165                 170                 175
Met Thr Pro Pro Gln Gly Ala Val Ile Arg Ala Met Pro Val Tyr
                180                 185                 190
Lys Lys Ala Glu His Val Thr Glu Val Val Lys Arg Cys Pro Asn His
                195                 200                 205
Glu Leu Ser Arg Glu Phe Asn Glu Gly Gln Ile Ala Pro Pro Ser His
            210                 215                 220
Leu Ile Arg Val Glu Gly Asn Ser His Ala Gln Tyr Val Glu Asp Pro
225                 230                 235                 240
Ile Thr Gly Arg Gln Ser Val Leu Val Pro Tyr Glu Pro Pro Gln Val
                245                 250                 255
Gly Thr Glu Phe Thr Thr Val Leu Tyr Asn Phe Met Cys Asn Ser Ser
                260                 265                 270
Cys Val Gly Gly Met Asn Arg Arg Pro Ile Leu Ile Ile Val Thr Leu
            275                 280                 285
Glu Thr Arg Asp Gly Gln Val Leu Gly Arg Arg Cys Phe Glu Ala Arg
            290                 295                 300
Ile Cys Ala Cys Pro Gly Arg Asp Arg Lys Ala Asp Glu Asp Ser Ile
305                 310                 315                 320
Arg Lys Gln Gln Val Ser Asp Ser Thr Lys Asn Gly Asp Gly Thr Lys
                325                 330                 335
Arg Pro Phe Arg Gln Asn Thr His Gly Ile Gln Met Thr Ser Ile Lys
                340                 345                 350
Lys Arg Arg Ser Pro Asp Asp Glu Leu Leu Tyr Leu Pro Val Arg Gly
                355                 360                 365
Arg Glu Thr Tyr Glu Met Leu Leu Lys Ile Lys Glu Ser Leu Glu Leu
            370                 375                 380
Met Gln Tyr Leu Pro Gln His Thr Ile Glu Thr Tyr Arg Gln Gln Gln
385                 390                 395                 400
Gln Gln Gln His Gln His Leu Leu Gln Lys His Leu Leu Ser Ala Cys
                405                 410                 415
Phe Arg Asn Glu Leu Val Glu Pro Arg Arg Glu Thr Pro Lys Gln Ser
            420                 425                 430
Asp Val Phe Phe Arg His Ser Lys Pro Pro Asn Arg Ser Val Tyr Pro
            435                 440                 445
```

```
<210> SEQ ID NO 2
<211> LENGTH: 2816
<212> TYPE: DNA
<213> ORGANISM: Homo sapiens
<220> FEATURE:
<221> NAME/KEY: exon
<222> LOCATION: (145)..(1488)
<220> FEATURE:
<221> NAME/KEY: polyA_signal
<222> LOCATION: (2786)..(2791)

<400> SEQUENCE: 2
tcgttgatat caaagacagt tgaaggaaat gaattttgaa acttcacggt gtgccaccct      60
acagtactgc cctgacccct acatccagcg tttcgtagaa acccagctca tttctcttgg    120
aaagaaagtt attaccgatc cacc atg tcc cag agc aca cag aca aat gaa       171
                          Met Ser Gln Ser Thr Gln Thr Asn Glu
                           1               5 ttc ctc agt cca gag gtt ttc cag cat atc tgg gat ttt ctg gaa cag      219
Phe Leu Ser Pro Glu Val Phe Gln His Ile Trp Asp Phe Leu Glu Gln
 10              15                  20                  25 cct ata tgt tca gtt cag ccc att gac ttg aac ttt gtg gat gaa cca      267
Pro Ile Cys Ser Val Gln Pro Ile Asp Leu Asn Phe Val Asp Glu Pro
             30                  35                  40 tca gaa gat ggt gcg aca aac aag att gag att agc atg gac tgt atc      315
Ser Glu Asp Gly Ala Thr Asn Lys Ile Glu Ile Ser Met Asp Cys Ile
         45                  50                  55 cgc atg cag gac tcg gac ctg agt gac ccc atg tgg cca cag tac acg      363
Arg Met Gln Asp Ser Asp Leu Ser Asp Pro Met Trp Pro Gln Tyr Thr
     60                  65                  70 aac ctg ggg ctc ctg aac agc atg gac cag cag att cag aac ggc tcc      411
Asn Leu Gly Leu Leu Asn Ser Met Asp Gln Gln Ile Gln Asn Gly Ser
 75                  80                  85 tcg tcc acc agt ccc tat aac aca gac cac gcg cag aac agc gtc acg      459
Ser Ser Thr Ser Pro Tyr Asn Thr Asp His Ala Gln Asn Ser Val Thr
 90                  95                 100                 105 gcg ccc tcg ccc tac gca cag ccc agc tcc acc ttc gat gct ctc tct      507
Ala Pro Ser Pro Tyr Ala Gln Pro Ser Ser Thr Phe Asp Ala Leu Ser
            110                 115                 120 cca tca ccc gcc atc ccc tcc aac acc gac tac cca ggc ccg cac agt      555
Pro Ser Pro Ala Ile Pro Ser Asn Thr Asp Tyr Pro Gly Pro His Ser
        125                 130                 135 ttc gac gtg tcc ttc cag cag tcg agc acc gcc aag tcg gcc acc tgg      603
Phe Asp Val Ser Phe Gln Gln Ser Ser Thr Ala Lys Ser Ala Thr Trp
    140                 145                 150 acg tat tcc act gaa ctg aag aaa ctc tac tgc caa att gca aag aca      651
Thr Tyr Ser Thr Glu Leu Lys Lys Leu Tyr Cys Gln Ile Ala Lys Thr
155                 160                 165 tgc ccc atc cag atc aag gtg atg acc cca cct cct cag gga gct gtt      699
Cys Pro Ile Gln Ile Lys Val Met Thr Pro Pro Pro Gln Gly Ala Val
170                 175                 180                 185 atc cgc gcc atg cct gtc tac aaa aaa gct gag cac gtc acg gag gtg      747
Ile Arg Ala Met Pro Val Tyr Lys Lys Ala Glu His Val Thr Glu Val
                190                 195                 200 gtg aag cgg tgc ccc aac cat gag ctg agc cgt gaa ttc aac gag gga      795
Val Lys Arg Cys Pro Asn His Glu Leu Ser Arg Glu Phe Asn Glu Gly
            205                 210                 215 cag att gcc cct cct agt cat ttg att cga gta gag ggg aac agc cat      843
Gln Ile Ala Pro Pro Ser His Leu Ile Arg Val Glu Gly Asn Ser His
        220                 225                 230 gcc cag tat gta gaa gat ccc atc aca gga aga cag agt gtg ctg gta      891
Ala Gln Tyr Val Glu Asp Pro Ile Thr Gly Arg Gln Ser Val Leu Val
```

-continued

```
                235                 240                 245
cct tat gag cca ccc cag gtt ggc act gaa ttc acg aca gtc ttg tac     939
Pro Tyr Glu Pro Pro Gln Val Gly Thr Glu Phe Thr Thr Val Leu Tyr
250                 255                 260                 265 aat ttc atg tgt aac agc agt tgt gtt gga ggg atg aac cgc cgt cca     987
Asn Phe Met Cys Asn Ser Ser Cys Val Gly Gly Met Asn Arg Arg Pro
                270                 275                 280 att tta atc att gtt act ctg gaa acc aga gat ggg caa gtc ctg ggc    1035
Ile Leu Ile Ile Val Thr Leu Glu Thr Arg Asp Gly Gln Val Leu Gly
            285                 290                 295 cga cgc tgc ttt gag gcc cgg atc tgt gct tgc cca gga aga gac agg    1083
Arg Arg Cys Phe Glu Ala Arg Ile Cys Ala Cys Pro Gly Arg Asp Arg
        300                 305                 310 aag gcg gat gaa gat agc atc aga aag cag caa gtt tcg gac agt aca    1131
Lys Ala Asp Glu Asp Ser Ile Arg Lys Gln Gln Val Ser Asp Ser Thr
    315                 320                 325 aag aac ggt gat ggt acg aag cgc ccg ttt cgt cag aac aca cat ggt    1179
Lys Asn Gly Asp Gly Thr Lys Arg Pro Phe Arg Gln Asn Thr His Gly
330                 335                 340                 345 atc cag atg aca tcc atc aag aaa cga aga tcc cca gat gat gaa ctg    1227
Ile Gln Met Thr Ser Ile Lys Lys Arg Arg Ser Pro Asp Asp Glu Leu
                350                 355                 360 tta tac tta cca gtg agg ggc cgt gag act tat gaa atg ctg ttg aag    1275
Leu Tyr Leu Pro Val Arg Gly Arg Glu Thr Tyr Glu Met Leu Leu Lys
            365                 370                 375 atc aaa gag tcc ctg gaa ctc atg cag tac ctt cct cag cac aca att    1323
Ile Lys Glu Ser Leu Glu Leu Met Gln Tyr Leu Pro Gln His Thr Ile
        380                 385                 390 gaa acg tac agg caa cag caa cag cag cag cac cag cac tta ctt cag    1371
Glu Thr Tyr Arg Gln Gln Gln Gln Gln Gln His Gln His Leu Leu Gln
    395                 400                 405 aaa cat ctc ctt tca gcc tgc ttc agg aat gag ctt gtg gag ccc cgg    1419
Lys His Leu Leu Ser Ala Cys Phe Arg Asn Glu Leu Val Glu Pro Arg
410                 415                 420                 425 aga gaa act cca aaa caa tct gac gtc ttc ttt aga cat tcc aag ccc    1467
Arg Glu Thr Pro Lys Gln Ser Asp Val Phe Phe Arg His Ser Lys Pro
                430                 435                 440 cca aac cga tca gtg tac cca tagagcccta tctctatatt ttaagtgtgt       1518
Pro Asn Arg Ser Val Tyr Pro
                445 gtgttgtatt tccatgtgta tatgtgagtg tgtgtgtgtg tatgtgtgtg cgtgtgtatc  1578 tagccctcat aaacaggact tgaagacact ttggctcaga gacccaactg ctcaaaggca  1638 caaagccact agtgagagaa tcttttgaag ggactcaaac ctttacaaga aaggatgttt  1698 tctgcagatt ttgtatcctt agaccggcca ttggtgggtg aggaaccact gtgtttgtct  1758 gtgagctttc tgttgtttcc tgggagggag gggtcaggtg gggaaggggg cattaagatg  1818 tttattggaa ccctttttctg tcttcttctg ttgtttttct aaaattcaca gggaagcttt  1878 tgagcaggtc tcaaacttaa gatgtctttt taagaaaagg agaaaaaagt tgttattgtc  1938 tgtgcataag taagttgtag gtgactgaga gactcagtca gaccctttta atgctggtca  1998 tgtaataata ttgcaagtag taagaaacga aggtgtcaag tgtactgctg ggcagcgagg  2058 tgatcattac caaaagtaat caactttgtg ggtggagagt tctttgtgag aacttgcatt  2118 atttgtgtcc tcccctcatg tgtaggtaga acatttctta atgctgtgta cctgcctctg  2178 ccactgtatg ttggcatctg ttatgctaaa gttttttcttg tacatgaaac cctggaagac  2238 ctactacaaa aaaactgttg tttggccccc atagcaggtg aactcatttt gtgctttta a 2298
```

-continued

```
tagaaagaca aatccacccc agtaatattg cccttacgta gttgtttacc attattcaaa    2358
gctcaaaata gaatttgaag ccctctcaca aaatctgtga ttaatttgct taattagagc    2418
ttctatccct caagcctacc taccataaaa ccagccatat tactgatact gttcagtgca    2478
tttagccagg agacttacgt tttgagtaag tgagatccaa gcagacgtgt taaaatcagc    2538
actcctggac tggaaattaa agattgaaag ggtagactac ttttcttttt tttactcaaa    2598
agtttagaga atctctgttt ctttccattt taaaaacata ttttaagata atagcataaa    2658
gactttaaaa atgttcctcc cctccatctt cccacaccca gtcaccagca ctgtattttc    2718
tgtcaccaag acaatgattt cttgttattg aggctgttgc ttttgtggat gtgtgatttt    2778
aattttcaat aaactttgc atcttggttt aaaagaaa                            2816
```

<210> SEQ ID NO 3
<211> LENGTH: 393
<212> TYPE: PRT
<213> ORGANISM: Homo sapien

<400> SEQUENCE: 3

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
```

-continued

```
                275                 280                 285
Leu Arg Lys Lys Gly Glu Pro His His Glu Leu Pro Pro Gly Ser Thr
        290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                    340                 345                 350

Ala Gln Ala Gly Lys Glu Pro Gly Gly Ser Arg Ala His Ser Ser His
                355                 360                 365

Leu Lys Ser Lys Lys Gly Gln Ser Thr Ser Arg His Lys Lys Leu Met
            370                 375                 380

Phe Lys Thr Glu Gly Pro Asp Ser Asp
385                 390

<210> SEQ ID NO 4
<211> LENGTH: 641
<212> TYPE: PRT
<213> ORGANISM: Homo sapiens
<220> FEATURE:
<221> NAME/KEY: DOMAIN
<222> LOCATION: (1)..(59)
<223> OTHER INFORMATION: transactivation domain
<220> FEATURE:
<221> NAME/KEY: DNA_BIND
<222> LOCATION: (142)..(321)
<223> OTHER INFORMATION: DNA binding domain
<220> FEATURE:
<221> NAME/KEY: DOMAIN
<222> LOCATION: (353)..(397)
<223> OTHER INFORMATION: oligomerization domain

<400> SEQUENCE: 4

Met Ser Gln Ser Thr Gln Thr Asn Glu Phe Leu Ser Pro Glu Val Phe
1               5                   10                  15

Gln His Ile Trp Asp Phe Leu Glu Gln Pro Ile Cys Ser Val Gln Pro
                20                  25                  30

Ile Asp Leu Asn Phe Val Asp Glu Pro Ser Glu Asp Gly Ala Thr Asn
            35                  40                  45

Lys Ile Glu Ile Ser Met Asp Cys Ile Arg Met Gln Asp Ser Asp Leu
        50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95

Thr Asp His Ala Gln Asn Ser Val Thr Ala Pro Ser Pro Tyr Ala Gln
                100                 105                 110

Pro Ser Ser Thr Phe Asp Ala Leu Ser Pro Ser Pro Ala Ile Pro Ser
            115                 120                 125

Asn Thr Asp Tyr Pro Gly Pro His Ser Phe Asp Val Ser Phe Gln Gln
        130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
                180                 185                 190
```

```
Lys Lys Ala Glu His Val Thr Glu Val Val Lys Arg Cys Pro Asn His
        195                 200                 205

Glu Leu Ser Arg Glu Phe Asn Glu Gly Gln Ile Ala Pro Pro Ser His
        210                 215                 220

Leu Ile Arg Val Glu Gly Asn Ser His Ala Gln Tyr Val Glu Asp Pro
225                 230                 235                 240

Ile Thr Gly Arg Gln Ser Val Leu Val Pro Tyr Glu Pro Pro Gln Val
            245                 250                 255

Gly Thr Glu Phe Thr Thr Val Leu Tyr Asn Phe Met Cys Asn Ser Ser
                260                 265                 270

Cys Val Gly Gly Met Asn Arg Pro Ile Leu Ile Ile Val Thr Leu
            275                 280                 285

Glu Thr Arg Asp Gly Gln Val Leu Gly Arg Arg Cys Phe Glu Ala Arg
        290                 295                 300

Ile Cys Ala Cys Pro Gly Arg Asp Arg Lys Ala Asp Glu Asp Ser Ile
305                 310                 315                 320

Arg Lys Gln Gln Val Ser Asp Ser Thr Lys Asn Gly Asp Gly Thr Lys
                325                 330                 335

Arg Pro Phe Arg Gln Asn Thr His Gly Ile Gln Met Thr Ser Ile Lys
            340                 345                 350

Lys Arg Arg Ser Pro Asp Asp Glu Leu Leu Tyr Leu Pro Val Arg Gly
        355                 360                 365

Arg Glu Thr Tyr Glu Met Leu Leu Lys Ile Lys Glu Ser Leu Glu Leu
        370                 375                 380

Met Gln Tyr Leu Pro Gln His Thr Ile Glu Thr Tyr Arg Gln Gln Gln
385                 390                 395                 400

Gln Gln Gln His Gln His Leu Leu Gln Lys Gln Thr Ser Ile Gln Ser
                405                 410                 415

Pro Ser Ser Tyr Gly Asn Ser Ser Pro Pro Leu Asn Lys Met Asn Ser
            420                 425                 430

Met Asn Lys Leu Pro Ser Val Ser Gln Leu Ile Asn Pro Gln Gln Arg
        435                 440                 445

Asn Ala Leu Thr Pro Thr Thr Ile Pro Asp Gly Met Gly Ala Asn Ile
        450                 455                 460

Pro Met Met Gly Thr His Met Pro Met Ala Gly Asp Met Asn Gly Leu
465                 470                 475                 480

Ser Pro Thr Gln Ala Leu Pro Pro Leu Ser Met Pro Ser Thr Ser
                485                 490                 495

His Cys Thr Pro Pro Pro Tyr Pro Thr Asp Cys Ser Ile Val Ser
            500                 505                 510

Phe Leu Ala Arg Leu Gly Cys Ser Ser Cys Leu Asp Tyr Phe Thr Thr
        515                 520                 525

Gln Gly Leu Thr Thr Ile Tyr Gln Ile Glu His Tyr Ser Met Asp Asp
        530                 535                 540

Leu Ala Ser Leu Lys Ile Pro Glu Gln Phe Arg His Ala Ile Trp Lys
545                 550                 555                 560

Gly Ile Leu Asp His Arg Gln Leu His Glu Phe Ser Ser Pro Ser His
                565                 570                 575

Leu Leu Arg Thr Pro Ser Ser Ala Ser Thr Val Ser Val Gly Ser Ser
            580                 585                 590

Glu Thr Arg Gly Glu Arg Val Ile Asp Ala Val Arg Phe Thr Leu Arg
        595                 600                 605

Gln Thr Ile Ser Phe Pro Pro Arg Asp Glu Trp Asn Asp Phe Asn Phe
```

```
                610              615              620
Asp Met Asp Ala Arg Arg Asn Lys Gln Gln Arg Ile Lys Glu Glu Gly
625              630              635              640

Glu

<210> SEQ ID NO 5
<211> LENGTH: 2270
<212> TYPE: DNA
<213> ORGANISM: Homo sapiens
<220> FEATURE:
<221> NAME/KEY: exon
<222> LOCATION: (145)..(2067)

<400> SEQUENCE: 5
tcgttgatat caaagacagt tgaaggaaat gaattttgaa acttcacggt gtgccaccct      60
acagtactgc cctgacccct acatccagcg tttcgtagaa acccagctca tttctcttgg     120
aaagaaagtt attaccgatc cacc atg tcc cag agc aca cag aca aat gaa       171
                          Met Ser Gln Ser Thr Gln Thr Asn Glu
                           1               5 ttc ctc agt cca gag gtt ttc cag cat atc tgg gat ttt ctg gaa cag      219
Phe Leu Ser Pro Glu Val Phe Gln His Ile Trp Asp Phe Leu Glu Gln
 10              15                  20                  25 cct ata tgt tca gtt cag ccc att gac ttg aac ttt gtg gat gaa cca      267
Pro Ile Cys Ser Val Gln Pro Ile Asp Leu Asn Phe Val Asp Glu Pro
             30                  35                  40 tca gaa gat ggt gcg aca aac aag att gag att agc atg gac tgt atc      315
Ser Glu Asp Gly Ala Thr Asn Lys Ile Glu Ile Ser Met Asp Cys Ile
                 45                  50                  55 cgc atg cag gac tcg gac ctg agt gac ccc atg tgg cca cag tac acg      363
Arg Met Gln Asp Ser Asp Leu Ser Asp Pro Met Trp Pro Gln Tyr Thr
             60                  65                  70 aac ctg ggg ctc ctg aac agc atg gac cag cag att cag aac ggc tcc      411
Asn Leu Gly Leu Leu Asn Ser Met Asp Gln Gln Ile Gln Asn Gly Ser
 75                  80                  85 tcg tcc acc agt ccc tat aac aca gac cac gcg cag aac agc gtc acg      459
Ser Ser Thr Ser Pro Tyr Asn Thr Asp His Ala Gln Asn Ser Val Thr
 90                  95                 100                 105 gcg ccc tcg ccc tac gca cag ccc agc tcc acc ttc gat gct ctc tct      507
Ala Pro Ser Pro Tyr Ala Gln Pro Ser Ser Thr Phe Asp Ala Leu Ser
                110                 115                 120 cca tca ccc gcc atc ccc tcc aac acc gac tac cca ggc ccg cac agt      555
Pro Ser Pro Ala Ile Pro Ser Asn Thr Asp Tyr Pro Gly Pro His Ser
            125                 130                 135 ttc gac gtg tcc ttc cag cag tcg agc acc gcc aag tcg gcc acc tgg      603
Phe Asp Val Ser Phe Gln Gln Ser Ser Thr Ala Lys Ser Ala Thr Trp
        140                 145                 150 acg tat tcc act gaa ctg aag aaa ctc tac tgc caa att gca aag aca      651
Thr Tyr Ser Thr Glu Leu Lys Lys Leu Tyr Cys Gln Ile Ala Lys Thr
    155                 160                 165 tgc ccc atc cag atc aag gtg atg acc cca cct cct cag gga gct gtt      699
Cys Pro Ile Gln Ile Lys Val Met Thr Pro Pro Pro Gln Gly Ala Val
170                 175                 180                 185 atc cgc gcc atg cct gtc tac aaa aaa gct gag cac gtc acg gag gtg      747
Ile Arg Ala Met Pro Val Tyr Lys Lys Ala Glu His Val Thr Glu Val
                190                 195                 200 gtg aag cgg tgc ccc aac cat gag ctg agc cgt gaa ttc aac gag gga      795
Val Lys Arg Cys Pro Asn His Glu Leu Ser Arg Glu Phe Asn Glu Gly
            205                 210                 215 cag att gcc cct cct agt cat ttg att cga gta gag ggg aac agc cat      843
Gln Ile Ala Pro Pro Ser His Leu Ile Arg Val Glu Gly Asn Ser His
```

```
                Gln Ile Ala Pro Pro Ser His Leu Ile Arg Val Glu Gly Asn Ser His
                    220                 225                 230 gcc cag tat gta gaa gat ccc atc aca gga aga cag agt gtg ctg gta        891
Ala Gln Tyr Val Glu Asp Pro Ile Thr Gly Arg Gln Ser Val Leu Val
235                 240                 245 cct tat gag cca ccc cag gtt ggc act gaa ttc acg aca gtc ttg tac        939
Pro Tyr Glu Pro Pro Gln Val Gly Thr Glu Phe Thr Thr Val Leu Tyr
250                 255                 260                 265 aat ttc atg tgt aac agc agt tgt gtt gga ggg atg aac cgc cgt cca        987
Asn Phe Met Cys Asn Ser Ser Cys Val Gly Gly Met Asn Arg Arg Pro
                270                 275                 280 att tta atc att gtt act ctg gaa acc aga gat ggg caa gtc ctg ggc       1035
Ile Leu Ile Ile Val Thr Leu Glu Thr Arg Asp Gly Gln Val Leu Gly
285                 290                 295 cga cgc tgc ttt gag gcc cgg atc tgt gct tgc cca gga aga gac agg       1083
Arg Arg Cys Phe Glu Ala Arg Ile Cys Ala Cys Pro Gly Arg Asp Arg
        300                 305                 310 aag gcg gat gaa gat agc atc aga aag cag caa gtt tcg gac agt aca       1131
Lys Ala Asp Glu Asp Ser Ile Arg Lys Gln Gln Val Ser Asp Ser Thr
315                 320                 325 aag aac ggt gat ggt acg aag cgc ccg ttt cgt cag aac aca cat ggt       1179
Lys Asn Gly Asp Gly Thr Lys Arg Pro Phe Arg Gln Asn Thr His Gly
330                 335                 340                 345 atc cag atg aca tcc atc aag aaa cga aga tcc cca gat gat gaa ctg       1227
Ile Gln Met Thr Ser Ile Lys Lys Arg Arg Ser Pro Asp Asp Glu Leu
                350                 355                 360 tta tac tta cca gtg agg ggc cgt gag act tat gaa atg ctg ttg aag       1275
Leu Tyr Leu Pro Val Arg Gly Arg Glu Thr Tyr Glu Met Leu Leu Lys
            365                 370                 375 atc aaa gag tcc ctg gaa ctc atg cag tac ctt cct cag cac aca att       1323
Ile Lys Glu Ser Leu Glu Leu Met Gln Tyr Leu Pro Gln His Thr Ile
380                 385                 390 gaa acg tac agg caa cag caa cag cag cag cac cag cac tta ctt cag       1371
Glu Thr Tyr Arg Gln Gln Gln Gln Gln His Gln His Leu Leu Gln
395                 400                 405 aaa cag acc tca ata cag tct cca tct tca tat ggt aac agc tcc cca       1419
Lys Gln Thr Ser Ile Gln Ser Pro Ser Ser Tyr Gly Asn Ser Ser Pro
410                 415                 420                 425 cct ctg aac aaa atg aac agc atg aac aag ctg cct tct gtg agc cag       1467
Pro Leu Asn Lys Met Asn Ser Met Asn Lys Leu Pro Ser Val Ser Gln
                430                 435                 440 ctt atc aac cct cag cag cgc aac gcc ctc act cct aca acc att cct       1515
Leu Ile Asn Pro Gln Gln Arg Asn Ala Leu Thr Pro Thr Thr Ile Pro
            445                 450                 455 gat ggc atg gga gcc aac att ccc atg atg ggc acc cac atg cca atg       1563
Asp Gly Met Gly Ala Asn Ile Pro Met Met Gly Thr His Met Pro Met
460                 465                 470 gct gga gac atg aat gga ctc agc ccc acc cag gca ctc cct ccc cca       1611
Ala Gly Asp Met Asn Gly Leu Ser Pro Thr Gln Ala Leu Pro Pro Pro
475                 480                 485 ctc tcc atg cca tcc acc tcc cac tgc aca ccc cca cct ccg tat ccc       1659
Leu Ser Met Pro Ser Thr Ser His Cys Thr Pro Pro Pro Pro Tyr Pro
490                 495                 500                 505 aca gat tgc agc att gtc agt ttc tta gcg agg ttg ggc tgt tca tca       1707
Thr Asp Cys Ser Ile Val Ser Phe Leu Ala Arg Leu Gly Cys Ser Ser
                510                 515                 520 tgt ctg gac tat ttc acg acc cag ggg ctg acc acc atc tat cag att       1755
Cys Leu Asp Tyr Phe Thr Thr Gln Gly Leu Thr Thr Ile Tyr Gln Ile
            525                 530                 535
```

-continued

```
gag cat tac tcc atg gat gat ctg gca agt ctg aaa atc cct gag caa       1803
Glu His Tyr Ser Met Asp Asp Leu Ala Ser Leu Lys Ile Pro Glu Gln
        540                 545                 550 ttt cga cat gcg atc tgg aag ggc atc ctg gac cac cgg cag ctc cac       1851
Phe Arg His Ala Ile Trp Lys Gly Ile Leu Asp His Arg Gln Leu His
    555                 560                 565 gaa ttc tcc tcc cct tct cat ctc ctg cgg acc cca agc agt gcc tct       1899
Glu Phe Ser Ser Pro Ser His Leu Leu Arg Thr Pro Ser Ser Ala Ser
570                 575                 580                 585 aca gtc agt gtg ggc tcc agt gag acc cgg ggt gag cgt gtt att gat       1947
Thr Val Ser Val Gly Ser Ser Glu Thr Arg Gly Glu Arg Val Ile Asp
                590                 595                 600 gct gtg cga ttc acc ctc cgc cag acc atc tct ttc cca ccc cga gat       1995
Ala Val Arg Phe Thr Leu Arg Gln Thr Ile Ser Phe Pro Pro Arg Asp
            605                 610                 615 gag tgg aat gac ttc aac ttt gac atg gat gct cgc cgc aat aag caa       2043
Glu Trp Asn Asp Phe Asn Phe Asp Met Asp Ala Arg Arg Asn Lys Gln
        620                 625                 630 cag cgc atc aaa gag gag ggg gag tgagcctcac catgtgagct cttcctatcc     2097
Gln Arg Ile Lys Glu Glu Gly Glu
    635                 640 ctctcctaac tgccagcccc ctaaaagcac tcctgcttaa tcttcaaagc cttctcccta    2157
gctcctcccc ttcctcttgt ctgatttctt aggggaagga gaagtaagag gctacctctt    2217
acctaacatc tgacctggca tctaattctg attctggctt taagccttca aaa           2270

<210> SEQ ID NO 6
<211> LENGTH: 499
<212> TYPE: PRT
<213> ORGANISM: Homo sapien

<400> SEQUENCE: 6

Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Val Lys
            180                 185                 190

Arg Cys Pro Asn His Glu Leu Gly Arg Asp Phe Asn Glu Gly Gln Ser
```

-continued

```
                   195                 200                 205
Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
            260                 265                 270

Ile Ile Ile Thr Leu Glu Met Arg Asp Gly Gln Val Leu Gly Arg Arg
        275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Ala Gly Val Lys Lys Arg Arg His Gly Asp Glu
            340                 345                 350

Asp Thr Tyr Tyr Leu Gln Val Arg Gly Arg Glu Asn Phe Glu Ile Leu
        355                 360                 365

Met Lys Leu Lys Glu Ser Leu Glu Leu Met Glu Leu Val Pro Gln Pro
    370                 375                 380

Leu Val Asp Ser Tyr Arg Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Met Asn Lys Leu Pro Ser Val Asn Gln Leu Val Gly
            420                 425                 430

Gln Pro Pro Pro His Ser Ser Ala Ala Thr Pro Asn Leu Gly Pro Val
        435                 440                 445

Gly Pro Gly Met Leu Asn Asn His Gly His Ala Val Pro Ala Asn Gly
    450                 455                 460

Glu Met Ser Ser His Ser Ala Gln Ser Met Val Ser Gly Ser His
465                 470                 475                 480

Cys Thr Pro Pro Pro Tyr His Ala Asp Pro Ser Leu Val Arg Thr
                485                 490                 495

Trp Gly Pro

<210> SEQ ID NO 7
<211> LENGTH: 312
<212> TYPE: PRT
<213> ORGANISM: Artificial Sequence
<220> FEATURE:
<223> OTHER INFORMATION: Consensus of p51a, p53 and p73 beta

<400> SEQUENCE: 7

Met Gln Ser Thr Thr Pro Phe Gln His Trp Ser Leu Glu Pro Asp Leu
1               5                   10                  15

Pro Asn Asn Ser Met Asp Leu Asp Gln Leu Leu Ser Gln Arg Ser Ala
                20                  25                  30

Ser Pro Tyr His Ala Ser Val Pro Thr Pro Ser Pro Tyr Ala Gln Pro
            35                  40                  45

Ser Ser Thr Phe Asp Leu Ser Pro Ser Pro Ile Pro Ser Asn Thr Asp
        50                  55                  60
```

```
Tyr Pro Gly Pro His Phe Val Phe Gln Gln Ser Ser Thr Ala Lys Ser
 65                  70                  75                  80

Ala Thr Trp Thr Tyr Ser Pro Leu Lys Lys Leu Tyr Cys Gln Ile Ala
                 85                  90                  95

Lys Thr Cys Pro Ile Gln Ile Lys Val Thr Pro Pro Pro Gly Thr
            100                 105                 110

Ile Arg Ala Met Pro Val Tyr Lys Lys Ala Glu His Val Thr Glu Val
            115                 120                 125

Val Lys Arg Cys Pro Asn His Glu Leu Arg Asp Phe Asn Glu Gly Gln
130                 135                 140

Ala Pro Pro Ser His Leu Ile Arg Val Glu Gly Asn Gln Tyr Val Asp
145                 150                 155                 160

Asp Pro Thr Gly Arg Gln Ser Val Val Pro Tyr Glu Pro Pro Gln
                165                 170                 175

Val Gly Thr Glu Phe Thr Thr Ile Leu Tyr Asn Phe Met Cys Asn Ser
            180                 185                 190

Ser Cys Val Gly Gly Met Asn Arg Arg Pro Ile Leu Ile Ile Ile Thr
        195                 200                 205

Leu Glu Arg Asp Gly Gln Val Leu Gly Arg Arg Ser Phe Glu Arg Ile
210                 215                 220

Cys Ala Cys Pro Gly Arg Asp Arg Lys Ala Asp Glu Asp Arg Lys Gln
225                 230                 235                 240

Gln Ser Lys Asn Gly Thr Lys Arg Ala Phe Gln Asn Thr Lys Lys Arg
                245                 250                 255

Arg Asp Glu Tyr Leu Gln Val Arg Gly Arg Glu Phe Glu Met Leu Lys
            260                 265                 270

Leu Lys Glu Ser Leu Glu Leu Met Pro Gln Tyr Arg Gln Gln Gln Gln
        275                 280                 285

His Leu Lys His Asn Gln Leu Val Pro Arg His Thr Pro Lys Leu Val
    290                 295                 300

Met Phe His Pro Pro Asn Ser Tyr
305                 310

<210> SEQ ID NO 8
<211> LENGTH: 636
<212> TYPE: PRT
<213> ORGANISM: Homo sapien

<400> SEQUENCE: 8

Met Ala Gln Ser Thr Ala Thr Ser Pro Asp Gly Gly Thr Thr Phe Glu
 1               5                  10                  15

His Leu Trp Ser Ser Leu Glu Pro Asp Ser Thr Tyr Phe Asp Leu Pro
                20                  25                  30

Gln Ser Ser Arg Gly Asn Asn Glu Val Val Gly Gly Thr Asp Ser Ser
            35                  40                  45

Met Asp Val Phe His Leu Glu Gly Met Thr Thr Ser Val Met Ala Gln
 50                  55                  60

Phe Asn Leu Leu Ser Ser Thr Met Asp Gln Met Ser Ser Arg Ala Ala
 65                  70                  75                  80

Ser Ala Ser Pro Tyr Thr Pro Glu His Ala Ala Ser Val Pro Thr His
                 85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
```

```
                    115                 120                 125
Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Thr Pro Pro Gly Thr Ala Ile Arg
                    165                 170                 175

Ala Met Pro Val Tyr Lys Lys Ala Glu His Val Thr Asp Val Val Lys
                180                 185                 190

Arg Cys Pro Asn His Glu Leu Gly Arg Asp Phe Asn Glu Gly Gln Ser
            195                 200                 205

Ala Pro Ala Ser His Leu Ile Arg Val Glu Gly Asn Leu Ser Gln
    210                 215                 220

Tyr Val Asp Asp Pro Val Thr Gly Arg Gln Ser Val Val Pro Tyr
225                 230                 235                 240

Glu Pro Pro Gln Val Gly Thr Glu Phe Thr Thr Ile Leu Tyr Asn Phe
                    245                 250                 255

Met Cys Asn Ser Ser Cys Val Gly Gly Met Asn Arg Arg Pro Ile Leu
            260                 265                 270

Ile Ile Ile Thr Leu Glu Met Arg Asp Gly Gln Val Leu Gly Arg Arg
        275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                    325                 330                 335

Val Pro Ala Leu Gly Ala Gly Val Lys Lys Arg Arg His Gly Asp Glu
                340                 345                 350

Asp Thr Tyr Tyr Leu Gln Val Arg Gly Arg Glu Asn Phe Glu Ile Leu
            355                 360                 365

Met Lys Leu Lys Glu Ser Leu Glu Leu Met Glu Leu Val Pro Gln Pro
        370                 375                 380

Leu Val Asp Ser Tyr Arg Gln Gln Gln Leu Leu Gln Arg Pro Ser
385                 390                 395                 400

His Leu Gln Pro Pro Ser Tyr Gly Pro Val Leu Ser Pro Met Asn Lys
                    405                 410                 415

Val His Gly Gly Met Asn Lys Leu Pro Ser Val Asn Gln Leu Val Gly
                420                 425                 430

Gln Pro Pro Pro His Ser Ser Ala Ala Thr Pro Asn Leu Gly Pro Val
            435                 440                 445

Gly Pro Gly Met Leu Asn Asn His Gly His Ala Val Pro Ala Asn Gly
        450                 455                 460

Glu Met Ser Ser Ser His Ser Ala Gln Ser Met Val Ser Gly Ser His
465                 470                 475                 480

Cys Thr Pro Pro Pro Tyr His Ala Asp Pro Ser Leu Val Ser Phe
                    485                 490                 495

Leu Thr Gly Leu Gly Cys Pro Asn Cys Ile Glu Tyr Phe Thr Ser Gln
                500                 505                 510

Gly Leu Gln Ser Ile Tyr His Leu Gln Asn Leu Thr Ile Glu Asp Leu
            515                 520                 525

Gly Ala Leu Lys Ile Pro Glu Gln Tyr Arg Met Thr Ile Trp Arg Gly
        530                 535                 540
```

-continued

```
Leu Gln Asp Leu Lys Gln Gly His Asp Tyr Ser Thr Ala Gln Gln Leu
545                 550                 555                 560

Leu Arg Ser Ser Asn Ala Ala Thr Ile Ser Ile Gly Gly Ser Gly Glu
                565                 570                 575

Leu Gln Arg Gln Arg Val Met Glu Ala Val His Phe Arg Val Arg His
            580                 585                 590

Thr Ile Thr Ile Pro Asn Arg Gly Gly Pro Gly Gly Gly Pro Asp Glu
        595                 600                 605

Trp Ala Asp Phe Gly Phe Asp Leu Pro Asp Cys Lys Ala Arg Lys Gln
    610                 615                 620

Pro Ile Lys Glu Glu Phe Thr Glu Ala Glu Ile His
625                 630                 635

<210> SEQ ID NO 9
<211> LENGTH: 349
<212> TYPE: PRT
<213> ORGANISM: Artificial Sequence
<220> FEATURE:
<223> OTHER INFORMATION: Consensus of p51B and p73-alpha

<400> SEQUENCE: 9

Met Gln Ser Thr Thr Phe His Trp Leu Glu Pro Asp Leu Ser Met Asp
1               5                   10                  15

Gln Leu Leu Ser Gln Ser Ser Pro Tyr His Ala Ser Val Ser Pro Tyr
            20                  25                  30

Ala Gln Pro Ser Ser Thr Phe Asp Ser Pro Ile Pro Ser Asn Thr
        35                  40                  45

Asp Tyr Pro Gly Pro His Phe Val Phe Gln Gln Ser Ser Thr Ala Lys
    50                  55                  60

Ser Ala Thr Trp Thr Tyr Ser Leu Lys Lys Leu Tyr Cys Gln Ile Ala
65                  70                  75                  80

Lys Thr Cys Pro Ile Gln Ile Lys Val Thr Pro Pro Gly Ile Arg
                85                  90                  95

Ala Met Pro Val Tyr Lys Lys Ala Glu His Val Thr Val Lys Arg
            100                 105                 110

Cys Pro Asn His Glu Leu Arg Phe Asn Glu Gly Gln Ala Pro Ser His
            115                 120                 125

Leu Ile Arg Val Glu Gly Asn Gln Tyr Val Asp Pro Thr Gly Arg Gln
    130                 135                 140

Ser Val Val Pro Tyr Glu Pro Pro Gln Val Gly Thr Glu Phe Thr Thr
145                 150                 155                 160

Leu Tyr Asn Phe Met Cys Asn Ser Ser Cys Val Gly Gly Met Asn Arg
                165                 170                 175

Arg Pro Ile Leu Ile Ile Thr Leu Glu Arg Asp Gly Gln Val Leu Gly
            180                 185                 190

Arg Arg Phe Glu Arg Ile Cys Ala Cys Pro Gly Arg Asp Arg Lys Ala
        195                 200                 205

Asp Glu Asp Arg Gln Gln Ser Lys Asn Gly Lys Arg Phe Gln Lys Lys
    210                 215                 220

Arg Arg Asp Tyr Leu Val Arg Gly Arg Glu Glu Leu Lys Lys Glu Ser
225                 230                 235                 240

Leu Glu Leu Met Pro Gln Tyr Arg Gln Gln Gln Gln Pro Ser Tyr
                245                 250                 255

Gly Pro Asn Lys Met Asn Lys Leu Pro Ser Val Gln Leu Thr Gly Met
            260                 265                 270
```

His Ser Ser Met Ser Ser His Cys Thr Pro Pro Pro Tyr Asp Ser
            275                 280                 285

Val Phe Leu Leu Gly Cys Cys Tyr Phe Thr Gln Gly Leu Ile Tyr Asp
        290                 295                 300

Leu Leu Lys Ile Pro Glu Gln Arg Ile Trp Gly Asp Gln His Ser Leu
305                 310                 315                 320

Leu Arg Ala Gly Ser Glu Arg Val Ala Val Phe Arg Thr Ile Pro Arg
                325                 330                 335

Asp Glu Trp Asp Phe Phe Asp Gln Ile Lys Glu Glu Glu
            340                 345

<210> SEQ ID NO 10
<211> LENGTH: 1923
<212> TYPE: DNA
<213> ORGANISM: Mus musculus

<400> SEQUENCE: 10

```
atgtcgcaga gcacccagac aagcgagttc ctcagcccag aggtcttcca gcatatctgg      60
gattttctgg aacagcctat atgctcagta cagcccatcg agttgaactt tgtggatgaa     120
ccttccgaaa atggtgcaac aaacaagatt gagattagca tggattgtat ccgcatgcaa     180
gactcagacc tcagtgaccc catgtggcca gtacacgaa cctgggct cctgaacagc       240
atggaccagc agattcagaa cggctcctcg tccaccagcc cctacaacac agaccacgca     300
cagaatagcg tgacggcgcc ctcgccctat gcacagccca gctccacctt tgatgccctc     360
tctccatccc ctgccattcc ctccaacaca gattacccgg cccacacag cttcgatgtg      420
tccttccagc agtcaagcac tgccaagtca gccacctgga cgtattccac cgaactgaag     480
aagctgtact gccagattgc gaagacatgc cccatccaga tcaaggtgat gaccccaccc     540
ccacagggcg ctgttatccg tgccatgcct gtctacaaga agctgagca tgtcaccgag      600
gttgtgaaac gatgccctaa ccatgagctg agccgtgagt tcaatgaggg acagattgcc     660
cctcccagtc atctgattcg agtagaaggg aacagccatg cccagtatgt agaagatcct     720
atcacgggaa ggcagagcgt gctggtccct tatgagccac acaggttgg cactgaattc      780
acaacagtcc tgtacaattt catgtgtaac agcagctgcg tcggaggaat gaacagacgt     840
ccaattttaa tcatcgttac tctggaaacc agagatgggc aagtcctggg ccgacggtgc     900
tttgaggccc ggatctgtgc ttgcccagga agagaccgga aggcagatga agacagcatc     960
agaaagcagc aagtatcgga cagcgcaaag aacggcgatg gtacgaagcg ccctttccgt    1020
cagaatacac acggaatcca gatgacttcc atcaagaaac ggagatcccc agatgatgag    1080
ctgctgtacc taccagtgag aggtcgtgag acgtacgaga tgttgctgaa gatcaaagag    1140
tcactggagc tcatgcagta cctcccctcag cacacgatcg aaacgtacag gcagcagcag    1200
cagcagcagc accagcacct acttcagaaa cagacctcga tgcagtctca gtcttcatat    1260
ggcaacagtt ccccacctct gaacaaaatg aacagcatga caagctgcc ttccgtgagc    1320
cagcttatca acccacagca gcgcaatgcc ctcactccca ccaccatgcc tgagggcatg    1380
ggagccaaca ttcctatgat gggcactcac atgccaatgg ctggagacat gaatggactc    1440
agccctaccc aagctctccc tcctccactc tccatgccct ccacctccca ctgcacccca    1500
ccaccgccct accccacaga ctgcagcatt gtcagtttct tagcaaggtt gggctgctca    1560
tcatgcctgg actatttcac gacccagggg ctgaccacca tctatcagat tgagcattac    1620
tccatggatg attttggcaag tctgaagatc cctgaacagt tccgacatgc catctggaag    1680
```

-continued

```
ggcatcctgg accacaggca gctgcacgac ttctcctcac ctcctcatct cctgaggacc    1740
ccaagtggtg cctctaccgt cagtgtgggc tccagtgaga cccgtggtga acgtgtgatc    1800
gatgccgtgc gctttaccct ccgccagacc atctcttttc caccccgtga cgagtggaat    1860
gatttcaact ttgacatgga ttctcgtcgc aacaagcagc agcgtatcaa agaggaagga    1920
gaa                                                                  1923
```

<210> SEQ ID NO 11
<211> LENGTH: 641
<212> TYPE: PRT
<213> ORGANISM: Mus musculus

<400> SEQUENCE: 11

```
Met Ser Gln Ser Thr Gln Thr Ser Glu Phe Leu Ser Pro Glu Val Phe
1               5                   10                  15

Gln His Ile Trp Asp Phe Leu Glu Gln Pro Ile Cys Ser Val Gln Pro
            20                  25                  30

Ile Glu Leu Asn Phe Val Asp Glu Pro Ser Glu Asn Gly Ala Thr Asn
        35                  40                  45

Lys Ile Glu Ile Ser Met Asp Cys Ile Arg Met Gln Asp Ser Asp Leu
    50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Thr Ser Pro Tyr Asn
                85                  90                  95

Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
        115                 120                 125

Asn Thr Asp Tyr Pro Gly Pro His Ser Phe Asp Val Ser Phe Gln Gln
    130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
            180                 185                 190

Lys Lys Ala Glu His Val Thr Glu Val Val Lys Arg Cys Pro Asn His
        195                 200                 205

Glu Leu Ser Arg Glu Phe Asn Glu Gly Gln Ile Ala Pro Pro Ser His
    210                 215                 220

Leu Ile Arg Val Glu Gly Asn Ser His Ala Gln Tyr Val Glu Asp Pro
225                 230                 235                 240

Ile Thr Gly Arg Gln Ser Val Leu Val Pro Tyr Glu Pro Pro Gln Val
                245                 250                 255

Gly Thr Glu Phe Thr Thr Val Leu Tyr Asn Phe Met Cys Asn Ser Ser
            260                 265                 270

Cys Val Gly Gly Met Asn Arg Arg Pro Ile Leu Ile Ile Val Thr Leu
        275                 280                 285

Glu Thr Arg Asp Gly Gln Val Leu Gly Arg Arg Cys Phe Glu Ala Arg
    290                 295                 300

Ile Cys Ala Cys Pro Gly Arg Asp Arg Lys Ala Asp Glu Asp Ser Ile
305                 310                 315                 320
```

```
Arg Lys Gln Gln Val Ser Asp Ser Ala Lys Asn Gly Asp Gly Thr Lys
                325                 330                 335
Arg Pro Phe Arg Gln Asn Thr His Gly Ile Gln Met Thr Ser Ile Lys
            340                 345                 350
Lys Arg Arg Ser Pro Asp Asp Glu Leu Leu Tyr Leu Pro Val Arg Gly
        355                 360                 365
Arg Glu Thr Tyr Glu Met Leu Leu Lys Ile Lys Glu Ser Leu Glu Leu
    370                 375                 380
Met Gln Tyr Leu Pro Gln His Thr Ile Glu Thr Tyr Arg Gln Gln Gln
385                 390                 395                 400
Gln Gln Gln His Gln His Leu Leu Gln Lys Gln Thr Ser Met Gln Ser
                405                 410                 415
Gln Ser Ser Tyr Gly Asn Ser Ser Pro Pro Leu Asn Lys Met Asn Ser
            420                 425                 430
Met Asn Lys Leu Pro Ser Val Ser Gln Leu Ile Asn Pro Gln Gln Arg
        435                 440                 445
Asn Ala Leu Thr Pro Thr Thr Met Pro Glu Gly Met Gly Ala Asn Ile
    450                 455                 460
Pro Met Met Gly Thr His Met Pro Met Ala Gly Asp Met Asn Gly Leu
465                 470                 475                 480
Ser Pro Thr Gln Ala Leu Pro Pro Leu Ser Met Pro Ser Thr Ser
                485                 490                 495
His Cys Thr Pro Pro Pro Tyr Pro Thr Asp Cys Ser Ile Val Ser
            500                 505                 510
Phe Leu Ala Arg Leu Gly Cys Ser Ser Cys Leu Asp Tyr Phe Thr Thr
        515                 520                 525
Gln Gly Leu Thr Thr Ile Tyr Gln Ile Glu His Tyr Ser Met Asp Asp
    530                 535                 540
Leu Ala Ser Leu Lys Ile Pro Glu Gln Phe Arg His Ala Ile Trp Lys
545                 550                 555                 560
Gly Ile Leu Asp His Arg Gln Leu His Asp Phe Ser Ser Pro Pro His
                565                 570                 575
Leu Leu Arg Thr Pro Ser Gly Ala Ser Thr Val Ser Val Gly Ser Ser
            580                 585                 590
Glu Thr Arg Gly Glu Arg Val Ile Asp Ala Val Arg Phe Thr Leu Arg
        595                 600                 605
Gln Thr Ile Ser Phe Pro Pro Arg Asp Glu Trp Asn Asp Phe Asn Phe
    610                 615                 620
Asp Met Asp Ser Arg Arg Asn Lys Gln Gln Arg Ile Lys Glu Glu Gly
625                 630                 635                 640
Glu

<210> SEQ ID NO 12
<211> LENGTH: 27
<212> TYPE: DNA
<213> ORGANISM: Artificial Sequence
<220> FEATURE:
<223> OTHER INFORMATION: p73-F1 sense primer

<400> SEQUENCE: 12
tacgtgcacg taaagacacg ttgctcc                                       27

<210> SEQ ID NO 13
<211> LENGTH: 29
<212> TYPE: DNA
<213> ORGANISM: Artificial Sequence
```

```
<220> FEATURE:
<223> OTHER INFORMATION: p73-R1 antisense primer

<400> SEQUENCE: 13
tgctgcacgt tgctccacgt ggacgtacg                                    29

<210> SEQ ID NO 14
<211> LENGTH: 29
<212> TYPE: DNA
<213> ORGANISM: Artificial Sequence
<220> FEATURE:
<223> OTHER INFORMATION: p73-F2 sense primer

<400> SEQUENCE: 14
tacgtatact acgacgtgta cgtgaaggg                                    29

<210> SEQ ID NO 15
<211> LENGTH: 29
<212> TYPE: DNA
<213> ORGANISM: Artificial Sequence
<220> FEATURE:
<223> OTHER INFORMATION: p73-R2 antisense primer

<400> SEQUENCE: 15
atgaactacg acgtacgacg tccacgtat                                    29

<210> SEQ ID NO 16
<211> LENGTH: 30
<212> TYPE: DNA
<213> ORGANISM: Artificial Sequence
<220> FEATURE:
<223> OTHER INFORMATION: Sequence encoding HA peptide tag

<400> SEQUENCE: 16
atgtatccat atgatgttcc agattatgct                                   30

<210> SEQ ID NO 17
<211> LENGTH: 10
<212> TYPE: PRT
<213> ORGANISM: Artificial Sequence
<220> FEATURE:
<223> OTHER INFORMATION: HA peptide tag

<400> SEQUENCE: 17

Met Tyr Pro Tyr Asp Val Pro Asp Tyr Ala
1               5                   10

<210> SEQ ID NO 18
<211> LENGTH: 20
<212> TYPE: DNA
<213> ORGANISM: Artificial Sequence
<220> FEATURE:
<223> OTHER INFORMATION: p51-F1 sense primer

<400> SEQUENCE: 18
aaagaaagtt attaccgatg                                              20

<210> SEQ ID NO 19
<211> LENGTH: 20
<212> TYPE: DNA
<213> ORGANISM: Artificial Sequence
<220> FEATURE:
<223> OTHER INFORMATION: p51-R1 antisense primer

<400> SEQUENCE: 19
cgcgtggtct gtgttatagg                                              20
```

```
<210> SEQ ID NO 20
<211> LENGTH: 20
<212> TYPE: DNA
<213> ORGANISM: Artificial Sequence
<220> FEATURE:
<223> OTHER INFORMATION: p51-F2 sense primer

<400> SEQUENCE: 20
catggaccag cagattcaga                                              20

<210> SEQ ID NO 21
<211> LENGTH: 19
<212> TYPE: DNA
<213> ORGANISM: Artificial Sequence
<220> FEATURE:
<223> OTHER INFORMATION: p51-R2 antisense primer

<400> SEQUENCE: 21
catcaccttg atctggatg                                               19

<210> SEQ ID NO 22
<211> LENGTH: 20
<212> TYPE: DNA
<213> ORGANISM: Artificial Sequence
<220> FEATURE:
<223> OTHER INFORMATION: p51-F3 sense primer

<400> SEQUENCE: 22
ccacctggac gtattccact                                              20

<210> SEQ ID NO 23
<211> LENGTH: 18
<212> TYPE: DNA
<213> ORGANISM: Artificial Sequence
<220> FEATURE:
<223> OTHER INFORMATION: p51-R3 antisense primer

<400> SEQUENCE: 23
tggctcataa ggtaccag                                                18

<210> SEQ ID NO 24
<211> LENGTH: 19
<212> TYPE: DNA
<213> ORGANISM: Artificial Sequence
<220> FEATURE:
<223> OTHER INFORMATION: p51-F4 sense primer

<400> SEQUENCE: 24
catgagctga gccgtgaat                                               19

<210> SEQ ID NO 25
<211> LENGTH: 20
<212> TYPE: DNA
<213> ORGANISM: Artificial Sequence
<220> FEATURE:
<223> OTHER INFORMATION: p51-R4 antisense primer

<400> SEQUENCE: 25
tatcttcatc cgccttcctg                                              20

<210> SEQ ID NO 26
<211> LENGTH: 18
<212> TYPE: DNA
<213> ORGANISM: Artificial Sequence
<220> FEATURE:
```

```
<223> OTHER INFORMATION: p51-F5 sense primer

<400> SEQUENCE: 26
atgaaccgcc gtccaatt                                                 18

<210> SEQ ID NO 27
<211> LENGTH: 20
<212> TYPE: DNA
<213> ORGANISM: Artificial Sequence
<220> FEATURE:
<223> OTHER INFORMATION: p51-R5 antisense primer

<400> SEQUENCE: 27
gtgctgagga aggtactgca                                               20

<210> SEQ ID NO 28
<211> LENGTH: 20
<212> TYPE: DNA
<213> ORGANISM: Artificial Sequence
<220> FEATURE:
<223> OTHER INFORMATION: p51-F6 sense primer

<400> SEQUENCE: 28
tgaagatcaa agagtccctg                                               20

<210> SEQ ID NO 29
<211> LENGTH: 20
<212> TYPE: DNA
<213> ORGANISM: Artificial Sequence
<220> FEATURE:
<223> OTHER INFORMATION: p51-R6 antisense primer

<400> SEQUENCE: 29
ctagtggctt tgtgcctttg                                               20
```